US008226986B2

(12) United States Patent
Tomaselli et al.

(10) Patent No.: US 8,226,986 B2
(45) Date of Patent: Jul. 24, 2012

(54) LIQUID CHALCOGENIDE COMPOSITIONS AND METHODS OF MANUFACTURING AND USING THE SAME

(75) Inventors: Kevin J. Tomaselli, San Diego, CA (US); Paul A. Hill, Snohomish, WA (US); Thomas L. Deckwerth, Seattle, WA (US); Edward A. Wintner, Belmont, MA (US); Csaba Szabo, Seattle, WA (US)

(73) Assignee: Ikaria, Inc., Seattle, WA (US)

( * ) Notice: Subject to any disclaimer, the term of this patent is extended or adjusted under 35 U.S.C. 154(b) by 0 days.

(21) Appl. No.: 13/049,220

(22) Filed: Mar. 16, 2011

(65) Prior Publication Data

US 2011/0165268 A1 Jul. 7, 2011

Related U.S. Application Data

(60) Division of application No. 12/023,840, filed on Jan. 31, 2008, now Pat. No. 7,923,037, which is a continuation-in-part of application No. 11/868,348, filed on Oct. 5, 2007, now abandoned.

(60) Provisional application No. 60/896,727, filed on Mar. 23, 2007, provisional application No. 60/849,900, filed on Oct. 5, 2006.

(51) Int. Cl.
*A61K 33/00* (2006.01)
*A61K 33/04* (2006.01)
*C01B 17/16* (2006.01)
*C01B 17/22* (2006.01)
*A61P 39/00* (2006.01)
*A01N 59/00* (2006.01)
*A01N 59/02* (2006.01)

(52) U.S. Cl. ........ 424/708; 424/600; 424/696; 424/706; 424/709; 424/711; 514/706; 423/563; 423/566.2

(58) Field of Classification Search ........................ None
See application file for complete search history.

(56) References Cited

U.S. PATENT DOCUMENTS

| 5,770,583 | A | 6/1998 | Haslwanter et al. |
| 5,948,392 | A | 9/1999 | Haslwanter et al. |
| 2007/0265223 | A1 | 11/2007 | Tomaselli et al. |

FOREIGN PATENT DOCUMENTS

| WO | WO-2005/041655 | 5/2005 |
| WO | WO-2006/113914 | 10/2006 |
| WO | WO-2006/119258 | 11/2006 |
| WO | WO-2007/124447 | 11/2007 |
| WO | WO-2008/070741 | 6/2008 |
| WO | WO-2008/079993 | 7/2008 |
| WO | WO-2008/157393 | 12/2008 |

OTHER PUBLICATIONS

International Preliminary Report on Patentability for PCT/US2007/080613, mailed Apr. 7, 2009, 7 pgs.
International Search Report and Written Opinion for PCT/US2007/080613, mailed Apr. 7, 2008, 14 pgs.
Non-Final Office in U.S. Appl. No. 12/023,840, mailed Jul. 21, 2010, 13 pgs.
Almeida, et al., "Differential Sensitivity of Lung and Brain to Sulfide Exposure: A Peripheral Mechanism for Apnea", *Toxicological Sciences 50*. 1999, 287-293.
Beauchamp, Jr., et al., "A Critical Review of the Literature on Hydrogen Sulfide Toxicity, Leon Goldberg (ed.)", *Critical Reviews in Toxicology*, vol. 13, Issue 1, CRC Press, Inc., Boca Raton, Florida 1984, 25-97.
Bhatia, et al., "Role of hydrogen sulfide in acute pancreatitis and associated lung injury", *The FASEB Journal express article 10.1096/fj.04-3023lje* Jan. 25, 2005, 17 pgs.
Bian, et al., "Role of Hydrogen Sulfide in the Cardioprotection Caused by Ischemic Preconditioning in the Rat Heart and Cardiac Myocytes", *The Journal of Pharmacology and Experimental Therapeutics 316*(2): 2006, 670-678.
Blackstone, et al., "H$_2$S Induces a Suspended Animation-Like State in Mice", *Science 308;518*; Apr. 22, 2005.
Blackstone, et al., "Suspended Animation-Like State Protects Mice From Lethal Hypoxia", *Shock 27*(4): Apr. 2007, 370-372.
Chen, et al., "Kinetics of Oxidation of Aqueous Sulfide by O$_2$", *Environmental Science & Technology 6*(6); Jun. 1972, 529-537.
Doeller, et al., "Polarographic measurement of hydrogen sulfide production and consumption by mammalian tissues", *Analytical Biochemistry 341*; Oct. 2005, 40-51.
Dziewiatkowski, Dominic D., "Conversion of Sulfide to Cystine Sulfur in the Rat, with Use of Radioactive Sulfur", *J. Biol. Cham 1946 164*;, 165-171.
Fiorucci, et al., "Inhibition of Hydrogen Sulfide Generation Contributes to Gastric Injury Caused by Anti-Inflammatory Nonsteroidai Drugs", *Gastroenterology 129*(4): 2005, 1210-1224.
Fiorucci, et al., "The Emerging Roles of Hydrogen Sulfide in the Gastrointestinal Tract and Liver", *Gastroenterology 131*(1): Jul 2006, 259-271.
Fiorucci, et al., "The Third Gas H$_2$S Regulates Perfusion Pressure in Both the Isolated and Perfused Normal Rat Liver and in Cirrhosis", *Hepatology 42*(3): Sep. 2005, 539-548.
Geng, et al., "H2S generated by heart in rat and its effects on cardiac function", *Biochemical and Biophysical Research Communications 313*; 2004, 362-368.
Haouzi, et al., "H$_2$S induced hypometabolism in mice is missing in sedated sheep", *Respiratory Physiology & Neurobiology 160*; Jan. 2008, 109-115.
Hero, H. et al., "Tarnishing of a Low-gold Dental Alloy in different Structural States", *NIOM, Scandinavian Institute of Dental Materials* Mar. 1983, 371-376.
Hoffmann, et al., "Kinetics and Mechanism of the Oxidation of Sulfide by Oxygen; Catalysis by Homogeneous Metal—Phthalocyanine Complexes", *Environmental Science & Technology 13*(11); Nov. 1979, 1406-1414.
Hui, et al., "Changes in arterial hydrogan sulfide (H$_2$S) content during septic shock and endotixin shock in rats", *Journal of Infection 47*; 2008, 155-60.

(Continued)

*Primary Examiner* — Ernst Arnold
(74) *Attorney, Agent, or Firm* — Diehl Servilla LLC

(57) ABSTRACT

The present invention provides novel stable, liquid compositions comprising chalcogenides or salts thereof. These compositions may be used for a variety of purposes, including the treatment and prevention of ischemic or hypoxic injury, as well as in the preservation of biological matter.

5 Claims, 20 Drawing Sheets

OTHER PUBLICATIONS

Johansen, et al., "Exogenous hydrogen sulfide ($H_2S$) protects against regional myocardial ischemia-reperfusion injury", *Basic Resrarch in Cardiology 101*(1); 2006, 53-60.

Kage, et al., "Determination of Thiosulfate in Body Fluids by GC and GC/MS", *Journal of Analytical Toxicology 15*; May/Jun. 1991, 148-150.

Kage, et al., "Extractive Alkylation and Gas Chromatographic Analysis of Sulfide", *Journal of Forensic Sciences, JFSCA 33*(1); Jan. 1988, 217-222.

Kotronarou, et al., "Oxidation of Hydrogen Sulfide in Aqueous Solution by Ultrasonic Irradiatin", *Environmental Science & Technology 26*(12); 1992, 2420-2428.

Kraus, et al., "Sulfide consumption by mussel gill mitochondria is not strictly tied to oxygen reduction: measurements using a novel polarographic sulfide sensor", *Journal of Experimental Biology 207*; Oct. 2004, 3667-3679.

O'Brien, et al., "Kinetics of Oxygenation of Reduced Sulfur Species in Aqueous Solution", *Environmental Science & Technology 11*(12); Nov. 1977, 1114-1120.

Pan, et al., "Endogenous hydrogen sulfide contributes to the cardioprotection by metabiloc inhibiiton preconditioning in the rat ventricular myocytes", *Journal of Molecular and Cellular Cardiology 40*; 2006, 119-130.

Qingyou, et al., "Impact of hydrogen sulfide on carbon monoxide/heme oxygenase pathway in the pathogenesis of hypoxic pulmonary hypertension", *Biochemical and Biophysical Research Communications 317*; 2004, 30-37.

Qu, et al., "Hydrogen Sulfide is a Mediator of Cerebral Ischemic Damage", *Stroke 37*: Jan. 26, 2006, 889-893.

Searcy, et al., "Hydrogen sulfide consumption measured at low steady state concentrations using a sulfidostat", *Anal. Biochem. 324* 2004, 269-275.

Srilatha, et al., "Possible role for novel gasotransmitter hydrogen sulphide in erectile dysfunction—a pilot study", *European Journal of Pharmacology 535*; 2006, 280-282.

Szabo, et al., "P1 Infusion of sodium sulfide improves myocardial and endothelial function in a canine model of cardiopulmonary bypass", *Critical Care 11*(*Suppl 2*):S2 Mar. 22, 2007.

Tossell, J. A., "Theoretical studies on possible sulfur oxides with +2 oxidation states in aqueous solution", *Chemical Geology 141*; 1997, 93-103.

Wowk, Brian, "Is Hydrogen Sulfide the Secret to Suspended Animation?", *Cryoics*. 26(4) Jul./Aug. 2005.

Wu, et al., "Hydrogen sulfide ameliorates vascular calcification indiced by vitamin D3 plus nicotine in rats", *Acta Pharmacologica Sinica 27*(3); Mar. 2006, 299-306.

Yang, et al., "Hydrogen sulfide-induced apoptosis of human aorta smooth muscle cells via the activationof mitogen-activated protein kinases and caspase-3", *The FASEB Journal, express article 10.1096* Sep. 15, 2004, 21 pgs.

Zanardo, et al., "Hydrogen sulfide is an endogenous modulator of leukocyte-mediated inflammation", *The FASEB Journal express article 10.1096, 20*: Oct. 2006, E1-E8.

Zhao, et al., "$H_2S$-induced vasorelaxation and underlying cellular and molecular mechanisms", *Am J Physiol Heart Circ Physiol 283*: 2002, H474-H480.

Zhao, et al., "The vasorelaxant effect of $H_2S$ as a novel endogenous gaseous $K_{ATP}$ channel opener", *The EMBO Jouranl 20*(21); 2001, 6008-6016.

Zhu, et al., "Hydrogen sulfide and its possible roles in myocardial ischemia in experimental rats", *J. Appl. Physiol. 102*; Jan. 2007, 261-268.

Miron, Gilles et al., "Behavioural response of three nereid polychaetes to injection of sulfide inside burrows", *Marine Ecology Progress Series*, vol. 101 1993, 147-155.

Liquid Composition Formulation IV Is Stable (>97%) Over 129 Days at Room Temperature n=5,6 per group
* p<0.05 p<0.05 vs. baseline
* p <0.05 vs. vehicle

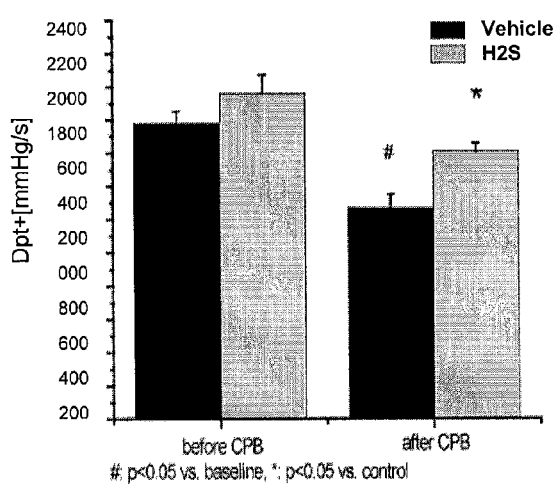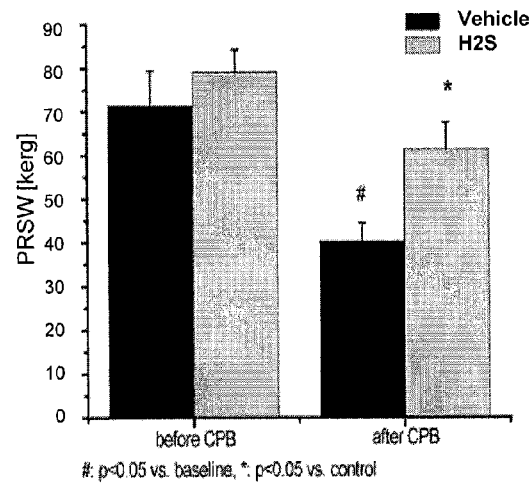
Figure 17A                    Figure 17B

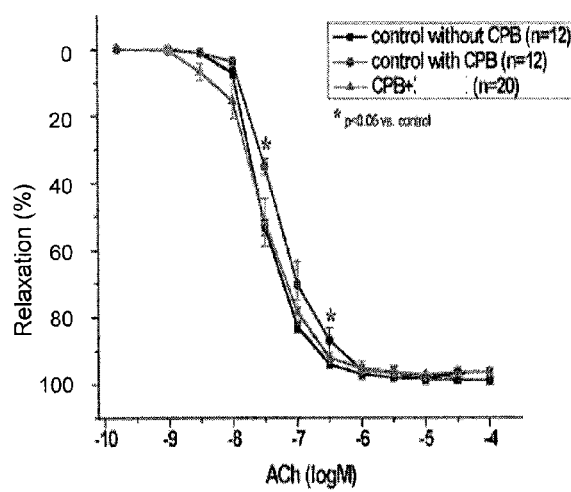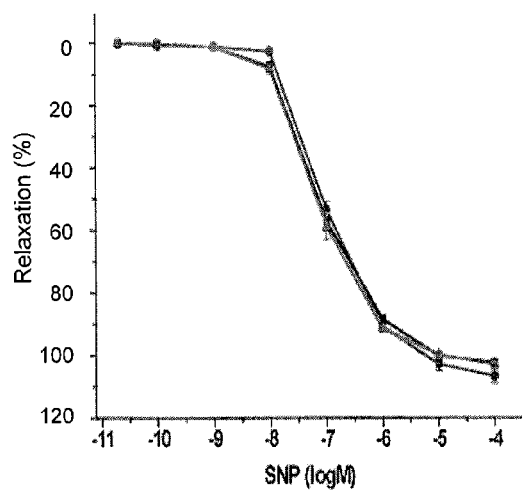
Figure 19A                    Figure 19B

LIQUID CHALCOGENIDE COMPOSITIONS AND METHODS OF MANUFACTURING AND USING THE SAME

CROSS-REFERENCE TO RELATED APPLICATION

This application is a divisional application of U.S. patent application Ser. No. 12/023,840, filed Jan. 31, 2008, now U.S. Pat. No. 7,923,037, which is a continuation-in-part of U.S. patent application Ser. No. 11/868,348, filed Oct. 5, 2007, now abandoned, which claims the benefit of the filing date of U.S. Provisional Application No. 60/896,727, filed on Mar. 23, 2007, and U.S. Provisional Application No. 60/849,900, filed on Oct. 5, 2006, the entire contents of which are incorporated herein by reference.

BACKGROUND OF THE INVENTION

1. Field of the Invention

The present invention relates generally to liquid chalcogenide compositions, more particularly to stable liquid pharmaceutical compositions comprising chalcogenides. The invention further relates to the use of such compositions to protect cells and animals from injury, disease, and premature death.

2. Description of the Related Art

Compounds containing a chalcogen element, i.e., those in Group 6 of the periodic table, but excluding oxides, are commonly termed "chalcogenides" or "chalcogenide compounds." These elements are sulfur (S), selenium (Se), tellurium (Te) and polonium (Po). Common chalcogenides contain one or more of S, Se, and Te, in addition to other elements.

It has been recently shown that treatment with chalcogenides induces stasis of biological matter and protects biological matter from hypoxic and ischemic injury. In these studies, it was demonstrated that hydrogen sulfide ($H_2S$) gas, a potent inhibitor of oxygen consumption, can reduce metabolism and protect mice and rats from hypoxic injuries (PCT Publication No. WO2005/041655). Although hydrogen sulfide gas has not been typically considered a medical gas, this unexpected result presents exciting possibilities for the treatment or prevention of a number of animal and human diseases, particularly hypoxia and ischemia-related diseases and injuries.

Certain chalcogenide compounds (e.g., hydrogen sulfide and hydrogen selenide), are not stable in the presence of oxygen due to their ability to react chemically with oxygen, leading to their oxidation and chemical transformation. For example, the chemical transformation of sulfide limits its use as a pharmaceutical due to limited stability, limited shelf-life, and the potential for the introduction of oxidation products during manufacture, storage, or use. Potential oxidizing agents of sulfide include oxygen, carbon dioxide, and inherent metal impurities that can produce a mixture of oxidation products (e.g., sulfite, sulfate, thiosulfate, polysulfides, dithionate, polythionate, and elemental sulfur). Thus, the rapid oxidation of sulfide during storage limits its use as a pharmaceutical agent.

To provide a pharmaceutical benefit to a cell or patient in need of treatment with a chalcogenide, finished dosage forms that are stable, easily and reproducibly manufactured, and designed for standard routes of administration are needed. Clearly, there is a need in the art for stable, liquid pharmaceutical compositions of chalcogenides, including those containing sulfide. Sulfide is defined as sulfur in its −2 valence state, either as $H_2S$ or as a salt thereof (e.g., NaHS, $Na_2S$, etc.) that may be conveniently administered to patients, both in a controlled medical environment e.g., for treatment of disease, as a treatment in the field during an emergency, or in critical care in response to a catastrophic injury or life-threatening medical event. The present invention meets this need by providing novel, stable, liquid pharmaceutical compositions of chalcogenides, which are demonstrated herein to protect animals from injury and death resulting from hypoxic and/or ischemic conditions, as well as other injuries and disease conditions.

BRIEF SUMMARY OF THE INVENTION

The present invention provides liquid compositions of chalcogenides, as well as method of preparing and using the same.

In one embodiment, the present invention provides a composition comprising a stable liquid pharmaceutical chalcogenide or chalcogenide compound or salt or precursor thereof in a pharmaceutically acceptable carrier, wherein the concentration, pH and oxidation products of said chalcogenide or chalcogenide compound or salt remain within a range of acceptance criteria after storage of said liquid pharmaceutical composition.

In various embodiments, the chalcogenide compound or chalcogenide salt is selected from the group consisting of: $H_2S$, $Na_2S$, NaHS, $K_2S$, KHS, $Rb_2S$, $Cs_2S$, $(NH_4)_2S$, $(NH_4)HS$, BeS, MgS, CaS, SrS, and BaS.

In other embodiments, the chalcogenide compound or chalcogenide salt is selected from the group consisting of: $H_2Se$, $Na_2Se$, NaHSe, $K_2Se$, KHSe, $Rb_2Se$, $Cs_2Se$, $(NH_4)_2Se$, $(NH_4)HSe$, BeSe, MgSe, CaSe, SrSe, PoSe and BaSe.

In particular embodiments, the chalcogenide compound or chalcogenide salt is sulfide and has a concentration in the range of 95 mM to 150 mM.

In particular embodiments wherein said chalcogenide compound or chalcogenide salt is sulfide, said sulfide is present in amounts ranging from about 80% to about 100%, about 90% to 100%, or about 95% to 100% by w/v.

In particular embodiments, the liquid is sodium hydroxide.

In certain embodiments, the composition has a pH in the range of 6.5 to 8.5.

In one embodiment, the composition has an oxygen content of less than or equal to 5 µM.

In one embodiment, the composition further comprises one or more oxidation products selected from polysulfide, sulfite, sulfate and thiosulfate. The oxidation products may be sulfate in the range of (0%-1.0%), or sulfite in the range of (0%-1.0%), or polysulfide in the range of (0%-1%) or thiosulfate in the range of (0%-1.0%).

The storage period may be about 3 months at a range of (23°-27°) or 6 months at a range of (23°-27°).

In one embodiment, the composition has an osmolarity in the range of 250-330 mOsmol/L. It may be isotonic or near isotonic.

In certain embodiments, the composition is stored in an impermeable container.

In other embodiments, the composition further comprises a chelating agent. The chelating agent may be Diethylenetriaminepentaacetic acid (DTPA) or deferoxamine. DTPA may be present in the range of 0.1 mM to 1.0 mM. Deferoxamine in the range of 0.1 mM to 1 mM.

In one embodiment, the composition further comprises a pH modifying agent. The pH modifying agent may selected from the group consisting of: carbon dioxide, sodium hydroxide, hydrochloric acid or hydrogen sulfide.

In another embodiment, the composition further comprises a reducing agent. The reducing agent may be selected from the group consisting of: dithiothreitol (DTT) or glutathione. The amount of dithiothreitol (DTT) may be in the range of 0.1 mM to 1 M. The amount of glutathione may be in the range of 0.1 mM to 1 M.

In a further embodiment, the composition further comprises a free radical scavenger. The free radical scavenger may be selected from the group consisting of (6-hydroxy-2, 5,7,8-tetramethyl chroman-2-carboxylic acid) (Trolox) or Tris(2-Carboxyethyl) phosphine Hydrochloride (TCEP). The free radical scavenger may be a spin-trap agent. The free radical scavenger may be selected from the group consisting of: N-t-butyl-phenylnitrone (PBN), 2,2,6,6-tetramethylpiperidine-N-oxyl (TEMPO), 4-Hydroxy-2,2,6,6-tetramethylpiperidine-1-oxyl (TEMPOL).

In another embodiment, the composition further comprises a preservative. The preservative may be selected from the group consisting of benzyl alcohol, phenol, methyl paraben, ethyl paraben, propyl paraben, butyl paraben, or benzalkonium chloride. The preservative may be present in the range of benzyl alcohol (0%-2.0%) (w/v), phenol (0%-0.5%) (w/v), methyl paraben (0%-0.25%) (w/v), ethyl paraben (0%-0.25%) (w/v), propyl paraben (0%-0.25%) (w/v), butyl paraben (0%-0.4%) (w/v), benzalkonium chloride, (0%-0.02%) (w/v).

In one embodiment, one equivalent of hydrogen sulfide gas is dissolved into one equivalent of sodium hydroxide solution, wherein said resulting composition has a pH in the range of 6.5 to 8.5, an osmolarity in the range of 250-330 mOsmol/L, an oxygen content of less than or equal to 5 µM, and comprises oxidation products are the range of 0%-3.0% (w/v) after storage for three months.

In a related embodiment, one equivalent of hydrogen sulfide gas is dissolved into one equivalent of sodium hydroxide solution, wherein the resulting composition has a pH in the range of 6.5 to 8.5, an osmolarity in the range of 250-330 mOsmol/L, an oxygen content of less than or equal to 5 µM, and comprises oxidation products are the range of 0%-2.0% (w/v) after storage for five months.

In yet a further related embodiment, one equivalent of hydrogen sulfide gas is dissolved into one equivalent of sodium hydroxide solution, wherein said resulting composition has a pH in the range of 7.5 to 8.5, an osmolarity in the range of 250-330 mOsmol/L, an oxygen content of less than or equal to 5 µM, and comprises oxidation products are the range of 1%-2.0% (w/v) after storage for five months.

The present invention further provides methods of preparing a liquid composition of a sulfide suitable for administration to an animal, comprising:

(a) Dissolving one equivalent of hydrogen sulfide gas into one equivalent of liquid, thereby producing a composition of sulfide; and (b) adjusting the pH of the composition resulting from step (a) to a pH in the range of 6.5 to 8.5, wherein said composition thereby producing a liquid composition of a sulfide suitable for administration to an animal.

In certain embodiments, the pH is adjusted by the addition of one or more or hydrogen chloride, carbon dioxide, sodium hydroxide, and hydrogen sulfide. In other embodiments, the pH is adjusted by dissolving nitrogen, carbon dioxide, and/or hydrogen sulfide into the composition resulting from step (a). The pH may also be adjusted by dissolving a combination of nitrogen and carbon dioxide or a combination of nitrogen and hydrogen sulfide into the composition resulting from step (a). In addition, the pH may be adjusted by dissolving hydrogen sulfide into the composition resulting from step (a).

The method may further comprise adjusting the osmolarity of the composition resulting from step (b) to an osmolarity in the range of 250-350 mOsmol/L.

The method may further comprise dispensing the composition resulting from step (b) under inert atmosphere or noble gas into light-protective vials.

The method may further comprise adding an excipient to the composition resulting from step (b).

In particular embodiments of the methods, the oxygen content is less than or equal to 5 µM for about six months.

In another embodiment, the present invention includes a kit comprising one or more containers comprising a composition of a chalcogenide or chalcogenide salt, wherein said composition has a pH in the range of 6.5 to 8.5.

In one embodiment, the containers are light-protective, such as amber vials. In another embodiment, the containers are gas impermeable.

In certain kits, the composition is stored in said container under an inert atmosphere or noble gas.

In particular embodiments, the inert or noble gases may be Helium (He), Neon (Ne), Argon (Ar), Krypton (Kr), Xenon (Xe), or Radon (Rn).

In yet another related embodiment, the present invention provides a method for treating human disease or injury of a biological material exposed to ischemic or hypoxic conditions comprising contacting the biological material with an effective amount of a composition of a chalcogenide or chalcogenide salt.

In various embodiments, the contacting is intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, intraocularly, subcutaneously, subconjunctival, intravesicularly, mucosally, intrapericardially, intraumbilically, intraocularally, orally, locally, by injection, by infusion, by continuous infusion, by absorption, by adsorption, by immersion, by localized perfusion, via a catheter, or via a lavage.

In particular embodiments, said chalcogenide or chalcogenide salt is selected from the group consisting of: $H_2S$, $Na_2S$, NaHS, $K_2S$, KHS, $Rb_2S$, $CS_2S$, $(NH_4)_2S$, $(NH_4)HS$, BeS, MgS, CaS, SrS, and BaS.

In particular embodiments, said chalcogenide or chalcogenide salt is selected from the group consisting of: $H_2Se$, $Na_2Se$, NaHSe, $K_2Se$, KHSe, $Rb_2Se$, $CS_2Se$, $(NH_4)_2Se$, $(NH_4)HSe$, BeSe, MgSe, CaSe, SrSe, and BaSe.

In one embodiment, the ischemic or hypoxic condition results from an injury to the material, the onset or progression of a disease that adversely affects the material, or hemorrhaging of the material.

In another embodiment, the material is contacted with the composition before the injury, before the onset or progression of the disease, or before hemorrhaging of the material.

In a different embodiment, the material is contacted with the composition after the injury, the onset or progression of the disease, or the hemorrhaging of the material.

In one embodiment, the injury is from an external physical source.

In a particular embodiment, the injury is a surgery.

In certain embodiments, the material is contacted with the composition in an amount and for a time that protects the material from damage or death resulting from the injury, the onset or progression of the disease, or hemorrhaging in the material.

In related embodiments, the material is selected from the group consisting of: cells, tissues, organs, organisms, and animals. In specific embodiments, the material is an animal, and in more specific embodiments, the animal is a mammal or a human.

In one embodiment, the biological material comprises platelets.

In another, the biological material is to be transplanted.

In yet another, the biological material is at risk for reperfusion injury.

In one particular embodiment, the biological material is at risk for hemorrhagic shock.

BRIEF DESCRIPTION OF THE SEVERAL VIEWS OF THE DRAWING(S)

Figure 11:
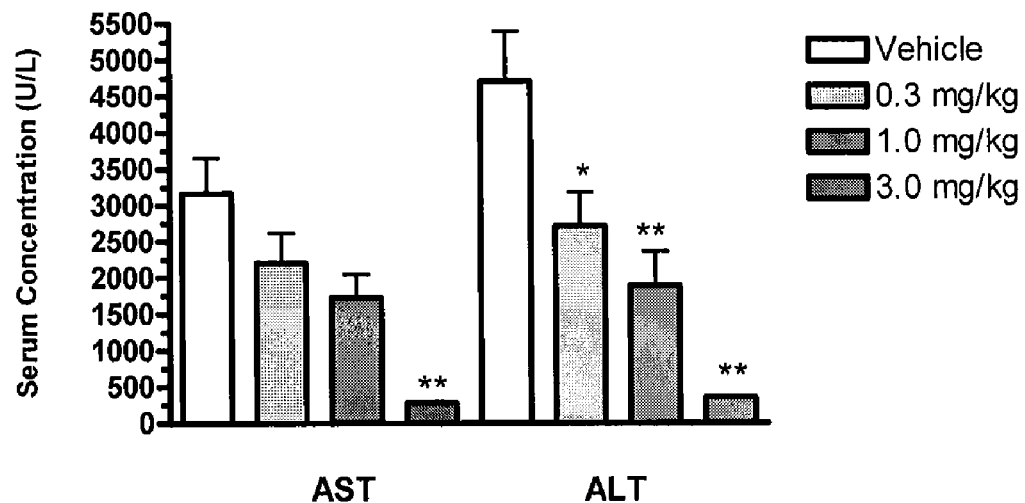

FIG. 11 is a graph depicting the serum AST and ALT levels of mice treated with the indicated amounts of Liquid Pharmaceutical Composition IV. AST levels achieved statistically significant reduction at the highest tested concentration (3.0 mg/kg). ALT levels were reduced in the three treatment groups (0.3 mg/kg, 1.0 mg/kg, and 3.0 mg/kg) compared to vehicle. Statistically significant p-values of 0.05 (*) and p<0.01 (**) are indicated.

Figure 12:
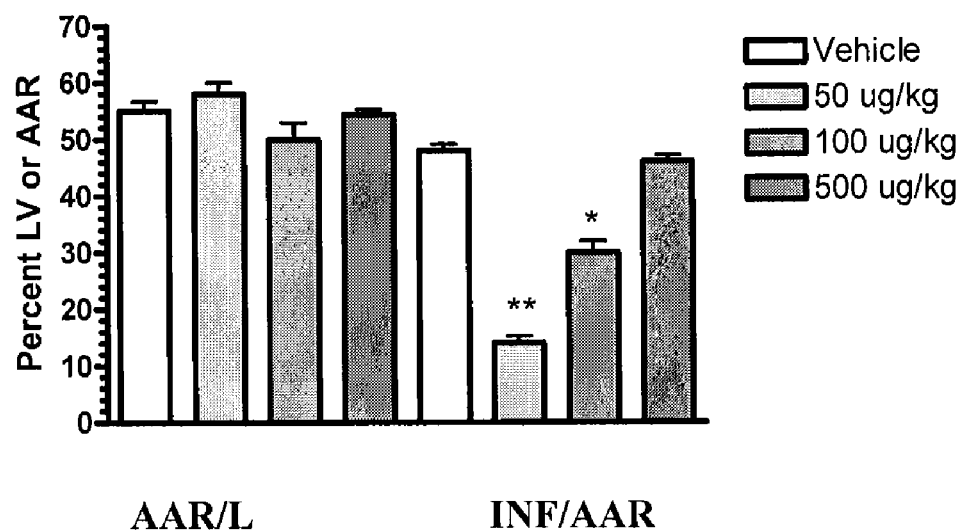

FIG. 12 is a graph depicting the percent LV or AAR in mice treated with the indicated amounts of a liquid pharmaceutical composition of sulfide. Statistically significant p-values of 0.05 (*) and p<0.01 (**) are indicated.

Figure 13A:
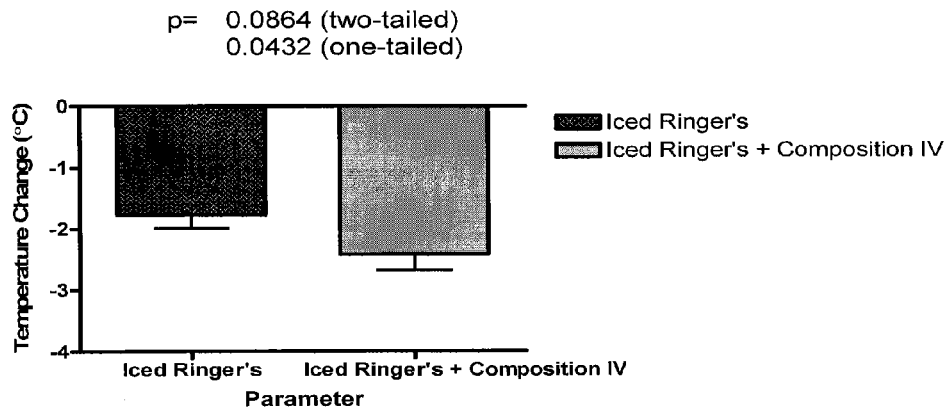
Figure 13B:
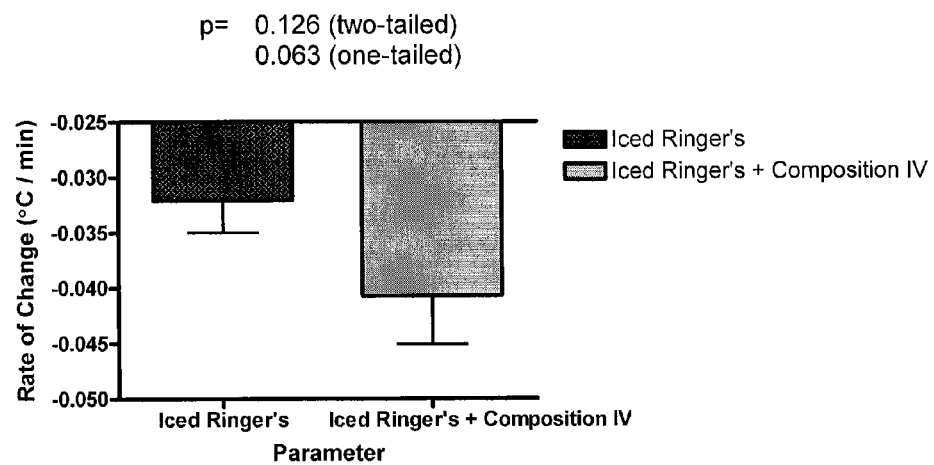

FIGS. 13A and 13B are graphs depicting the core body temperature of pigs treated with Iced Ringer's in the presence or absence of Liquid Pharmaceutical Composition IV. FIGS. 13A and 13B show the results obtained from two experiments with p-values provided.

Figure 14:
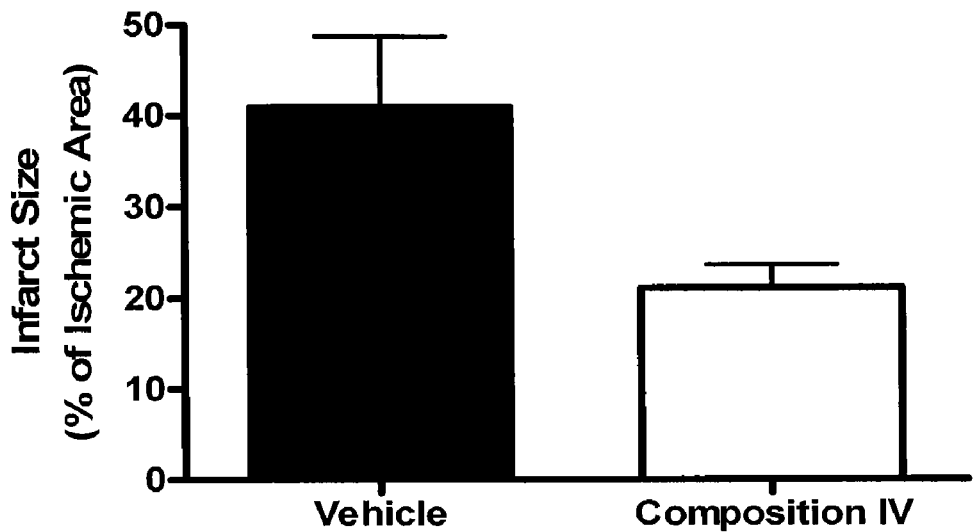

FIG. 14 is a graph depicting infarct size in pigs subjected to ischemia and reperfusion in the presence of control vehicle or Liquid Pharmaceutical Composition IV.

Figure 15:
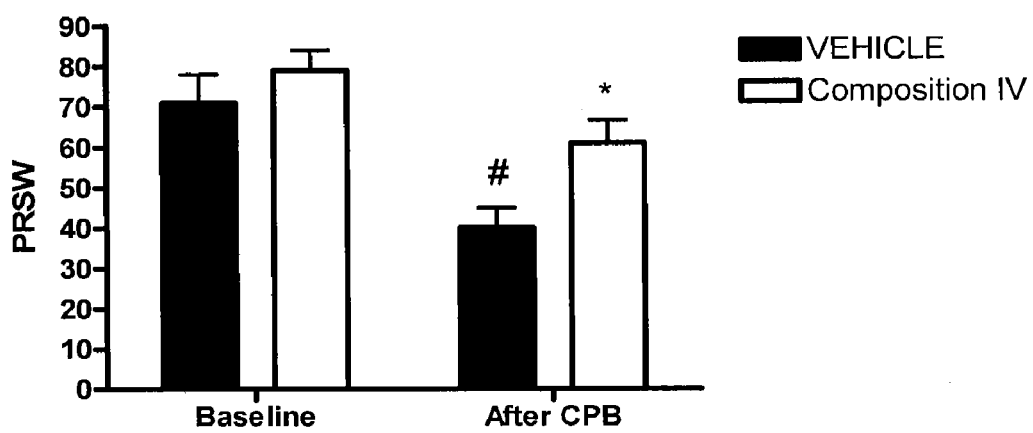

FIG. 15 is a graph depicting preload recruitable stroke work (PRSW) declines in dogs in response to ischemia, in the presence of control vehicle or Liquid Pharmaceutical Composition IV.

Figure 16:
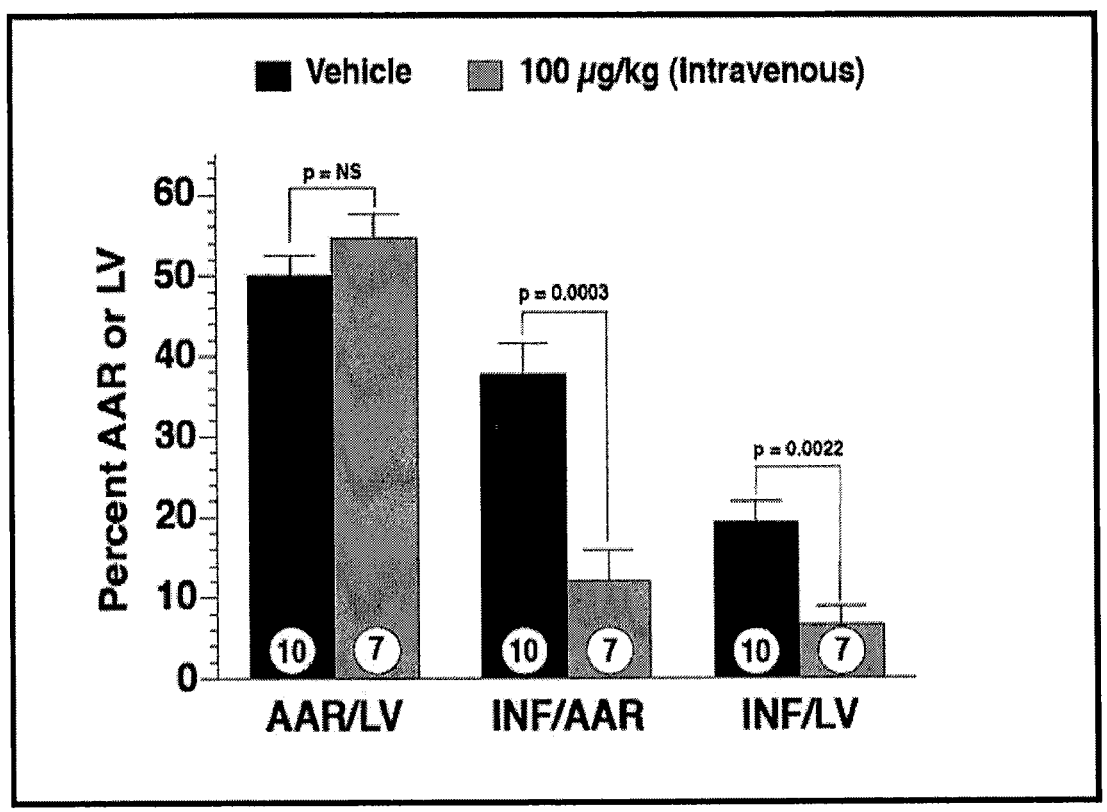

FIG. 16 is a graph depicting percent AAR or LV in animals pretreated with control vehicle or Liquid Pharmaceutical Composition IV.

FIG. 17 demonstrates left ventricular function is animals before or after cardiopulmonary bypass in the presence of control vehicle or hydrogen sulfide. FIG. 17A is a graph showing left ventricular dP/dT in animals both before and after cardiopulmonary bypass in the presence of control vehicle or parenteral hydrogen sulfide. FIG. 17B is a graph showing PRSW in animals both before and after cardiopulmonary bypass in the presence of control vehicle or parenteral hydrogen sulfide.

Figure 18:
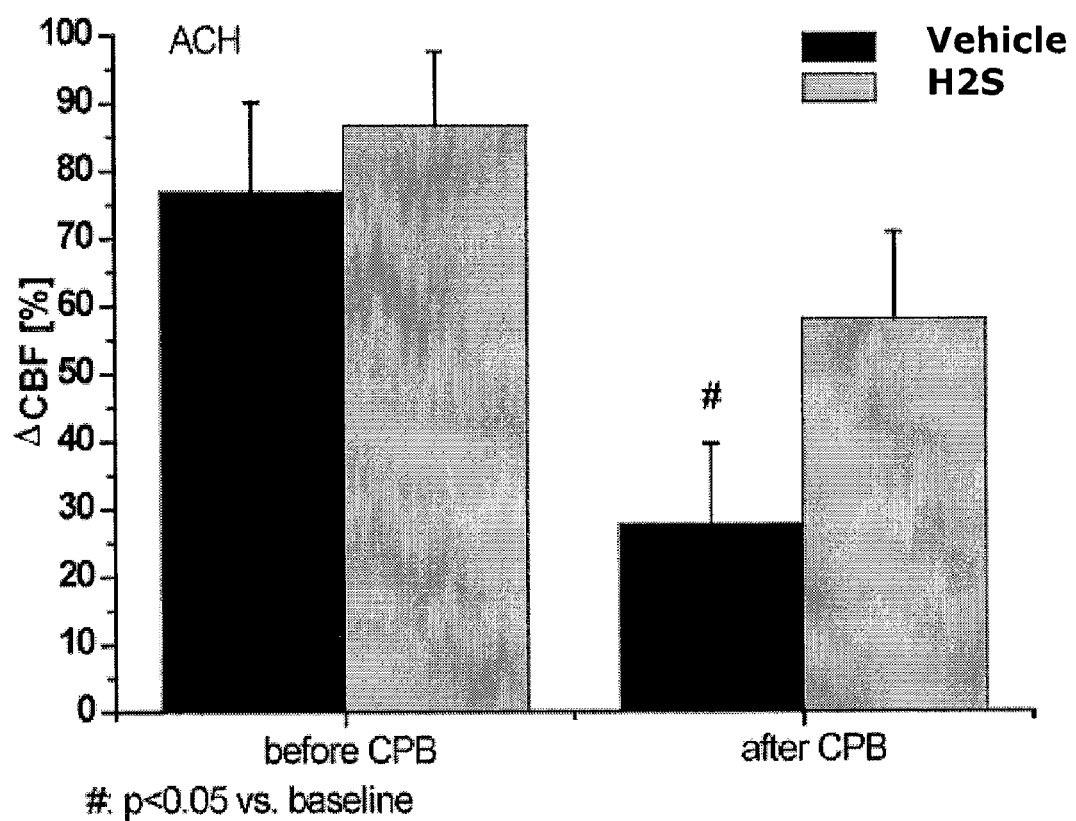

FIG. 18 is a graph demonstrating endothelial cell function in vivo, which depicts DCBF [%] in animals before or after cardiopulmonary bypass in the presence of control vehicle or hydrogen sulfide.

FIG. 19 demonstrates endothelial function ex vivo in the presence of control vehicle or hydrogen sulfide. FIG. 19A is a graph depicting vasorelaxation in response to acetylcholine with or without cardiopulmonary bypass in the presence of control vehicle or hydrogen sulfide. FIG. 19B is a graph depicting vasorelaxation in response to SNP with or without cardiopulmonary bypass in the presence of control vehicle or hydrogen sulfide.

Figure 20A:
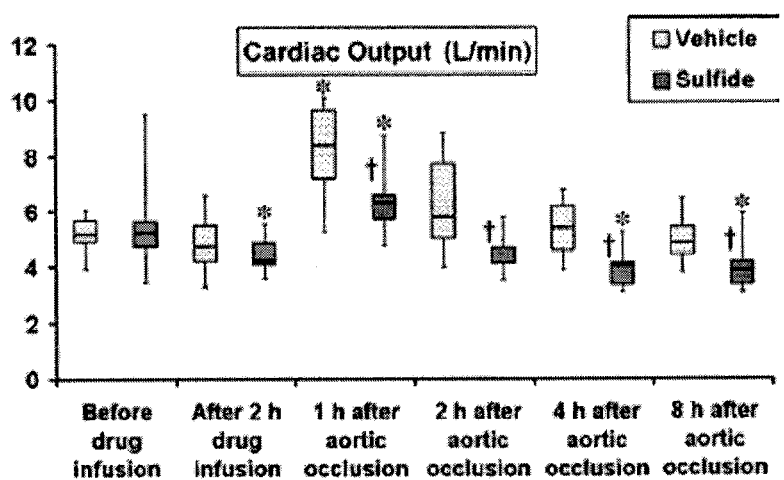
Figure 20B:
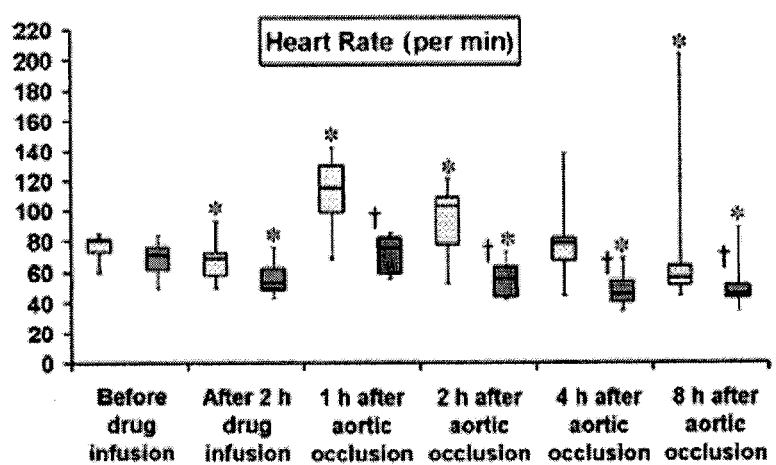
Figure 20C:
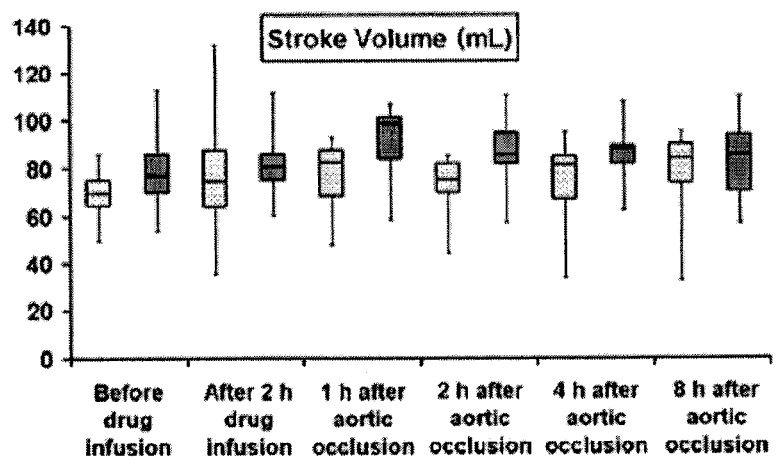

FIG. 20 provides graphs depicting cardiac output (FIG. 20A), heart rate (FIG. 20B), and stroke volume (FIG. 20C) in the vehicle (light bars) and sulfide-treated (dark bars) animals. All data are median (quartiles, range), n=8 in each group. *P<0.05 vs. before drug infusion within each group, †P<0.05 control vs. sulfide.

Figure 21A:
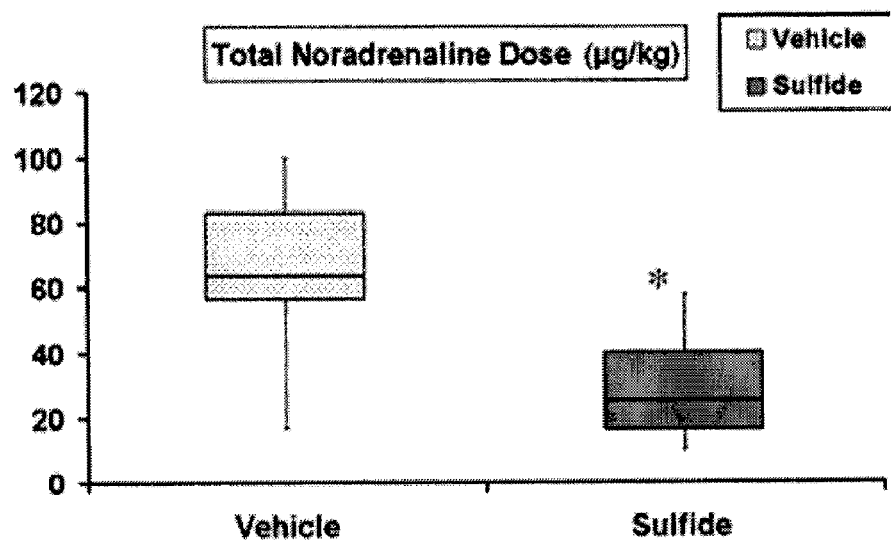
Figure 21B:
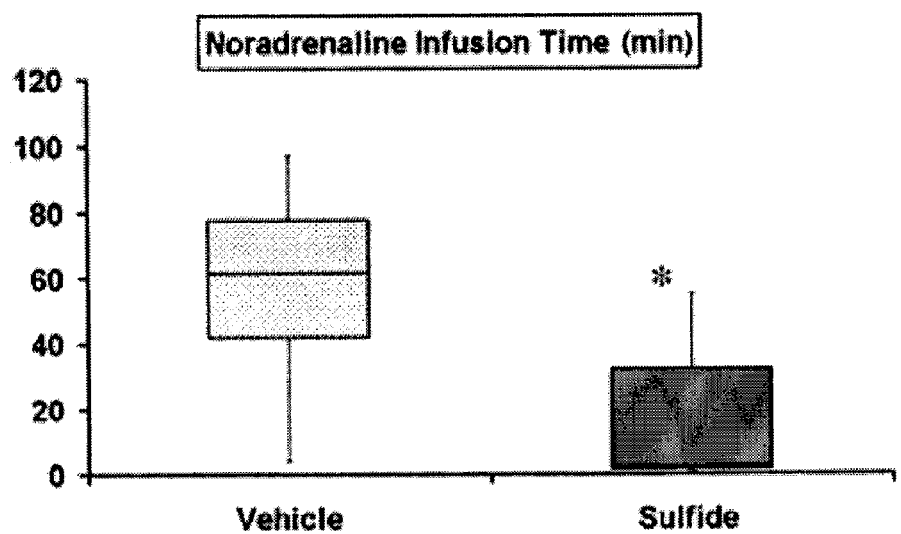

FIG. 21 provides graphs demonstrating the total noradrenaline dose (FIG. 21A) and noradrenaline infusion time (FIG. 21B) in the vehicle (light bars) and sulfide-treated (dark bars) animals. All data are median (quartiles, range), n=8 in each group. *P<0.05 control vs. sulfide.

Figure 22A:
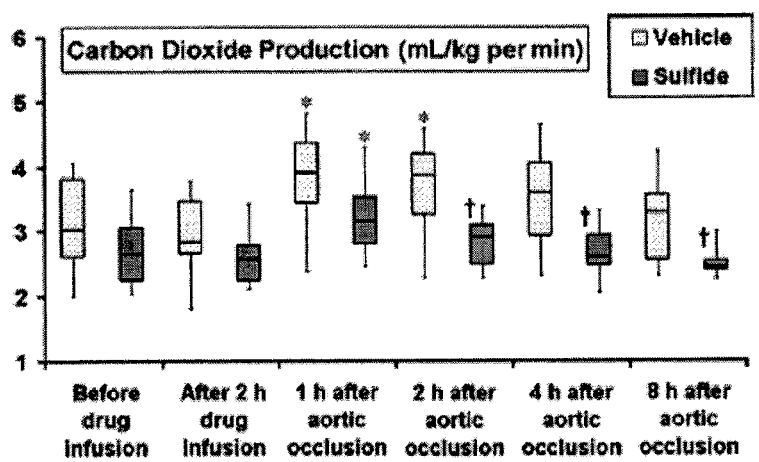
Figure 22B:
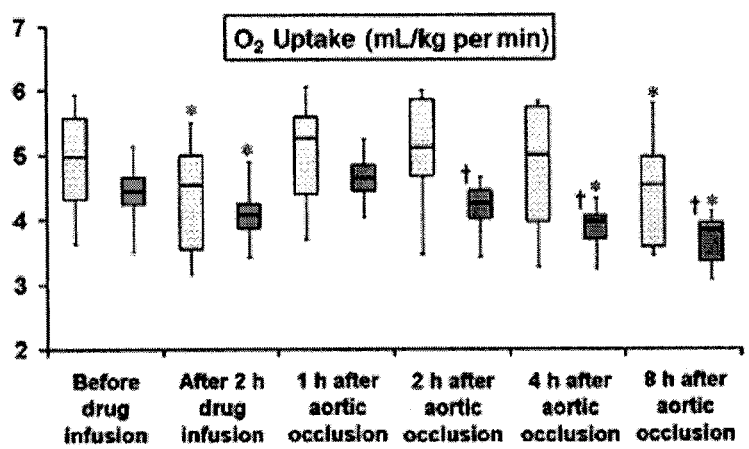
Figure 22C:
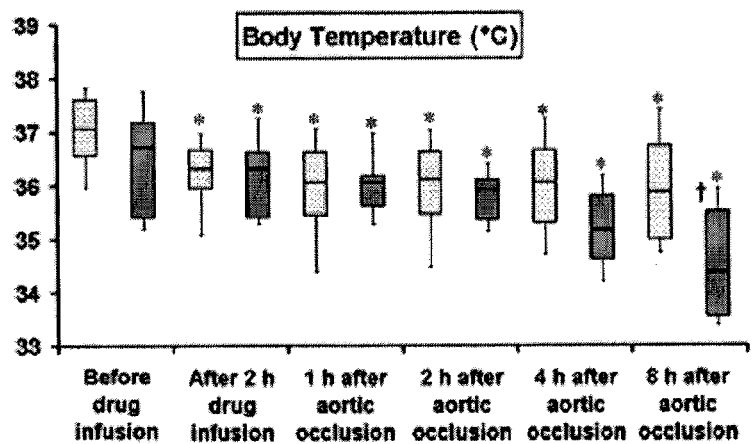

FIG. 22 provides graphs showing carbon dioxide production (FIG. 22A), $O_2$ uptake (FIG. 22B), and body temperature (FIG. 22C) in the vehicle (light bars) and sulfide-treated (dark bars) animals. All data are median (quartiles, range), n=8 in each group. *P<0.05 vs. before drug infusion within each group, †P<0.05 control vs. sulfide.

Figure 23A:
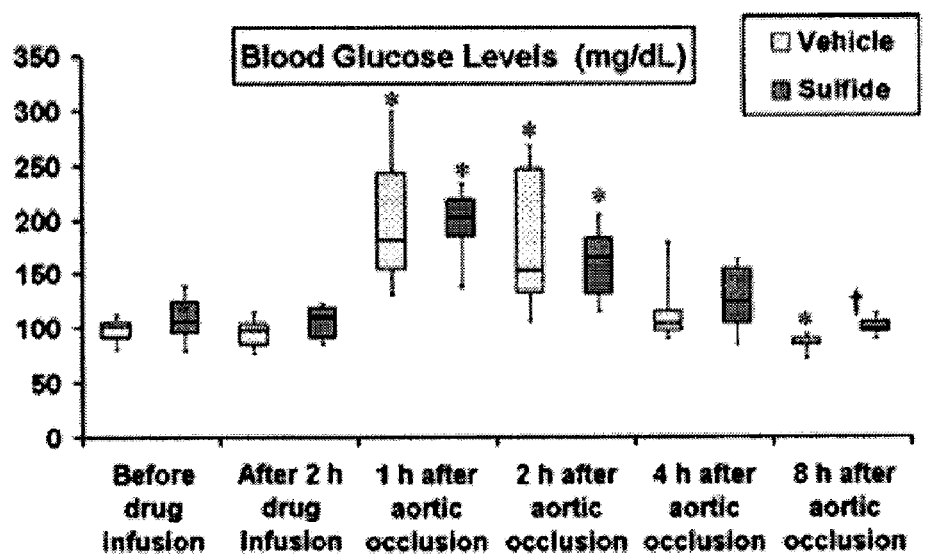
Figure 23B:
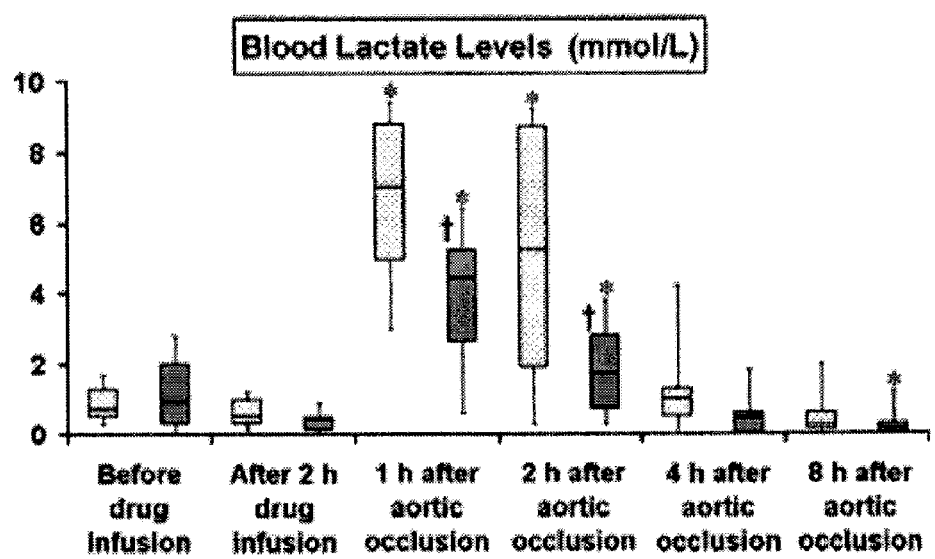

FIG. 23 provides graphs depicting arterial glycemia (FIG. 23A) and lactate (FIG. 23B) levels in the vehicle (light bars) and sulfide-treated (dark bars) animals. All data are median (quartiles, range), n=8 in each group. *P<0.05 vs. before drug infusion within each group, †P<0.05 control vs. sulfide.

DETAILED DESCRIPTION OF THE INVENTION

Compositions comprising a chalcogenide and methods useful in their preparation and use are provided. The compositions are stable, liquid compositions of chalcogenides or chalcogenide compounds or salts or precursors thereof whose effectiveness as a therapeutic is normally compromised during manufacture and storage in liquid as a result of oxidation reactions that produce oxidation products. The liquid compositions of the present invention have increased shelf-life, are easily and reproducibly manufactured, are designed for standard routes of administration, and are advantageous in the treatment and prevention of diseases and conditions where previously liquid or gaseous chalcogenide compositions were considered. The present invention contemplates their use in methods of inducing stasis or pre-stasis in biological material, as well as methods of protecting biological material from disease or injury, particularly ischemic or hypoxic injury.

A. Stable Liquid Pharmaceutical Chalcogenide Compositions

The present invention is directed to stable liquid compositions comprising a chalcogenide and to methods useful in their preparation. For purposes of the present invention, the term "liquid" with regard to pharmaceutical compositions is intended to include the term "aqueous."

In one aspect, the present invention relates to a stable, liquid pharmaceutical composition which comprises a chalcogenide or chalcogenide compound or salt or precursor thereof, wherein the concentration, pH, and oxidation products of said chalcogenide remain within a range of acceptance criteria (numerical limits, ranges, or other criteria for the tests described) after storage of said liquid pharmaceutical composition for a pre-specified time period.

As used herein "stable" refers to the concentration of the active chalcogenide composition, the pH of the chalcogenide composition and/or chalcogenide oxidation products remaining within a range of acceptance criteria.

"Acceptance criteria" refers to the set of criteria to which a drug substance or drug product should conform to be considered acceptable for its intended use. As used herein, acceptance criteria are a list of tests, references to analytical procedures, and appropriate measures, which are defined for a drug product that will be used in a mammal. For example, the acceptance criteria for a stable liquid pharmaceutical composition of chalcogenide refers to a set of predetermined ranges of drug substance, pH, and levels of oxidation products that are acceptable for pharmaceutical use for the specific drug composition based on stability testing. Acceptance criteria may be different for other formulations, include those for topical and cosmetic use. Acceptable standards are generally defined for each industry.

Various acceptance criteria include any value or range described herein that meets Good Manufacturing Practice Regulations promulgated by the US Food and Drug Administration. In certain embodiments, an acceptance criteria is a pH in the range of 7.4-9.0, 6.5 to 8.5, or 6.5 to 9.0 at a time point of 0, 1, 2, 3, or 4 months storage at 4° C., 25° C., or 40° C. In certain embodiments, an acceptance criteria is an osmolality in a range of 250-350 mOsm/kg or an osmolarity in the range of 250-330 mOsm/L at a time point of 0, 1, 2, 3, or 4 months storage at 4° C., 25° C., or 40° C. In certain embodiments, an acceptance criteria is a sulfide concentration of 5.0-6.0 mg/ml at a time point of 0, 1, 2, 3, or 4 months storage at 4° C., 25° C., or 40° C. In another embodiment, an acceptance criteria is a concentration of chalcogenide within the range of 0.1-100 mg/ml, 1-10 mg/ml, or 95-150 mM at a time point of 0, 1, 2, 3, or 4 months storage at 4° C., 25° C., or 40° C. In other embodiments, an acceptance criteria is sulfide present at least 80%, at least 85%, at least 90%, at least 95%, at least 96%, at least 97%, at least 98%, or at least 99% weight/volume of total sulfide and oxidation products thereof at a time point of 0, 1, 2, 3, or 4 months storage at 4° C., 25° C., or 40° C. In related embodiments, oxidation products are present at a concentration less than 10%, less than 5%, less than 4%, less than 3%, less than 2%, less than 1%, 0.5% or less of total sulfide and oxidation products at a time point of 0, 1, 2, 3, or 4 months storage at 4° C., 25° C., or 40° C.

The phrase "pharmaceutically-acceptable" or "pharmacologically-acceptable" refers to molecular entities and compositions that do not produce an allergic or similar unexpected reaction when administered to a human or animal in a medical or veterinary setting.

"Chalcogenide" or "chalcogenide compounds" refers to compounds containing a chalcogen element, i.e., those in Group 6 of the periodic table, but excluding oxides. These elements are sulfur (S), selenium (Se), tellurium (Te) and polonium (Po). Specific chalcogenides and salts thereof include, but are not limited to: $H_2S$, $Na_2S$, NaHS, $K_2S$, KHS, $Rb_2S$, $Cs_2S$, $(NH_4)_2S$, $(NH_4)HS$, BeS, MgS, CaS, SrS, BaS, $H_2Se$, $Na_2Se$, NaHSe, $K_2Se$, KHSe, $Rb_2Se$, $Cs_2Se$, $(NH_4)_2Se$, $(NH_4)HSe$, BeSe, MgSe, CaSe, SrSe, PoSe and BaSe.

"Chalcogenide precursor" refers to compounds and agents that can yield a chalcogenide, e.g., hydrogen sulfide ($H_2S$), under certain conditions, such as upon exposure, or soon thereafter, to biological matter. Such precursors yield $H_2S$ or another chalcogenide upon one or more enzymatic or chemical reactions. In certain embodiments, the chalcogenide precursor is dimethylsulfoxide (DMSO), dimethylsulfide (DMS), methylmercaptan ($CH_3SH$), mercaptoethanol, thiocyanate, hydrogen cyanide, methanethiol (MeSH), or carbon disulfide ($CS_2$). In certain embodiments, the chalcogenide precursor is $CS_2$, MeSH, or DMS.

In one embodiment, $H_2S$ is generated by the spontaneous dissociation of the H2S donor, sodium hydrosulfide (NaHS), in aqueous solution according to the equations:

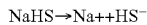

$$NaHS \rightarrow Na^+ + HS^-$$

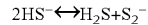

$$2HS^- \leftrightarrow H_2S + S_2^-$$

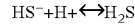

$$HS^- + H^+ \leftrightarrow H_2S$$

In certain embodiments, the chalcogenide compound comprises sulfur, while in others it comprises selenium, tellurium, or polonium. In certain embodiments, a chalcogenide compound contains one or more exposed sulfide groups. In particular embodiments, it is contemplated that this chalcogenide compound contains 1, 2, 3, 4, 5, 6 or more exposed sulfide groups, or any range derivable therein. In particular embodiments, such a sulfide-containing compound is $CS_2$ (carbon disulfide). In certain embodiments, the chalcogenide is a salt, preferably salts wherein the chalcogen is in a −2 oxidation state. Sulfide salts encompassed by embodiments of the invention include, but are not limited to, sodium sulfide ($Na_2S$), sodium hydrogen sulfide (NaHS), potassium sulfide ($K_2S$), potassium hydrogen sulfide (KHS), lithium sulfide ($Li_2S$), rubidium sulfide ($Rb_2S$), cesium sulfide ($Cs_2S$), ammonium sulfide (($NH_4)_2S$), ammonium hydrogen sulfide ($NH_4$)HS, beryllium sulfide (BeS), magnesium sulfide (MgS), calcium sulfide (CaS), strontium sulfide (SrS), barium sulfide (BaS), and the like.

It is well known in the art that sulfides are unstable compounds and many attempts have been made to stabilize this class of compounds. In particular, sulfide oxidation results in oxidation products that may be measured. Thus, the range of oxidation products produced during storage of sulfide in a liquid composition can be readily determined by measuring the levels of oxidation products over time using standard analytical methods that are described herein and well known in the art.

As used herein, "oxidation product" refers to products that result from sulfide chemical transformation, including, e.g., sulfite, sulfate, thiosulfate, polysulfides, dithionate, polythionate, and elemental sulfur. Such products of sulfide oxidation could occur as a result of processing, manufacturing or storage (e.g., by oxidation).

"During storage" refers to the time period after a liquid chalcogenide composition is prepared and prior to its administration to a patient or biological matter. Liquid pharmaceutical compositions of the present invention, once prepared, may not be immediately administered to a subject. Rather, following preparation, it is packaged for storage, either in a liquid form, a semi-solid form, a gelatinous form, a solid form, or other form suitable for administration to a subject. In certain embodiments, storage is in the range of one month to twelve months, one month to six months, or two months to five months.

The compositions of the present invention may be prepared for pharmaceutical administration by methods and with excipients generally known in the art. (*Remington's Pharmaceutical Sciences* (2005); 21$^{st}$ Edition, Troy, David B. Ed. Lippincott, Williams and Wilkins).

Liquid pharmaceutical compositions of the present invention may include a chalcogenide or chalcogenide compound or salt or precursor thereof in any desired concentration. The concentration may be readily optimized, e.g., depending upon the type of biological matter being treated and the route of administration, so as to deliver an effective amount in a convenient manner and over an appropriate time-frame. In some embodiments, the concentration of chalcogenide or chalcogenide compound or salt or precursor thereof is in the range of 0.001 mM to 5,000 mM, in the range of 1 mM to 1000 mM, in the range of 50 to 500 mM, in the range of 75 to 250 mM, or in the range of 95 mM to 150 mM.

The liquid pharmaceutical compositions of the present invention further comprise a chalcogenide consisting of sulfide wherein the concentration of sulfide is in the range 1 mM-250 mM. In another embodiment, the concentration of sulfide is in the range 10 mM-200 mM.

In certain embodiments, the concentration of the chalcogenide or salt or precursor thereof in a liquid chalcogenide composition of the present invention is about, at least about, or at most about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mM or M or more or any range derivable therein (at standard temperature and pressure (STP)). With hydrogen sulfide gas, for example, in some embodiments, the concentration may be from about 0.01 to about 0.5 M (at STP).

Molar concentration may be readily converted into weight per volume. Accordingly, any of the above ranges of molar concentration may be describe in terms of, e.g., mg/ml. Thus, in certain embodiments, the concentration of the chalcogenide or salt or precursor thereof in a liquid chalcogenide composition of the present invention is in the range of 0.01-1000 mg/ml, 0.1-100 mg/ml, or 1-10 mg/ml. In other embodiments, the concentration is approximately or is 1 mg/ml, 2 mg/ml, 3 mg/ml, 4 mg/ml, 5 mg/ml, 6 mg/ml, 7 mg/ml, 8 mg/ml, 9 mg/ml, or 10 mg/ml.

In one aspect of the current invention, liquid pharmaceutical compositions comprise a chalcogenide or chalcogenide compound or salt or precursor thereof dissolved in a liquid. In one embodiment, the liquid is water ($H_2O$), while in other embodiments it is a more physiologically compatible solution such as phosphate-buffered saline (PBS) or Ringer's solution. In further embodiments, the liquid is sodium hydroxide in water, or potassium hydroxide in water.

It is contemplated that in some embodiments, a liquid pharmaceutical composition is a saturated solution with respect to the chalcogenide or chalcogenide compound or salt or precursor thereof.

As used herein, the term "%" when used without qualification (as with w/v, v/v, or w/w) means % weight-in-volume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w) (*Remington's Pharmaceutical Sciences* (2005); 21$^{st}$ Edition, Troy, David B. Ed. Lippincott, Williams and Wilkins).

In one embodiment, the liquid pharmaceutical compositions of the present invention comprise sulfide measured at 80%-100% (w/v). In one embodiment, liquid pharmaceutical compositions of the present invention comprise sulfide measured at 90%-100% (w/v). In one embodiment, liquid pharmaceutical compositions of the present invention comprise sulfide measured at 95%-100% (w/v). In one embodiment, liquid pharmaceutical compositions of the present invention comprise sulfide measured at 98%-100% (w/v).

In one embodiment, the pH of a liquid pharmaceutical chalcogenide composition of the present invention is in the range of (3.0-12.0), while in other embodiments, the pH in the range of (5.0-9.0). The pH of the liquid pharmaceutical composition may be adjusted to a physiologically compatible range. For example, in one embodiment, the pH of the liquid pharmaceutical composition is in the range of 6.5-8.5. In other embodiments, the liquid pharmaceutical compositions of the present invention have a pH in the range of 7.5-8.5 or 7.4-9.0.

In one embodiment, oxygen is measured in the range of 0 $\mu$M-5 $\mu$M in the pharmaceutical composition. In one embodiment, oxygen is measured in the range of 0 $\mu$M-3 $\mu$M in the pharmaceutical composition. In one embodiment, oxygen is measured in the range of 0.01 $\mu$M-1 $\mu$M in the pharmaceutical composition. In one embodiment, oxygen is measured at 0.001 $\mu$M-1 $\mu$M in the pharmaceutical composition.

The pharmaceutical composition of the present invention may further comprise oxidation products. Oxidation products of the present invention include, but are not limited to, sulfite, sulfate, thiosulfate, polysulfides, dithionate, polythionate, and elemental sulfur. In various embodiments, one or more of these oxidation products is present in an amount less than 10%, less than 6.0%, less than 3.0%, less than 1.0%, less than 0.5%, less than 0.2%, less than 0.1%, less than 0.05%, or less than 0.01%.

In one embodiment, the oxidation product, sulfite, is present in the range of 0%-10% (w/v). In one embodiment, the oxidation product, sulfite, is in the range of 3.0%-6.0% (w/v). In one embodiment the oxidation product, sulfite, is in the range of 1.0%-3.0% (w/v). In one embodiment, the oxidation product, sulfite, is in the range of 0%-1.0% (w/v).

In one embodiment, the oxidation product, sulfate, is present in the range of 0%-10.0% (w/v). In one embodiment, the oxidation product, sulfate, is in the range of 3.0%-6.0% (w/v). In one embodiment, the oxidation product, sulfate, is in the range of 1% to 3.0% (w/v). In one embodiment, the oxidation product, sulfate, is in the range of 0%-1.0% (w/v).

In one embodiment, the oxidation product, thiosulfate, is present in the range of 0%-10% (w/v). In another embodiment, the oxidation product, thiosulfate, is in the range of 3.0%-6.0% (w/v). In another embodiment, the oxidation product, thiosulfate, is in the range of 1.0%-3.0% (w/v). In another embodiment, the oxidation product, thiosulfate, is in the range of 0%-1.0% (w/v).

In one embodiment, the oxidation products include polysulfides present in the range of (0%-10% (w/v). In one embodiment, the oxidation products, polysulfides, are in the range of 3.0%-6.0% (w/v). In one embodiment the oxidation products, polysulfides, are in the range of 1.0%-3.0% (w/v). In one embodiment, the oxidation products, polysulfides, are in the range of 0%-1.0% (w/v).

In one embodiment, the oxidation product, dithionate, is present in the range of 0%-10% (w/v). In one embodiment, the oxidation product, dithionate, is in the range of 3.0%-6.0% (w/v). In one embodiment the oxidation product, dithionate, is in the range of 1.0%-3.0% (w/v). In one embodiment, the oxidation product, dithionate, in the range of 0%-1.0% (w/v).

In one embodiment, the oxidation product, polythionate, is present in the range of 0%-10% (w/v). In one embodiment, the oxidation product, polythionate, is in the range of 3.0%-6.0% (w/v). In one embodiment the oxidation product, polythionate, is in the range of 1.0%-3.0% (w/v). In one embodiment, the oxidation product, polythionate, is in the range of 0%-1.0% (w/v).

In one embodiment, the oxidation product, elemental sulfur, is present in the range of 0%-10% (w/v). In one embodiment, the oxidation product, elemental sulfur, is in the range of 3.0%-6.0% (w/v). In one embodiment the oxidation product, elemental sulfur, is in the range of 1.0%-3.0% (w/v). In one embodiment, the oxidation product, elemental sulfur, is present in the range of 0%-1.0% (w/v).

Those skilled in the art will recognize that a liquid pharmaceutical composition (drug product) preferably remain stable during storage prior to administration to a mammal. In one embodiment, storage of the liquid pharmaceutical composition is about three months, and the storage temperature is in the range of 18° C.-27° C. In another embodiment, storage of the liquid pharmaceutical composition is about six months, and the storage temperature is in a range of 18° C.-27° C. In another embodiment, storage of the liquid pharmaceutical composition is about twelve months, and the storage temperature is in a range of 18° C.-27° C.

In one embodiment, storage of the liquid pharmaceutical composition is about three months, and the storage temperature is in a range of 4° C.-23° C. In another embodiment, storage of the liquid pharmaceutical composition is about six months, and the storage temperature is in a range of 4° C.-23° C. In another embodiment, storage of the liquid pharmaceutical composition is about twelve months, and the storage temperature is in a range of 4° C.-23° C.

In one embodiment, methods of preparing liquid pharmaceutical compositions of the present invention further comprise adjusting the osmolarity of the liquid pharmaceutical composition to an osmolarity in the range of 200-400 mOsmol/L. In one embodiment, the osmolarity of the liquid pharmaceutical composition is in the range of 240-360 mOsmol/L or an isotonic range. In particular embodiments, the osmolarity of the liquid pharmaceutical composition is in the range of 250-330 mOsmol/L or the osmolality of the compositions is in the range of 250-350 mOsm/kg. NaCl may be used as an excipient to adjust osmolality.

In certain embodiments, isotonicity of liquid pharmaceutical compositions is desirable as it results in reduced pain upon administration and minimizes potential hemolytic effects associated with hypertonic or hypotonic compositions. Thus, the stabilized compositions of the invention not only have increased storage stability, but also have the added benefit of substantially reduced pain upon administration when compared with formulations using other more traditional buffer systems consisting of an acid and a salt form of the acid.

In one embodiment, the stable liquid pharmaceutical composition is packaged in an impermeable container. "Impermeable container" refers to containers that provide a permanent barrier to the passage of gas molecules. Impermeable containers are known to those skilled in the art and include, but are not limited to, "i.v. bags" comprising a gas impermeable construction material, or a sealed glass vial. The liquid pharmaceutical composition may be packaged into an impermeable container an inert atmosphere or noble gas. Noble gas refers to helium (He), neon (Ne), argon (Ar), krypton (Kr), xenon (Xe), and radon (Rn). Inert gas refers to nitrogen ($N_2$). The term "inert atmosphere" refers to a nitrogen or argon atmosphere in a container. The liquid pharmaceutical composition may be packaged in light-protective vials or containers, e.g., amber vials. In one embodiment, the composition may be sealed and stored in a glass ampoule.

In some embodiments, liquid pharmaceutical compositions of the present invention comprise one or more excipients included to prevent oxidation of the chalcogenide during storage, where storage is in the range of one to twelve months or longer. In some embodiments, storage is in the range of one to six months. In some embodiments, storage is in the range of three to six months. In some embodiments, storage is in the range of four to five months. Embodiments of the present invention may use a single excipient or a combination of excipients. There are many suitable excipients. Examples include chelators, pH modifying agents, reducing agents, antioxidants, spin-trap agents and preservatives.

In one embodiment, liquid pharmaceutical compositions of the present invention may optionally contain chelators or chelating agents. A chelate is a water-soluble complex between a metal ion and a complexing agent. It usually does not dissociate easily in solution, but forms an inert complex. In labile complexes, however, the metal ion can be readily exchanged. Metal complexes of transition elements are well known, but chelation occurs within a much wider range of elements. Chelating agents yielding soluble metal complexes are also called sequestering agents. A chelating agent typically has at least two functional groups that donate a pair of electrons to the metal, such as —O, —$NH_2$ or —$COO^-$. Furthermore, these groups are located so as to allow ring formation with the metal. Examples of naturally-occurring chelators include carbohydrates, including polysaccharides, organic acids with more than one coordination group, lipids, steroids, amino acids and related compounds, peptides, phosphates, nucleotides, tetrapyrrols, ferrioxamines, ionophores, such as gramicidin, monensin, valinomycin, and phenolics. Examples of synthetic chelators include, but are not limited to, Diethylenetriaminepentaacetic acid (DTPA), Diethylenetriaminepentaacetic acid pentasodium salt (DTPA5), CaDTPAH, dimercaprol (BAL), deferoxamine, desferal, 2,2'-Bipyridyl DimercaptopropanolEthylenediaminetetraacetic acid, Ethylenedioxy-diethylene-dinitrilo-tetraacetic acid (EDTA), CaNa$_2$ethylenediaminetetraacetic acid, Ethylene glycol-bis-(2-aminoethyl)-N,N,N',N'-tetraacetic acid (EGTA), ionophores, Nitrilotriacetic acid (NTA), ortho-Phenanthroline, Salicylic acid, succimer (meso-2,3-dimercaptosuccinic acid, (DMSA), Triethanolamine (TEA), N-(2-Hydroxyethyl)ethylenediamine-N,N',N'-triacetic acid Trisodium salt (HEDTA), Nitrilotriacetic acid (NTA).

In one embodiment, the synthetic chelator is DTPA. In certain embodiments, the concentration of DTPA is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M or any range derivable therein. In one embodiment, the DTPA is in the range of 0.1 mM to 50 mM. In one embodiment, the synthetic chelator consists of DTPA5. In certain embodiments, the concentration of DTPA5 is in the range of (0.0001%-0.1%) (w/v). In another embodiment, DTPA5 is in the range of (0%-1.0%) (w/v). In one embodiment, DTPA5 is in the range of (0% to 0.01%) (w/v).

In one embodiment, the synthetic chelator is CaDTPA. In certain embodiments, the concentration of CaDTPA is in the range of (0.0001%-0.1%) (w/v). In one embodiment, CaDTPA is in the range of (0% to 0.01%) (w/v).

In another embodiment, CaDTPA is in the range of (0%-1.0%) (w/v).

In one embodiment, the synthetic chelator is deferoxamine. In certain embodiments, the concentration of deferoxamine is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein. In one embodiment, the deferoxamine is in the range of 0.1 mM to 10 mM.

In one embodiment, the synthetic chelator is EDTA. In certain embodiments, the concentration of EDTA is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein. In a certain embodiment, EDTA is in the range of 0%-1% (w/v). In another embodiment, EDTA is in the range of 0.0001%-0.1% (w/v). In another embodiment, EDTA is in the range of 0%-1.0% (w/v). In one embodiment, EDTA is in the range of 0% to 0.01% (w/v).

Liquid pharmaceutical compositions of the present invention may further comprise one or more pH modifying agents. pH modifying agents, include, but are not limited to, inorganic salts, such as zinc carbonate, magnesium carbonate, calcium carbonate, magnesium hydroxide, calcium hydrogen phosphate, calcium acetate, calcium hydroxide, calcium lactate, calcium maleate, calcium oleate, calcium oxalate, calcium phosphate, magnesium acetate, magnesium hydrogen phosphate, magnesium phosphate, magnesium lactate, magnesium maleate, magnesium oleate, magnesium oxalate, sodium chloride, sodium carbonate, sodium bicarbonate, potassium hydroxide, potassium phosphate, sodium bicarbonate, thioglycolic acid, zinc acetate, zinc hydrogen phosphate, zinc phosphate, zinc lactate, zinc maleate, zinc oleate, zinc oxalate, and combinations thereof. Other pH modifying agents include, e.g., acetic acid, fumaric acid, malic acid, nitric acid, phosphoric acid, propionic acid, sulfuric acid, tartaric acid, carbon dioxide, carbonic acid, N-methyl-D-glucamine, 4-(2-hydroxyethyl)-morpholine, Tromethamine, Orotic acid, and hydrochloric acid. In one embodiment, the pH modifying agent is sodium hydroxide.

It is understood by one skilled in the art that a pH modifying agent may serve as a buffering agent when it is added to an already acidic or basic solution, which it then modifies and maintains at a new pH (see: *The United States Pharmacopeia—National Formulary 29$^{th}$ Edition*, (2006) Rockville, Md.; Stahl, P. Wermuth, C. ed. *Handbook of Pharmaceutical Salts Properties*, Selection and Use. Wiley (2002)). In a particular embodiment, the pH modifying agent serves as a buffering agent and consists of carbon dioxide or hydrogen sulfide.

In certain embodiments, pharmaceutical compositions of the present invention include one more excipients that are reducing agents, such as, e.g., glutathione (see: U.S. Pat. No. 6,586,404), tris(2-carboxyethyl) phosphine hydrochloride (TSEP), I-cysteine, cysteine or methionine. In one embodiment, the reducing agent is glutathione (see: Vincent et al., *Endocrine Reviews* (2004) 25:612-628), dithiothreitol (DTT) (Weir et al., *Respir and Physiol Biol*; (2002) 132:121-30) or dithioerythritol (DTE). In certain embodiments, the concentration of glutathione is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M or more or any range derivable therein. In certain embodiments, the concentration of dithiothreitol (DTT), which present at about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein. In certain embodiments, the reducing agent is dithioerythritol (DTE), is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein.

Liquid pharmaceutical compositions of the present invention may optionally comprise a free radical scavenger or antioxidant. Examples of free radical scavengers or antioxidants include, but are not limited to, ascorbic acid (vitamin C), D-alpha tocopherol acetate, DL-alpha-tocopherol (vitamin E), melatonin, sodium bisulfite, sodium sulfite, sodium metabisulfite, Trolox (6-hydroxy-2,5,7,8-tetramethyl chroman-2-carboxylic acid), Tris(2-Carboxyethyl) phosphine Hydrochloride (TCEP), melatonin, dithionite, pyrosulfite, cysteine, potassium disulfite, sodium thioglycolate, thioethylene glycol, L-threoascobic acid, acetylsalicylic acid, salicylic acid, lecithin, ascorbyl palmitate, butylated hydroxyanidole, ascorbic acid, butylated hydroxyanisole, butylated hydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, lecithin, ethanolamine, meglumine and combinations thereof (see US 2005/0106214).

In one embodiment, the anti-oxidant, e.g., sodium sulfite, is in the range of 0%-2% (w/v). In one embodiment, the anti-oxidant, e.g., sodium sulfite, is in the range of 0%-1% (w/v). In one embodiment, the anti-oxidant, e.g., sodium sulfite, is in the range of 0%-0.2% (w/v). (see: Swadesh et al., *Anal Biochem* (1984), 141:397).

In one embodiment, the anti-oxidant agent is a spin-trap agent. Examples of spin-trap agents include, but are not limited to, N-t-butyl-phenylnitrone (PBN) (see: Kotake, Y., *Antioxid Redox Signal* (1999) 481), 4-Hydroxy-2,2,6,6-tetramethylpiperidine-1-oxyl (TEMPOL) (Gariboldi, M. B., et al. (2000), *Free Radic. Biol. Med.* 29:633; Miura, Y., et al. *J. Radiat. Res.* (Tokyo) (2000) 41:103; Mota-Filipe, H., et al. (1999), *Shock* 12:255R: 22-41; S: 39-26 2,2,6,6-tetramethylpiperidine-N-oxyl (TEMPO) (see: Lapchak, et al., *Stroke* (2001) 32:147-53); (disodium-[(tert-butylimino) methyl] benzene-1,3-disulfonate N-oxide (NXY-059) (see: Lapchak et al., *CNS Drug Rev* (2003) 9:253-62).

In some embodiments, the spin-trap agent is TEMPO, which is present in the range of 0 mg/kg-1,000 mg/kg. In some embodiments, the spin-trap agent is TEMPO and is present in the range of 100 mg/kg-1,000 mg/kg. In another embodiment, the spin-trap agent is TEMPO and is present in the range of 0 mg/kg-100 mg/kg.

Chalcogenide compositions of the present invention may optionally comprise preservatives. As used herein, the term "preservative" is intended to mean a compound used to prevent the growth of microorganisms. Such compounds by way of example and without limitation, include benzalkonium chloride, benzethonium chloride, benzoic acid, benzyl alcohol, butylated hydroxyanisole (BHA), cetrimonium bromide, cetylpyridinium chloride, chlorobutanol, chlorocresol, cresol, methylparaben sodium, phenol, pheenoxyethanol, phenylethyl alcohol, phenylmercuric acetate, phenylmercuric nitrate, phenylmercuric acetate, thimerosal, metacresol, myristylgamma picolinium chloride, potassium benzoate, potassium sorbate, sodium benzoate, sodium propionate, sorbic acid, thioglycerol, thimerosal, thymol, and methyl, ethyl, propyl or butyl parabens and others known to those of ordinary skill in the art. Such preservatives are used in liquid chalgogenide compositions at typical concentrations in accordance with acceptable pharmaceutical practices, such as described. (see: *The United States Pharmacopeia—National Formulary* 29$^{th}$ Edition, (2006) Rockville, Md.; *Remington's Pharmaceutical Sciences* (2005) 21$^{st}$ Edition, Troy, D B, Ed. Lippincott, Williams and Wilkins). In a certain embodiment, the preservative is benzyl alcohol and is present in the range of 0%-1.0% (w/v). In one embodiment, the preservative is benzyl alcohol and is present in the range of 0%-0.5% (w/v). In one embodiment, the preservative is phenol in the range of 0%-0.5% (w/v). In a certain embodiment, the preservative is methyl paraben in the range of (0.0%-0.25% (w/v). In a certain embodiment, the preservative is ethyl paraben in the range of 0%-0.25% (w/v). In a certain embodiment, the preservative is propyl paraben in the range of 0%-0.25% (w/v). In a certain embodiment, the preservative is butyl paraben, in the range of 0%-0.4% (w/v). In a certain embodiment, the preservative is benzalkonium chloride in the range of 0%-0.02% (w/v).

In one embodiment, a combination of excipients reduces polysulfide formation. In one embodiment, the combination of excipients that reduce polysulfide formation comprises sodium sulfite in the range of 0%-0.1% (w/v) and EDTA in the range of 0%-0.01% (w/v). In one embodiment, the combination of excipients that reduce polysulfide formation are sodium sulfite and DTPA5. In one embodiment, the combination of excipients that reduce polysulfide formation are sodium sulfite, DTPA5 and benzyl alcohol.

In particular embodiments, formulations of the present invention include less than or equal to 0.01 mg/ml iron, less than or equal to 10, 5, 2.7, 2.5, or 1 EU/ml endotoxin, less than 10, 5, or 1 ppm carbonyl sulfide, and less than 5, 2.5, or 1 ppm carbon disulfide.

Certain of the above are preferred since these materials are widely accepted as food additives and processing aids and have achieved "Generally Recognized as Safe" (or "GRAS") status with the U.S. Food and Drug Administration for such applications.

The present invention further includes kits comprising liquid pharmaceutical compositions of the present invention. In certain embodiments, such kits comprise one or more containers to store the liquid pharmaceutical compositions of the present invention. In one embodiment, the composition is stored in the container under an inert or noble gas and the container is a sealed and has and impermeable light-protective container (e.g., an amber vial).

B. Methods of Preparing Liquid Pharmaceutical Compositions

According to various embodiments of the methods of the present invention, a biological material is provided with a liquid pharmaceutical composition of the invention, e.g., intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, intraocularly, subcutaneously, subconjunctival, intravesicularly, mucosally, intrapericardially, intraumbilically, intraocularally, orally, topically, locally, by injection, by infusion, by continuous infusion, by absorption, by adsorption, by immersion, by localized perfusion, via a catheter, or via a lavage.

A composition containing a known and desired concentration of a chalcogenide or salt or precursor thereof dissolved in a liquid or a composition for parenteral administration is contemplated. "Parenteral" refers to any route of administration of a substance other than via the digestive tract. In general, a liquid chalcogenide composition may be produced by, for example, by contacting (e.g., dissolving or infusing) a chalcogenide gas (e.g., $H_2S$) into the composition to cause the gas molecules to dissolve in a liquid comprised of an appropriate pH modifying agent. In one embodiment, the chalcogenide gas is a buffering agent and is dissolved in a liquid comprised of a pharmaceutically acceptable carrier. In a further embodiment, the liquid pharmaceutical composition is comprised of a chalcogenide gas solution prepared as described with the addition of a single excipient or a combination of excipients.

Those skilled in the art will recognize that the amount of gas that dissolves in the composition will depend on a number of variables including, but not limited to, the solubility of the gas in the liquid or solution, the chemical composition of the liquid or solution, its temperature, its pressure, its pH, the pKA of the chemicals in its composition, its ionic strength, as well as the concentration of the gas and the extent of contacting the gas into the solution (e.g., rate of and duration of dissolving or infusing). The concentration of the chalcogenide or salt or precursor thereof in the liquid or solution for parenteral administration can be determined using methods known to those skilled in the art. The stability of the chalcogenide or salt or precursor thereof can be determined by measuring its concentration after varying intervals of time following preparation or manufacture of the liquid chalcogenide composition, where a decrease in the concentration of the chalcogenide or salt or precursor thereof compared to the starting concentration is indicative of loss of or chemical conversion of the chalcogenide or salt or precursor thereof.

Alternatively, the stability of the liquid chalcogenide pharmaceutical composition can be determined by measuring the change, over time, under controlled storage conditions (e.g., temperature, humidity, light exposure), of chemical entities that are produced by chemical transformation (e.g., oxidation) of the most abundant chalcogenide compound (or salt or precursor thereof).

In some embodiments, a liquid chalcogenide composition is produced by dissolving a salt form of the chalcogenide into sterile water or saline (0.9% sodium chloride) to yield a pharmaceutically acceptable parenteral formulation (e.g., intravenous, intra-arterial, subcutaneous, intramuscular, intracisternal, intraperitoneal, and intradermal) dosage form. In another embodiment, liquid pharmaceutical compositions are formulated for oral, nasal (inhalation or aerosol), buccal, or topical administration dosage forms. The parenteral liquid dosage form may be buffered to a certain pH to enhance the solubility of the chalcogenide compound or to influence the ionization state of the chalcogenide compound. In the case of hydrogen sulfide or hydrogen selenide, any of a number of salt forms known to those skilled in the art may suffice, including, but not limited to, sodium, calcium, barium, lithium, or potassium. In one embodiment, sodium sulfide or sodium selenide is dissolved in sterile phosphate buffered saline and the pH is adjusted to a range of 7.5-8.5 with hydrochloric acid to yield a solution of known concentration which can be administered to a subject.

In various embodiments, the liquid chalcogenide composition is prepared in a liquid or solution in which the oxygen has been reduced prior to contacting the liquid or solution with the chalcogenide compound. In one embodiment, methods of preparing liquid pharmaceutical compositions of the present invention further comprise limiting oxygen content in each aspect of manufacturing and storage of the pharmaceutical composition. In one embodiment, oxygen is measured in the range of 0 $\mu$M-5 $\mu$M in the pharmaceutical composition. In one embodiment, oxygen is measured in the range of 0 $\mu$M-3 $\mu$M in the pharmaceutical composition. In one embodiment, oxygen is measured in the range of 0.001 $\mu$M-0.1 $\mu$M in the pharmaceutical composition. In one embodiment, oxygen is measured in the range of 0.1 $\mu$M-1 $\mu$M in the pharmaceutical composition.

Certain chalcogenide compounds (e.g., hydrogen sulfide, hydrogen selenide), are not stable in the presence of oxygen due to their ability to react chemically with oxygen, leading to their oxidation and chemical transformation. Accordingly, oxygen may be removed from liquids or solutions using methods known in the art, including, but not limited to, application of negative pressure (vacuum degasing) to the liquid or solution, or contacting the solution or liquid with a reagent which causes oxygen to be bound or "chelated", effectively removing it from solution.

In one embodiment, the liquid chalcogenide composition is stored in an impermeable container. This is particularly desirable when the oxygen has previously been removed from the solution to limit or prevent oxidation of the chalcogenide or salt or precursor thereof. Additionally, storage in an impermeable container will inhibit the oxidation products of the chalcogenide gas from the liquid or solution, allowing a constant concentration of the dissolved chalcogenide to be maintained. Impermeable containers are known to those skilled in the art and include, but are not limited to, "i.v. bags" comprising a gas impermeable construction material, or a sealed glass vial. To prevent exposure to air in the gas-tight storage container, an inert or noble gas, such as nitrogen or argon, may be introduced into the container prior to closure.

In other related embodiments, liquid pharmaceutical compositions are stored in a light-resistant or a light-protective container or vial, such as an amber vial. The composition is preferably packaged in a glass vial. It is preferably filled to a slight over-pressure in an inert atmosphere, e.g., nitrogen, to prevent/slow oxidative breakdown of the composition, and is contained in a form such that ingress of light is prevented, thereby preventing photochemical degradation of the composition. This may be most effectively achieved using an amber vial. Container systems that permit a solution to be stored in an oxygen-free environment are well known as many intravenous solutions are sensitive to oxygen. For example, a glass container that is purged of oxygen during the filling and sealing process may be used. In another embodiment, flexible plastic containers are available that may be enclosed in an overwrap to seal against oxygen. Basically, any container that prevents oxygen from interacting with the liquid pharmaceutical composition may be used. (see: U.S. Pat. No. 6,458,758)

In one embodiment, the container includes one or more oxygen scavenger. For example, the oxygen scavenging composition can be applied as a coating or lining upon the inside surface of the product supporting or retaining means to function as a barrier to oxygen permeation (see: U.S. Pat. No. 5,492,742).

In one embodiment, the present invention includes a method of preparing a pharmaceutical composition comprising dissolving a chalcogenide salt in a liquid solution. In one embodiment, the chalcogenide salt is sodium sulfide. In another embodiment, the chalcogenide and salt include, but are not limited to $H_2S$, $Na_2S$, NaHS, $K_2S$, KHS, $Rb_2S$, $CS_2S$, $(NH_4)_2S$, $(NH_4)HS$, BeS, MgS, CaS, SrS, BaS. In one embodiment, the liquid is water or phosphate buffered saline. In one embodiment, the liquid is potassium hydroxide solution or a sodium hydroxide solution.

In another embodiment, the present invention includes a method of preparing a pharmaceutical composition comprising infusing a gaseous form of a chalcogenide, e.g., $H_2S$ (hydrogen sulfide), into a liquid. In one embodiment, the liquid is potassium hydroxide solution or a sodium hydroxide solution.

In various embodiments, methods of preparing liquid pharmaceutical compositions comprising a chalcogenide of the present invention further include the step of adjusting the pH of the composition. In certain embodiments, the pH is adjusted by the addition of one or more of hydrogen chloride, carbon dioxide, nitrogen, or hydrogen sulfide. In another embodiment, the pH is adjusted by dissolving nitrogen, carbon dioxide, or hydrogen sulfide into the composition or any combination thereof. In one embodiment, pH is adjusted by dissolving a combination of nitrogen and carbon dioxide or a combination of nitrogen and hydrogen sulfide into the composition. In certain embodiments, the pH of the solution is adjusted by dissolving hydrogen sulfide into sodium hydroxide, or potassium hydroxide. In one embodiment, one equivalent of hydrogen sulfide solution is dissolved into one equivalent of sodium hydroxide solution.

In addition, the methods described herein may further include the addition of one or more of a metal chelator, a free radical scavenger, and/or a reducing agent. In the particular method of the present invention, the liquid chalcogenide composition is manufactured in a sealed container that contains a vessel to hold the liquid chalcogenide composition with access ports for pH measurement, addition of gasses, and dispensing without contact to the outside atmosphere. In one embodiment, the vessel is a three neck flask with ground glass fittings. In one embodiment, the vessel is flushed with nitrogen gas or argon gas to minimize oxygen content to a range of 0.00 $\mu$M-3 $\mu$M. In a certain embodiment, oxygen content in the vessel is measured at 0.01 $\mu$M-0.03 $\mu$M. The final sulfide concentration of the liquid chalcogenide composition is determined by the initial concentration of NaOH. For example, NaOH solution is placed in the three neck flask with any desired additives to enhance stability (DTPA) or to balance osmolarity (NaCl). The solution is deoxygenated by dissolving with argon at 5 psi for 15 minutes while stirring. Hydrogen sulfide gas ($H_2S$) is dissolved in the solution while stirring until the pH of the solution is in the range of 7.6 and 7.8. In one embodiment, an acceptable pH range is between 7.5 and 8.0. The solution is dispensed from the flask under positive argon pressure into vials or bottles by filling the headspace with argon to the maximum to prevent oxygen to enter the solution. The dispensing vials or bottles are placed in a glove box that is flushed with a constant stream of argon to minimize oxygen to a range of 0.00 $\mu$M-0.5 $\mu$M and each bottle or vial is flushed with argon before dispensing. The vials and bottles are made of amber glass to enhance stability and are closed with caps lined with Teflon lined silicon or rubber sealed with plastic caps and using a crown-cap crimper to provide an air-tight seal. In one embodiment, the vials and bottles are comprised of borosilicate glass. In one embodiment, the vials and bottles are comprised of silicon dioxide.

C. Methods of Using Liquid Pharmaceutical Composition

The liquid pharmaceutical compositions of the present invention may be used to treat or prevent a variety of diseases and disorders, including any disease or disorder that has been treated using a gaseous form of a chalcogenide (see; WO 2005/041655) or a liquid chalcogenide composition. For example, treatment with sodium sulfide has been used in an animal model as a potential treatment for myocardial infarction, sepsis (see: Hui, et al. *J Infect* (2003):47:155), vascular abnormalities in cirrhosis (see: Fiorucci S, et al., *Hepatology*. (2005) 42:539), as a cardioprotectent (see: (see; Geng, et al., Biochem and Biophy Res Com (2004) 313:362), as a neuroprotectant (see: Qu K. et al, *Stroke*. (2006) 889) in myocardial ischemia reperfusion injury (see: Johansen et al., Basic Res Cardiol (2006) 101: 53), to reduce vascular calcification (see: Wu et al., Acta Pharmacol Sin. (2006) 27:299), to reduce gastric injury induced by drug treatment (see: Fiorucci, S. et al., *Gastroenterology* (2005) 129:1210), to reduce neutrophil adhesion and to modulate leukocyte-mediated inflammation (see: Zanardo et al., FASEB J. (2006) 20: 2118-2120), in erectile dysfunction (see: Srilatha B. et al., *Eur J Pharmacol*. (2006) 535:280), irritable bowel syndrome (Distrutti E., et al., JPET (2006) 319:447) and for anti-nociceptive effects in post-inflammatory hypersensitivity. Additional examples of therapeutic uses and related information are summarized in Table I. In addition, the compositions may be used to induce stasis or pre-stasis in a variety of biological matter and may also be used to treat or prevent injury resulting from ischemia or hypoxia.

The term "biological matter" refers to any living biological material, including cells, tissues, organs, and/or organisms, and any combination thereof. It is contemplated that the methods of the present invention may be practiced on a part of an organism (such as in cells, in tissue, and/or in one or more organs), whether that part remains within the organism or is removed from the organism, or on the whole organism. Moreover, it is contemplated in the context of cells and tissues that homogenous and heterogeneous cell populations may be the subject of embodiments of the invention. The term "in vivo biological matter" refers to biological matter that is in vivo, i.e., still within or attached to an organism. Moreover, the term "biological matter" will be understood as synonymous with the term "biological material." In certain embodiments, it is contemplated that one or more cells, tissues, or organs is separate from an organism. The term "isolated" can be used to describe such biological matter. It is contemplated that the methods of the present invention may be practiced on in vivo and/or isolated biological matter.

A cell treated according to the methods of the present invention may be eukaryotic or prokaryotic. In certain embodiments, the cell is eukaryotic. More particularly, in some embodiments, the cell is a mammalian cell. Mammalian cells include, but are not limited to those from a human, monkey, mouse, rat, rabbit, hamster, goat, pig, dog, cat, ferret, cow, sheep, or horse. Moreover, cells of the invention may be diploid, but, in some cases, the cells are haploid (sex cells). Additionally, cells may be polyploid, aneuploid, or anucleate. The cell can be from a particular tissue or organ, such as heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord. In certain embodiments, the cell can be characterized as one of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

The terms "tissue" and "organ" are used according to their ordinary and plain meanings. Though tissue is composed of cells, it will be understood that the term "tissue" refers to an aggregate of similar cells forming a definite kind of structural material. Moreover, an organ is a particular type of tissue. In certain embodiments, the tissue or organ is "isolated," meaning that it is not located within an organism.

The terms "hypoxia" and "hypoxic" refer to an environment with levels of oxygen below normal. Hypoxia occurs when the normal physiologic levels of oxygen are not supplied to a cell, tissue, or organ. "Normoxia" refers to normal physiologic levels of oxygen for the particular cell type, cell state or tissue in question. "Anoxia" is the absence of oxygen. "Hypoxic conditions" are those leading to cellular, organ or organismal hypoxia. These conditions depend on cell type, and on the specific architecture or position of a cell within a tissue or organ, as well as the metabolic status of the cell. For purposes of the present invention, hypoxic conditions include conditions in which oxygen concentration is at or less than normal atmospheric conditions, that is less that 20.8, 20, 19, 18, 17, 16, 15, 14, 13, 12, 11, 10, 9, 8, 7, 6, 5, 4, 3, 2, 1, 0.5, 0%. Alternatively, these numbers could represent the percent of atmosphere at 1 atmosphere of pressure (101.3 kPa). "Anoxia" is the absence of oxygen. An oxygen concentration of zero percent defines anoxic conditions. Thus, hypoxic conditions include anoxic conditions, although in some embodiments, hypoxic conditions of not less than 0.5% are implemented. As used herein, "normoxic conditions" constitute oxygen concentrations of around 20.8% or higher.

At standard temperatures and pressure (STP), water exposed to air comprises 280 μM dissolved oxygen. In certain embodiments, "formulation hypoxia" occurs when the liquid pharmaceutical chalcogenide composition is formulated in water and oxygen levels in the water are reduced to hypoxic conditions, i.e., oxygen in water is reduced below 280 μM using methods described herein and known to one skilled in the art.

In another embodiment, formulation hypoxia include conditions in which oxygen concentration is at or less than normal atmospheric conditions, that is less that 20.8, 20, 19, 18, 17, 16, 15, 14, 13, 12, 11, 10, 9, 8, 7, 6, 5, 4, 3, 2, 1, 0.5, 0%; or alternatively, these numbers could represent the percent of atmosphere at 1 atmosphere of pressure (101.3 kPa).

Standard methods of achieving hypoxia or anoxia are well established and include using environmental chambers that rely on chemical catalysts to remove oxygen from the chamber. Such chambers are available commercially from, for example, BD Diagnostic Systems (Sparks, Md.) as GASPAK Disposable Hydrogen+Carbon Dioxide Envelopes or BIO-BAG Environmental Chambers. Alternatively, oxygen may be depleted by exchanging the air in a chamber with a non-oxygen gas, such as nitrogen. Oxygen concentration may be determined, for example using a FYRITE Oxygen Analyzer (Bacharach, Pittsburgh Pa.).

In one embodiment, the term "effective amount" refers to the amount that can achieve a measurable result. In one embodiment, an "effective amount" is, for example, an amount that when administered to a human subject in need of medical treatment in a controlled Phase 2 or Phase 3 clinical trial produces a statistically significant benefit on a predefined clinical endpoint (e.g., mortality). An effective amount enhances the survivability of biological matter in response to a disease or injury, or an amount that induces stasis or pre-stasis in the biological matter.

It will be understood that when inducing stasis or pre-stasis in a tissue or organ, an effective amount is one that induces stasis or pre-stasis in the tissue or organ as determined by the collective amount of cellular respiration of the tissue or organ. Accordingly, for example, if the level of oxygen consumption by a heart (collectively with respect to cells of the heart) is decreased at least about 2-fold (i.e., 50%) after exposure to a particular amount of liquid chalcogenide composition of the present invention, it will be understood that the particular amount is an effective amount to induce stasis in the heart. Similarly, an effective amount to induce stasis or pre-stasis in an organism is one that is evaluated with respect to the collective or aggregate level of a particular parameter of stasis or pre-stasis. It will be also understood that when inducing stasis or pre-stasis in an organism, an effective amount is one that induces stasis or pre-stasis generally of the whole organism, unless a particular part of the organism was targeted. In addition, it is understood that an effective amount may be an amount sufficient to induce stasis or pre-stasis, or it may be an amount sufficient to induce stasis or pre-stasis in combination with another agent or stimuli, e.g., another compound, an injury, or a disease state.

In certain embodiments, the methods and compositions of the present invention induce stasis or pre-stasis in the biological material being treated. As used herein, "stasis" refers to a hypometabolic state wherein biological material is alive but is characterized by one or more of the following: at least a 50% (i.e., two-fold) reduction in the rate or amount of carbon dioxide production by the biological matter; at least a 50% reduction in the rate or amount of oxygen consumption by the biological matter; and at least a 10% decrease in movement or motility (applies only to cells or tissue that move, such as sperm cells or a heart or a limb, or when stasis is induced in the entire organism) (collectively referred to as "cellular respiration indicators").

In certain embodiments of the invention, it is contemplated that there is about, at least, at least about, or at most about a 2-, 3-, 4-, 5-, 6-, 7-, 8-, 9-, 10-, 15-, 20-, 25-, 30-, 35-, 40-, 45-, 50-, 60-, 70-, 80-, 90-, 100-, 150-, 200-, 250-, 300-, 350-, 400-, 450-, 500-, 600-, 700-, 800-, 900-, 1000-, 2000-, 3000-, 4000-, 5000-, or 10000-fold or more reduction in the rate of oxygen consumption by the biological matter, or any range derivable therein. Alternatively, it is contemplated that embodiments of the invention may be discussed in terms of a reduction in the rate of oxygen consumption by the biological matter as about, at least, at least about, or at most about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

Any assay to measure oxygen consumption may be employed, and a typical assay will involve utilizing a closed environment and measuring the difference between the oxygen put into the environment and oxygen that is left in the environment after a period of time. It is further contemplated that carbon dioxide production can be measured to determine the amount of oxygen consumption by biological matter. Thus, there may be decreases in carbon dioxide production, which would correspond to the decreases in oxygen consumption.

As used herein, "pre-stasis" refers to a hypometabolic state through which biological matter must transition to reach stasis. Pre-stasis is characterized by a reduction in metabolism within the biological material of a magnitude that is less than that defined as stasis. In order to achieve stasis using an effective compound, the biological matter necessarily must transition through a graded hypometabolic state in which oxygen consumption and $CO_2$ production are reduced less than 50% in the biological matter. Such a continuum, in which metabolism or cellular respiration is reduced to a degree less than 50%, is described as a state of "pre-stasis".

In addition, in various embodiments, pre-stasis is characterized by a reduction in one or more indicators of metabolic activity that is less than or equal to 1%, 2%, 5%, 10%, 15%, 20%, 25%, 30%, 35%, 40%, 45%, or 50% as compared to normal physiological conditions. In other embodiments, pre-stasis is characterized by its ability to enhance or promote entry into stasis in response to another stimuli, or its ability to enhance survival of or protect biological matter from damage resulting from an injury, the onset or progression of the disease, or bleeding, particularly bleeding that can lead to irreversible tissue damage, hemorrhagic shock, or lethality. While methods of the present invention explicitly exemplified herein may refer to inducing "stasis," it is understood that these methods may be readily adapted to induce "pre-stasis," and that such methods of inducing pre-stasis are contemplated by the present invention. In addition, the same methods and compositions used to induce stasis may also be used to induce pre-stasis, by providing them to biological matter at a lower dosage and/or for a shorter time than used to induce stasis.

In general, according to methods of the present invention, stasis or pre-stasis is temporary and/or reversible, meaning that the biological matter no longer exhibits the characteristics of stasis at some later point in time and that treatment is not so toxic to the biological material that it dies or decomposes.

According to various embodiments of the methods of the present invention, stasis or pre-stasis is induced by treating biological matter with an amount of an liquid chalcogenide composition of the present invention that induces stasis directly itself or, alternatively, by treating biological matter with an amount of an liquid chalcogenide composition of the present invention that does not itself induce stasis or pre-stasis, but instead, promotes or enhances the ability of or decreases the time required for the biological matter to achieve stasis in response to another stimuli, such as, but not limited to, an injury, a disease, hypoxia, excessive bleeding, or treatment with one or more effective compounds, as described herein.

In certain embodiments, the liquid pharmaceutical composition of the present invention is used to treat or prevent injury to biological matter exposed to ischemic or hypoxic conditions. In one embodiment, these methods are used to treat patients who have undergone, are undergoing, or who are susceptible to injury, trauma or critical care treatment. Injury may be caused by external insults, such as burns, wounds, amputations, gunshot wounds, or surgical trauma, abdominal surgery, prostate surgery, internal insults, such as septic shock, stroke or cardiac arrest, heart attack that result in the acute reduction in circulation, or reductions in circulation due to non-invasive stress, such as exposure to cold or radiation. On a cellular level, injury often results in exposure of cells, tissues and/or organs to hypoxia, thereby resulting in induction of programmed cell death, or "apoptosis."

Therefore, the present invention contemplates contacting tissues, organs, limbs and even whole organisms with an effective amount of a liquid chalcogenide composition of the present invention as a way of protecting them from the detrimental effects of injury. In a specific scenario, where medical attention is not readily available, this can "buy time" for a patient, until they can receive appropriate medical attention. The present invention also contemplates methods for inducing tissue regeneration and wound healing by prevention/delay of biological processes that may result in delayed wound healing and tissue regeneration. In this context, in scenarios in which there is a substantial wound to the limb or organism, contacting the biological matter with an liquid chalcogenide composition aids in the wound healing and tissue regeneration process by managing the biological processes that inhibit healing and regeneration. In addition to wound healing, methods of the invention can be implemented to prevent or treat trauma such as cardiac arrest or stroke, and hemorrhagic shock. The invention has importance with respect to the risk of trauma from emergency surgical procedures, such as thoroacotomy, laparotomy, and splenic transaction or cardiac surgery, aneurysm, surgery, brain surgery and the like.

In certain embodiments, methods of the present invention can be implemented to enhance survivability and prevent ischemic injury resulting from cardiac arrest or stroke. Accordingly, in one embodiment, the present invention includes methods of enhancing survivability or reducing ischemic injury in a patient suffering from or at risk of cardiac arrest or stroke, comprising providing an effective amount of an liquid chalcogenide composition to the patient before, after, or both before and after myocardial infarction, cardiac arrest or stroke.

The term "treatment of a disease" as used herein refers to the management and care of a patient having developed the disease, condition or disorder. The purpose of treatment is to diminish the detrimental effects of the disease, condition or disorder. Treatment includes the administration of the effective compounds to eliminate or control the disease, condition or disorder as well as to alleviate the symptoms or complications associated with the disease, condition or disorder.

In certain embodiments, methods of the present invention include pre-treating a biological material, e.g., a patient, prior to an ischemic or hypoxic injury or disease insult. These methods can be used when an injury or disease with the potential to cause ischemia or hypoxia is scheduled or elected in advance, or predicted in advance to likely occur. Examples include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient in need of an organ transplant. Examples include, but are not limited to, medical conditions in which a risk of injury or disease progression is inherent (e.g., in the context of unstable angina, following angioplasty, bleeding aneurysms, hemorrhagic strokes, following major trauma or blood loss), or in which the risk can be diagnosed using a medical diagnostic test.

Moreover, additional embodiments of the invention concern enhancing survivability and preventing irreversible tissue damage from blood loss or other lack of oxygenation to cells or tissue, such as from lack of an adequate blood supply. This may be the result of, for example, actual blood loss, or it may be from conditions or diseases that cause blockage of blood flow to cells or tissue, that reduce blood pressure locally or overall in an organism, that reduce the amount of oxygen that is carried in the blood, or that reduces the number of oxygen carrying cells in the blood. Conditions and diseases that may be involved include, but are not limited to, blood clots and embolisms, cysts, growths, tumors, anemia (including sickle cell anemia), hemophilia, other blood clotting diseases (e.g., von Willebrand, or ITP), and atherosclerosis. Such conditions and diseases also include those that create essentially hypoxic or anoxic conditions for cells or tissue in an organism because of an injury, disease, or condition.

In one embodiment, the present invention provides methods to enhance the survivability of and prevent injury or damage to biological material undergoing hemorrhagic shock, which include contacting the biological material at risk of or in a state of hemorrhagic shock with an effective amount of a liquid chalcogenide composition as soon as practical, ideally within one hour of the injury. This method allows for the patient to be transported to a controlled environment (e.g., surgery), where the initial cause of the injury can be addressed, and then the patient can be brought back to normal function in a controlled manner. For this indication, the first hour after injury, referred to as the "golden hour," is crucial to a successful outcome.

In various other embodiments, the methods of the present invention may be used in the treatment of neurodegenerative diseases associated with ischemia or hypoxia, in the treatment of hypothermia, in the treatment of hyperproliferative disorders, and in the treatment of immune disorders. In various other embodiments, the biological condition is any one or combination of the following: neurological disease, cardiovascular disease, metabolic disease, infectious disease, lung disease, genetic disease, autoimmune disease, and immune-related disease.

In certain embodiments, the methods of the present invention are used to enhance the survivability of ex vivo biological matter subjected to hypoxic or ischemic conditions, including, e.g., isolated cells, tissues and organs. Specific examples of such ex vivo biological material include platelets and other blood products, as well as tissues and organs to be transplanted.

In one embodiment, methods of the present invention may be used to enhance survivability of biological material in the laboratory or research context, for example when cell lines or laboratory organisms are purposefully subjected to hypoxic or ischemic conditions, e.g., during cryopreservation and storage. For example, cells, tissues or organs may be stored or transported in the presence of a liquid chalcogenide composition of the present invention. The methods of the present invention may be used to increase the survivability of donor tissues and organs, thereby extending the time before the donor tissue must be transplanted into a recipient and blood flow restored. These methods may be combined with current preservation methods, including the use of other preservation agents and oxygen perfusion. The present invention provides methods of enhancing survivability of platelets, including, in particular embodiments, platelets stored in an anoxic environment, comprising contacting the platelets with an effective amount of a liquid chalcogenide composition during storage.

The present invention also provides methods and compositions for preserving both non-living biological material and preserving or extending the shelf-life of non-biological material. These methods comprise contacting the non-living biological matter or non-biological material with a liquid chalcogenide composition.

In certain embodiments, the amount of or effective compound that is provided to biological material can be about, at least, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg, mg/kg, or mg/m2, or any range derivable therein. Alternatively, the amount may be expressed as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mM or M, or any range derivable therein.

In various embodiments of the present invention, biological material is exposed to liquid pharmaceutical compositions of the current invention for about, at least, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or more, and any range or combination therein.

Furthermore, when administration is intravenous, it is contemplated that the following parameters may be applied. A flow rate of about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 gtts/min or µgtts/min, or any range derivable therein. In some embodiments, the amount of the solution is specified by volume, depending on the concentration of the liquid chalcogenide composition. An amount of time may be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months, or any range derivable therein.

Volumes of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mls or liters, or any range therein, may be administered overall or in a single session.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

EXAMPLE 1

Method and Manufacture of Liquid Pharmaceutical Compositions I-IV

Four liquid pharmaceutical chalcogenide compositions were prepared as described below.

Stock solutions were prepared using deoxygenated water. The water was deoxygenated by removing air under vacuum and dissolving with compressed nitrogen (99.99%) for 30 minutes. A saturated stock solution of 2.5 M $Na_2S$ was prepared from $Na_2S*9H2O$ crystals (Fisher #5425) that were rinsed with oxygen-free, distilled, deionized water. This stock was stored tightly sealed and protected from light. A 220 mM stock solution of HCl was prepared by dilution of concentrated acid (Fisher #A144-212) and deoxygenated by dissolving with compressed nitrogen.

Liquid pharmaceutical compositions were prepared in a fume hood in a basic glove box filled with nitrogen gas to yield an oxygen-free environment. The reactor with pH meter, bubbler and stirrer were in the glove box. Oxygen levels in the glove box were monitored with an oxygen meter (Mettler-Toledo) with a sensitivity level of 0.03 µM. Methods of preparing the liquid pharmaceutical compositions of the present invention include limiting oxygen content in each aspect of manufacturing and storage of the pharmaceutical composition where oxygen is measured in the range of 0 µM-5 µM in the pharmaceutical composition.

Liquid pharmaceutical compositions were prepared in a three-neck flask (Wilmad Labs) with each opening fitted with ground glass fittings having the following features:
 a) A universal adapter with a plastic cap with a central orifice and o-ring. This adapter was fitted with a pH probe and sealed by the O-ring.
 b) Universal adapter with a hose connector and a plastic cap with a central orifice and O-ring. This adapter was fitted with a gas dispersion tube with a glass frit. The dispersion tube was connected to a compressed gas cylinder and used to deoxygenate the solution by dissolving with compressed nitrogen and to neutralize the pH with a mixture of $H_2S$ and nitrogen. The hose connector was fitted with a plastic tube to allow pressure to escape. These two connections were reversed to dispense the contents of the flask under positive nitrogen pressure.
 c) The third neck was sealed with a ground glass stopper and used to add $Na_2S$ solution or water to the flask.

1. Liquid Pharmaceutical Composition I—$Na_2S$ Nonahydrate

Liquid Pharmaceutical Composition I was prepared with the following steps:
 a) Oxygen-free distilled, deionized water was added to a three neck flask and deoxygenated by dissolving with nitrogen for 30 minutes while stirring.
 b) 2.5 M $Na_2S$ Stock was added to yield a 200 mM $Na_2S$ solution.
 c) The 200 mM $Na_2S$ Solution was bubbled with compressed nitrogen for 15 minutes while stirring.

d) 220 mM HCl was added until a final pH of 7.8-8.0 while dissolving with compressed nitrogen and stirring.
e) Deoxygenated deioinized water was added to give a final concentration of 100 mM $Na_2S$.

2. Liquid Pharmaceutical Composition II—$Na_2S$ Nonahydrate

Liquid Pharmaceutical Composition II was prepared with the following steps:
a) Deionized, oxygen-free water was added to the three neck flask and deoxygenated by dissolving with nitrogen for 30 minutes while stirring.
b) 2.5 M $Na_2S$ Stock was added to yield a 100 mM $Na_2S$ solution.
c) The 100 mM $Na_2S$ Solution was bubbled with compressed nitrogen for 15 minutes while stirring.
d) The solution was bubbled with a 50/50 mixture of compressed nitrogen and $CO_2$ (99.9%) until a pH of 7.8 was reached.

3. Liquid Pharmaceutical Composition III—$Na_2S$ with $H_2S$ and Nitrogen

Liquid Pharmaceutical Composition III was prepared with the following steps:
a) Deionized, oxygen-free water was added to the three neck flask and deoxygenated by dissolving with nitrogen for 30 minutes while stirring.
b) 2.5 M $Na_2S$ Stock was added to yield a 100 mM $Na_2S$ solution.
c) The 100 mM $Na_2S$ Solution was bubbled with compressed nitrogen for 15 minutes while stirring.
d) The solution was bubbled with a 50/50 mixture of compressed nitrogen and $H_2S$ until a pH of 8.2 was reached. This resulted in a final concentration of 90 mM sulfide.

4. Liquid Pharmaceutical Composition IV—$H_2S$

The final sulfide concentration of Liquid Pharmaceutical Composition IV was determined by the initial concentration of NaOH. Liquid Pharmaceutical Composition IV was prepared with the following steps:
a) NaOH in a range of 5 mM to 500 mM solution was added to the three neck flask with additives (DTPA, anti-oxidants) (FIG. 1.)
b) The solution was deoxygenated by bubbling with argon at 5 psi for 15 minutes while stirring.
c) $H_2S$ was bubbled through the solution while stirring until pH was reduced to 7.7 (or a range of 7.6 to 7.8).
d) The headspace in the flask was flushed with argon.
e) Amber dispensing bottles or vials were placed in a glove box that was flushed with a constant stream of argon and each bottle or vial was flushed with argon.
f) The formulation was dispensed under argon to maintain an oxygen-free environment.

The stability of the solution was monitored by measurement of sulfide concentration, pH, and absorbance spectrum (polysulfide formation). Additional assays were performed to monitor oxidation products which include sulfite, sulfate, thiosulfate, and elemental sulfur.

Liquid pharmaceutical compositions were dispensed within the sealed Glove box, from the three-necked flask under positive nitrogen pressure. Amber vials or amber bottles were filled to a slight over-pressure in an inert atmosphere argon or nitrogen to prevent/slow oxidative breakdown of the liquid pharmaceutical compositions, and sealed with plastic caps with Teflon/silicon liners or plastic caps with central Teflon lined silicon septa using a crown-cap crimper (Aldrich Z112976) to provide an air-tight seal.

EXAMPLE 2

Figure 1:
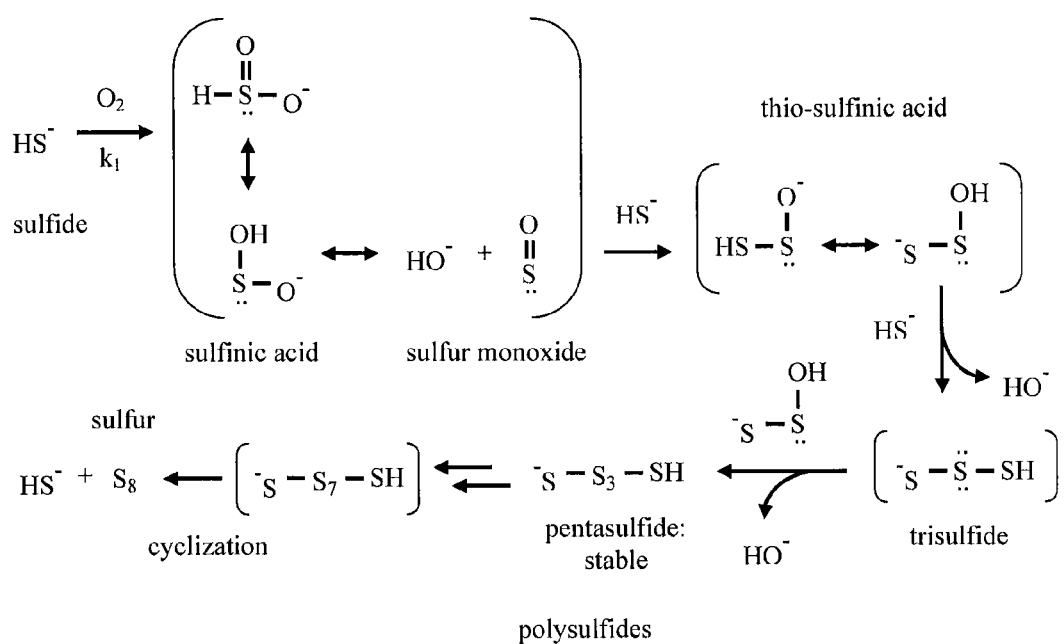
FIG. 1 is a drawing illustrating sulfide oxidation species detected at a pH range of 7.0-9.0 when the concentration of sulfide is greater than the concentration of molecular oxygen ([Sulfide]>[$O_2$]).
Figure 2:
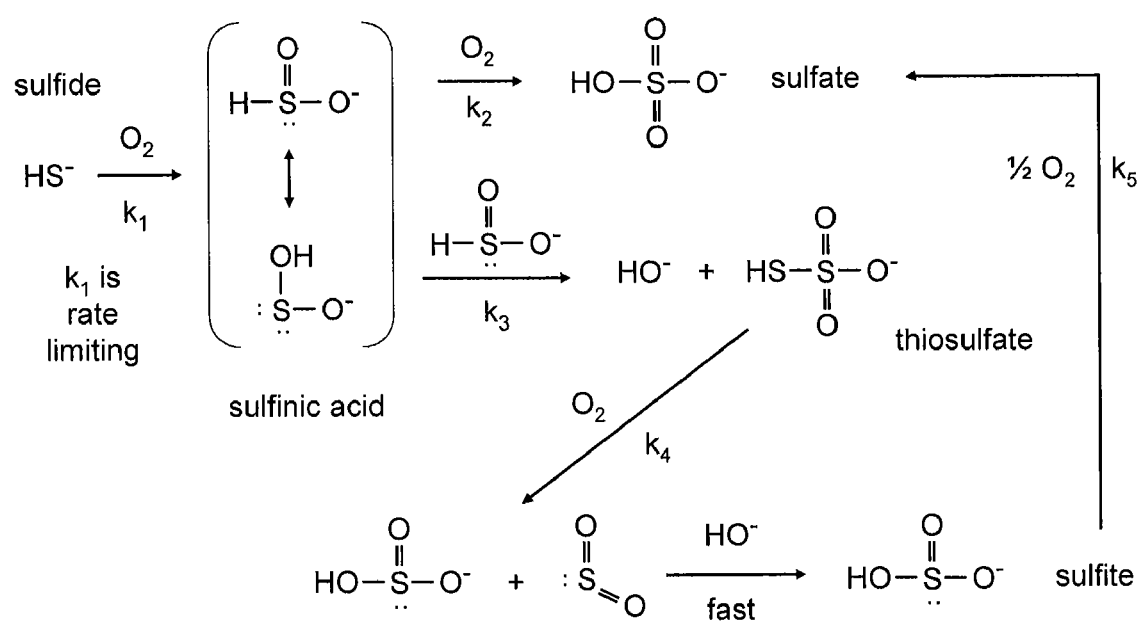
FIG. 2 is a drawing illustrating the oxidation products that are detected in an aqueous sulfide solution at a pH range of 7.0-9.0.

Liquid Pharmaceutical Chalcogenide Compositions Manufactured in an Oxygen-Free Environment Have Stable Sulfide and Reduced Sulfide Oxygenation Products Sulfides are subject to oxygenation, resulting in a variety of oxidation products, including those depicted in FIGS. 1 and 2. (See: Chen et al., *Environ. Sci. Technol.* (1972), p. 529-537; Kotronarou et al., *Environ. Sci. Technol.* (1992), p. 2420-2428; Beaucham et al., *Critical Reviews in Toxicology* (1984); p. 25-97)

The stability of three formulations of liquid pharmaceutical composition IV when manufactured in a fume hood in a basic glove box filled with nitrogen gas to yield an oxygen-free environment was tested. In this study, oxygen levels in the glove box and in the solution were monitored with an oxygen meter (Mettler-Toledo) with a sensitivity level of 0.03 µM. The liquid pharmaceutical compositions were prepared as described in Example 1.

Three preparations of Liquid Pharmaceutical Composition IV were prepared, including: (1) 97 mM, pH 7.62, 273 mOsm; (2) 98 mM, pH 7.71, 291 mOsm; and (3) 98 mM, pH 7.75, 276 mOsm. There compositions were tested to determine if preparation in an oxygen-free environment enhanced sulfide stability and reduced measurable oxidation products. Liquid pharmaceutical compositions were manufactured in the reactor apparatus in a sealed glove box that was flushed with nitrogen gas to minimize oxygen content in the box (0.02 µM). Sulfide levels and oxidation products (polysulfides, sulfite, thiosulfate, sulfate and an unknown peak) of parenteral liquid pharmaceutical composition were analyzed over a 129 day period.

Figure 3:
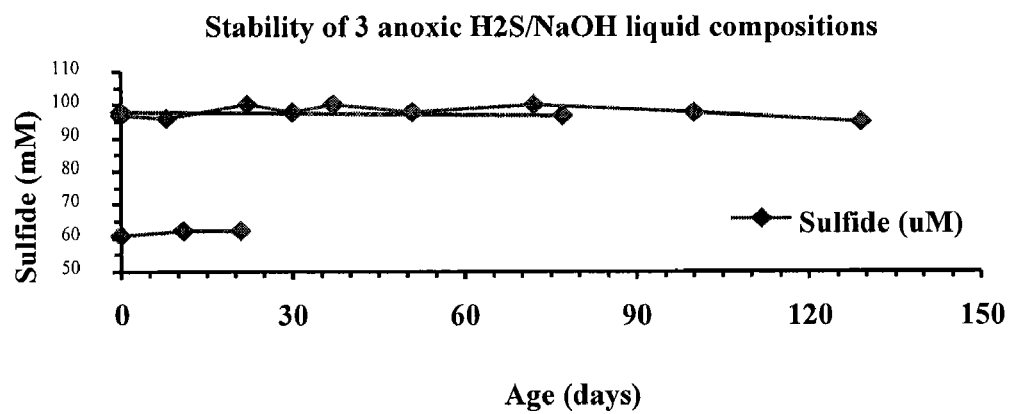
FIG. 3 is a graph depicting sulfide levels over time for three different preparations of liquid compositions of $H_2S$ (Liquid Pharmaceutical Composition IV).

Sulfide was measured by Ion Selective Electrochemistry (ISE). Ion Selective Electrochemistry (ISE) is a technique for measuring ionic species. The electrode contained a membrane that is specific to an ionic species where the ions bind to the surface of the membrane. The amount of ions bound to the membrane established a potential difference that is dependent on the concentration of ions in solution. Sulfide levels remained at 100% of control over the measured time period (FIG. 3).

Figure 5A:
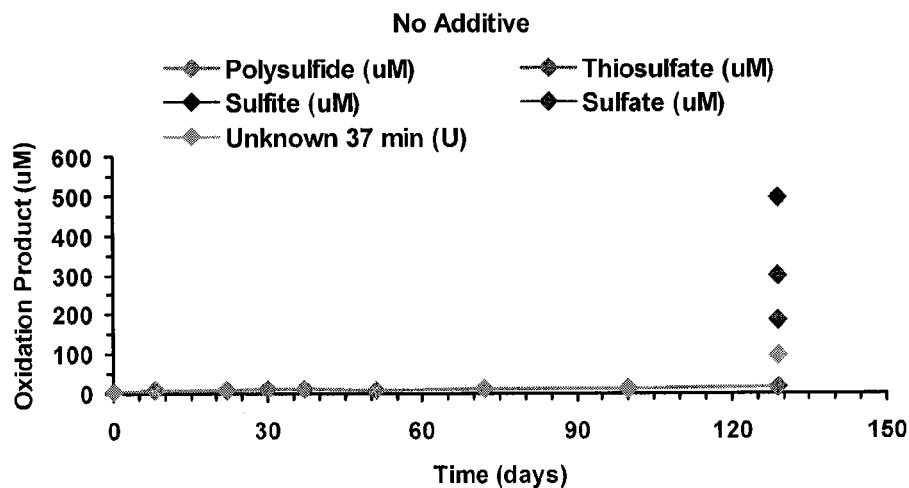
FIGS. 5A and 5B are graphs depicting levels of oxidation products measured (i.e., sulfite, polysulfide, thiosulfate, sulfate and an unknown oxidation product identified at 37 minutes) over 129 days in a liquid composition of hydrogen sulfide ($H_2S$) (Liquid Pharmaceutical Composition IV) prepared in an oxygen-free environment, either in the presence (5B) or absence (5A) of DTPA.

Sulfite, thiosulfate and sulfate were analyzed using Ion Chromatography (IC) and were analyzed at 0, 8, 22, 30, 37, 51, 72, 100 and 129 days. Ion Chromatography (IC) was used for the analysis of ionic species and measured differential migration of sample components in a biphase system. Sample components that interacted less with the stationary phase spend less time in the column. The time an ion spends in the column from injection to detection is known as retention time, a measure of component identity whereas peak height or area is a measure of component concentration. The upper limit of detection for sulfate in the assay was <0.08% and the range of potential sulfate values were considered to be between 0%-<0.08%. Polysulfides were measured in the Spectramax at 370 nM relative to distilled $H_2 0$ (see: Weiss, J. and Weiss T. *Handbook of Ion Chromatography*; Wiley, Third Edition (2005); O'Brien D. J. et al., *Environ. Sci. Technol.* 1977, p. 1114-1120; Hoffmann M. R., et al., *Environ. Sci. Technol.* 1979, p. 1406-1414; Tossell, J. A, *Chemical Geology.* 1997, p. 93-103; Chen, K. *Environ. Sci. Technol.* 1972, p. 529-537; Kotronarou A. et al., *Environ. Sci. Technol.* 1992, p. 2420-2428). The amount of detected oxidation products is depicted in FIG. 5A.

EXAMPLE 3

Stability of Liquid Pharmaceutical Composition IV as Measured by Formation of Polysulfide in the Presence or Absence of DTPA The ability of a synthetic chelator to enhance the stability of a liquid pharmaceutical composition of sulfide was examined. Two liquid pharmaceutical compositions (Liquid Pharmaceutical Composition IV) were prepared in a fume hood in a basic glove box filled with nitrogen gas to yield an oxygen-free environment. The liquid chalcogenide compositions were manufactured in a sealed container that contained a three neck flask with ground glass fittings (vessel) to hold the liquid chalcogenide composition with access ports for pH measurement, addition of gasses, and a port available for dispensing without contact to the outside atmosphere. The vessel was flushed with nitrogen gas or argon gas to minimize oxygen content. In these pharmaceutical compositions, the final sulfide concentration was determined by the initial concentration of NaOH.

Figure 4:
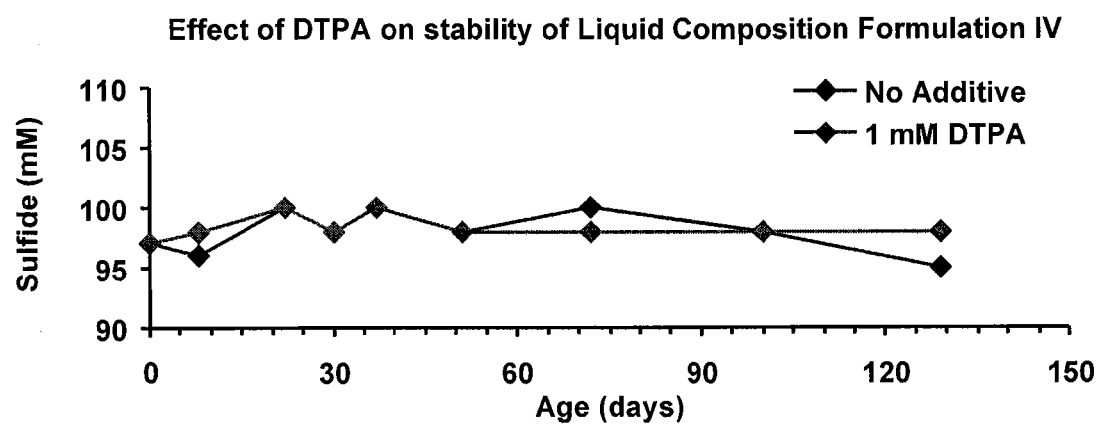
FIG. 4 is a graph that compares sulfide stability in compositions of $H_2S$ (Liquid Pharmaceutical Composition IV) over 129 days, manufactured either with or without the synthetic chelator, Diethylenetriaminepentaacetic acid (DTPA).

NaOH solution was placed in the three neck flask either without any additives or with DTPA to enhance stability. Both formulations contained NaCl to balance osmolarity and the solution was deoxygenated by dissolving with argon at 5 psi for 15 minutes while stirring. Oxygen levels in the glove box were monitored with an oxygen meter (Mettler-Toledo) with a sensitivity level of 0.03 μM. The tested liquid pharmaceutical compositions of sulfide $H_2S$ 97 mM (Liquid Pharmaceutical Composition IV) were made either with or without the synthetic chelator, Diethylenetriaminepentaacetic acid (DTPA) (1 mM). Sulfide and polysulfide levels were measured at days 0, 8, 22, 30, 37, 51, 72, 100 and 129 days with a spectrophotometer (Spectromax) at peak absorbance 370 nm. As illustrated in FIG. 4, the presence of 1 mM DTPA enhanced the stability of sulfide in the formulation at day 129.

Figure 5B:
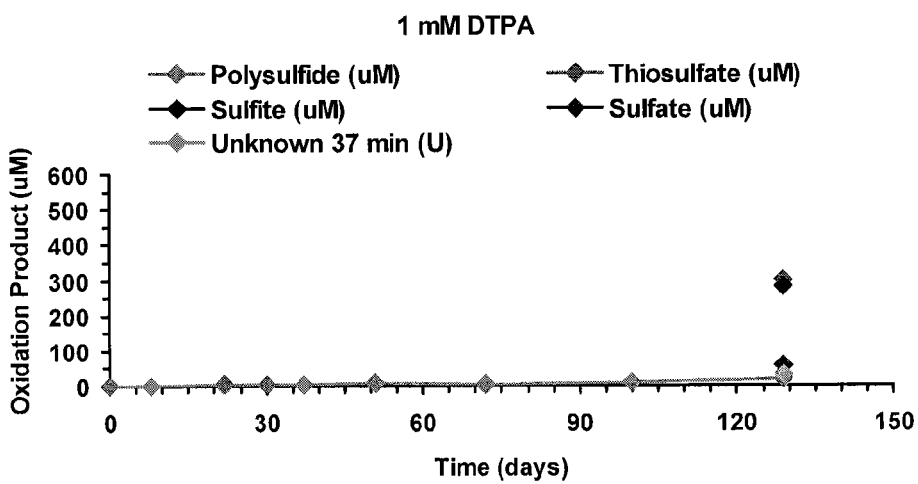

Oxidation products sulfite (uM), sulfate (uM), thiosulfate (uM) and an unknown product measured at 37 min (U) were measured at day 129. As shown in FIGS. 5A and 5B, the presence of 1 mM DTPA resulted in a decreased level of oxidation products at 129 days. Polysulfide formation is measured at less than 0.03% of total sulfide concentration at the end of 129 days.

EXAMPLE 4 pH is Stable in a Liquid Pharmaceutical Composition of Sulfide

Hydrogen sulfide is a weak, diprotic acid and exists in three forms in solution ($H_2S$, HS— and $S_2$—). The ratio of sulfur species in solution is dependent upon pH. At pH 7, HS— is the primary species. $H_2S$ is the predominant species at a pH below 7 (see: O'Brien D. J. et al., *Environ. Sci. Technol.* 1977, p. 1114-1120).

Figure 6:
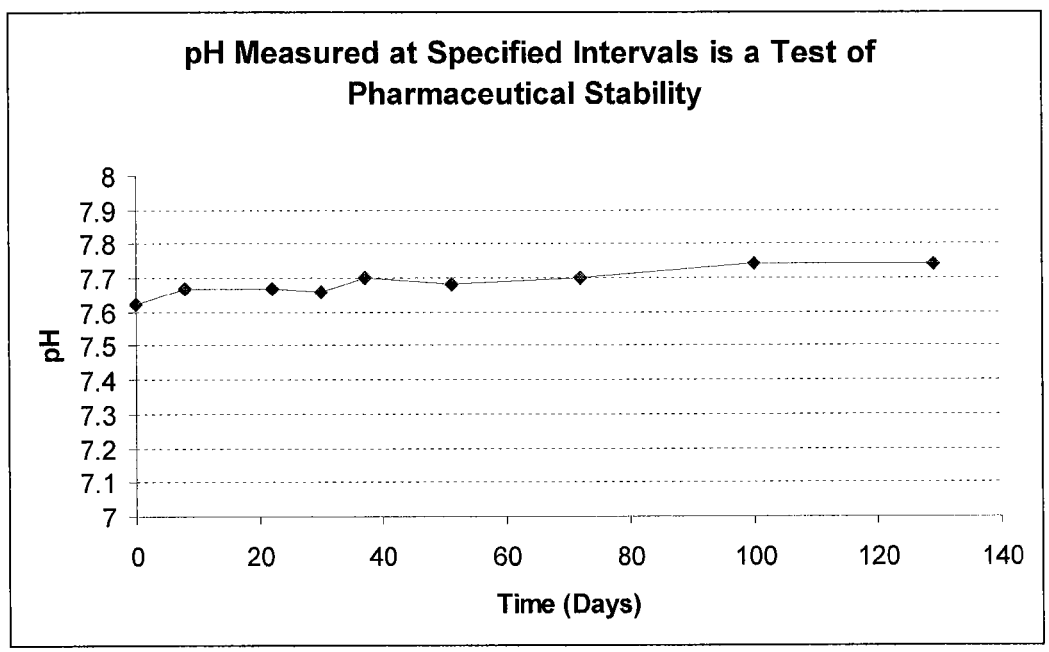
FIG. 6 is a graph of the pH levels of a liquid composition of sulfide, 97 mM $H_2S$ (Liquid Pharmaceutical Composition IV) measured at specified intervals over a 129 day period.

To test the pharmaceutical stability of sulfide in Liquid Pharmaceutical Composition IV, the pH was measured at specified time points for 129 days. The liquid pharmaceutical composition of sulfide 100 mM $H_2S$ (Liquid Pharmaceutical Composition IV) was manufactured in the reactor apparatus in a sealed glove box that was flushed with nitrogen gas to minimize oxygen content in the box (measured at less than 0.02 μM). pH was measured at 0, 8, 22, 30, 37, 51, 72, 100 and 129 days using a pH meter (Thermo Electron Corp.). pH was stable over the 129 day period with an average value of 7.68±0.04 (Mean +Standard Deviation) (FIG. 6).

A liquid pharmaceutical composition of sodium sulfide was prepared that met Good Manufacturing Practices (GMP) acceptance criteria, including concentration, pH, and osmolality, after storage at various commercially acceptable temperatures and durations of time.

EXAMPLE 5

Detection of Sulfide and Oxidation Products in Rat Urine Following Administration of Liquid Pharmaceutical Composition IV The metabolic profile of oxidation products of sulfide in urine was measured in rodents. Levels of the oxidation products thiosulfate and sulfate were measured in rat urine following IV dosing of a bolus of Liquid Pharmaceutical Composition IV (98 mM sulfide, pH 7.65, 293 m/Osmol).

A 10-11 week, female Sprague Dawley rat, 200-250 grams (Taconic, Prunedale, Calif.) was anesthetized (100 mg/kg ketamine and 10 mg/kg xylazine) and implanted with two jugular vein catheters (JVC) and a urethral cannula. Anesthesia was maintained for the duration of the experiment. A bolus dose of Liquid Pharmaceutical Composition IV (0.5 mg/kg) was injected through the jugular vein catheter. Phosphate Buffered Saline (PBS) was infused for the duration of the experiment at a rate of 3 mL/hr using an infusion pump (Harvard Apparatus). Urine samples were collected before injection (time=0) and in 15 minute intervals up to 60 min after administration and stored at 4° C. for analysis.

Figure 7A:
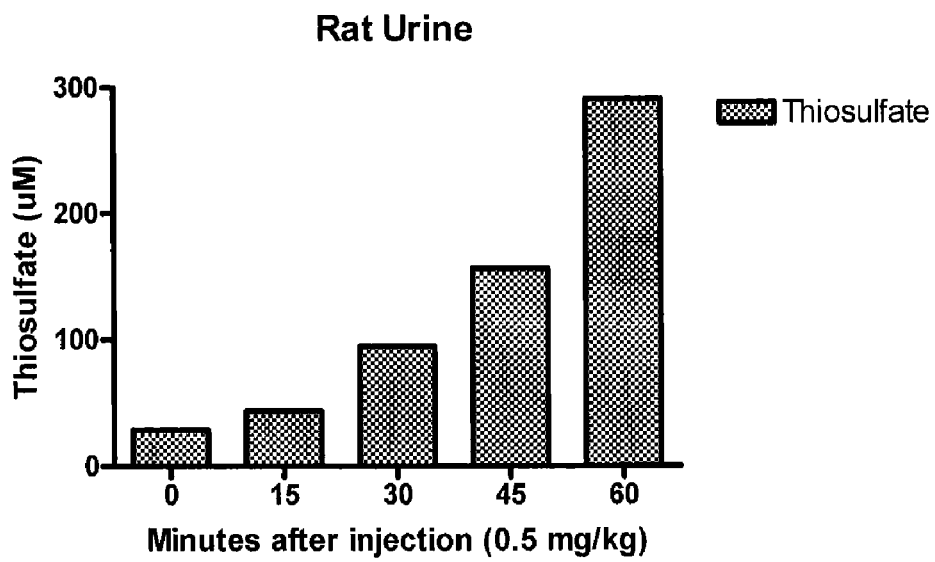
FIG. 7A is a graph demonstrating urinary thiosulfate excretion following a bolus injection of Liquid Pharmaceutical Composition IV. The graph depicts the amount of thiosulfate measured in rat urine at the indicated time points following administration.
Figure 7B:
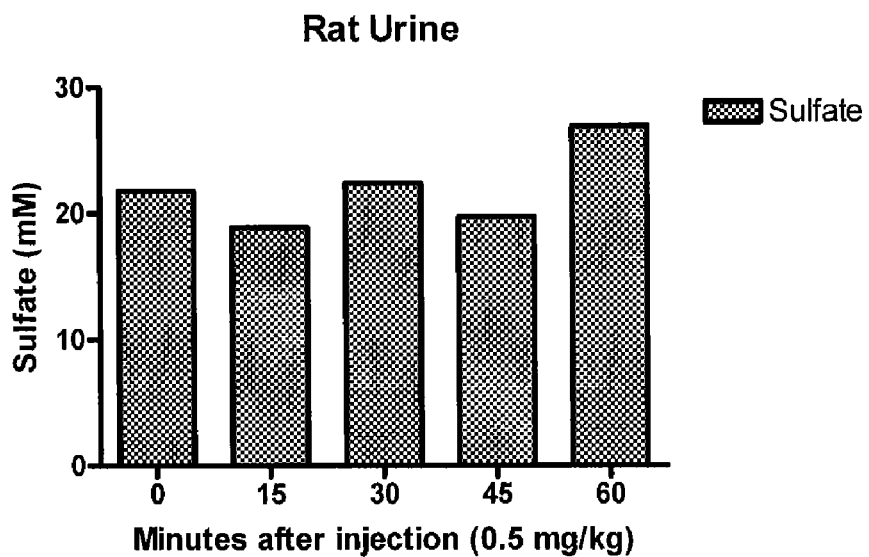
FIG. 7B is a graph showing urinary sulfate excretion following a bolus injection of Liquid Pharmaceutical Composition IV. The graph depicts the amount of sulfate measured in rat urine at the indicated time points following administration.

Urinary thiosulfate and sulfate levels were analyzed by Ion Chromatography (Metrohm AG 861 IC with Metrosep A supp 5 column). The urine samples were diluted 1:20 in IC Eluent (3.2 mM sodium carbonate/1.0 mM sodium bicarbonate). At the end of 60 minutes, levels of excreted thiosulfate increased to 300 μM excreted (FIG. 7A). Levels of excreted sulfate averaged 22±3 mM over 60 minutes (FIG. 7B). These data indicate that the sulfide oxidation products thiosulfate and sulfate are excreted in urine and can be detected by Ion Chromatography.

EXAMPLE 6

Detection of Sulfide and Thiosulfate in Rat Blood Following Administration of Liquid Pharmaceutical Composition IV Sulfide and thiosulfate levels were measured in rat blood using a derivatization method and GC-MS analysis following IV dosing of a bolus of Liquid Pharmaceutical Composition IV.

Three 10-11 week-old, male Sprague Dawley rats, (326-350) grams (Taconic, Prunedale, Calif.) with a jugular vein catheter (JVC) and a carotid artery cannula (CAC) were used. Animals were allowed to recover and acclimate in a temperature and humidity controlled environment for 5-6 days prior to the commencement of experimental procedures. Food and water were provided ad libitum.

A baseline blood sample (~0.3 ml) was collected from each rat through the carotid artery cannula into a heparin-coated 1 ml syringe fitted with a 23g Luer stub adapter. After sampling, a corresponding volume of saline was slowly injected into the animal through the carotid artery cannula, followed by 100 μl of heparin solution (heparinized dextrose 50 IU/ml). A bolus dose of liquid pharmaceutical composition IV (1 mg/kg i.v.) (98 mM sulfide, pH 7.65, 293 mOsm) was injected through the jugular vein catheter. Blood (~0.3 mL) was immediately collected after dosing through the carotid artery catheter using a heparin-coated 1 mL syringe with a 23-g Luer stub adapter. The blood sample was immediately processed as described. After sampling, a corresponding volume of saline was slowly injected into the animal through the carotid artery catheter. Blood sampling was repeated at 10 minutes, 30 minutes, 60 minutes, 2 hours and 4 hours after injection.

0.2 ml rat blood was drawn with a syringe and immediately added to a 9 ml amber vial containing: 5% NaCl solution, 200 mM ascorbic acid solution (freshly prepared), 20 mM pentafluorobenzylbromide (PFBBr) solution in acetone. The preparation was closed with screw cap (with PTFE-lined septum) and vortexed for 1 minute. The mixture was allowed to incubate 15 minutes, and then to each vial was added 5 mM tetradecyldimethylbenzylammonium chloride solution in oxygen-free water saturated with sodium-tetraborate, 25 mM iodine solution in ethylacetate, 50 mM pentafluorobenzylbromide solution in ethylacetate. The preparation was vortexed for 30 seconds, and then incubated for 5 minutes. 100 mg potassium dihydrogen phosphate was then added, and the solution was vortexed 30 sec. The solution was then incubated for 1 hour to complete the reaction, and after that centrifuged at 2500 rpm for 15 minute. Supernatant (the organic phase) was removed and dried down for analysis with GC/MS. (Kage, et al., *Journal of Forensic Science* (1988) 33:217; Kage, et al, *Journal of Analytical Toxicology* (1991) 15:148).

Figure 8A:
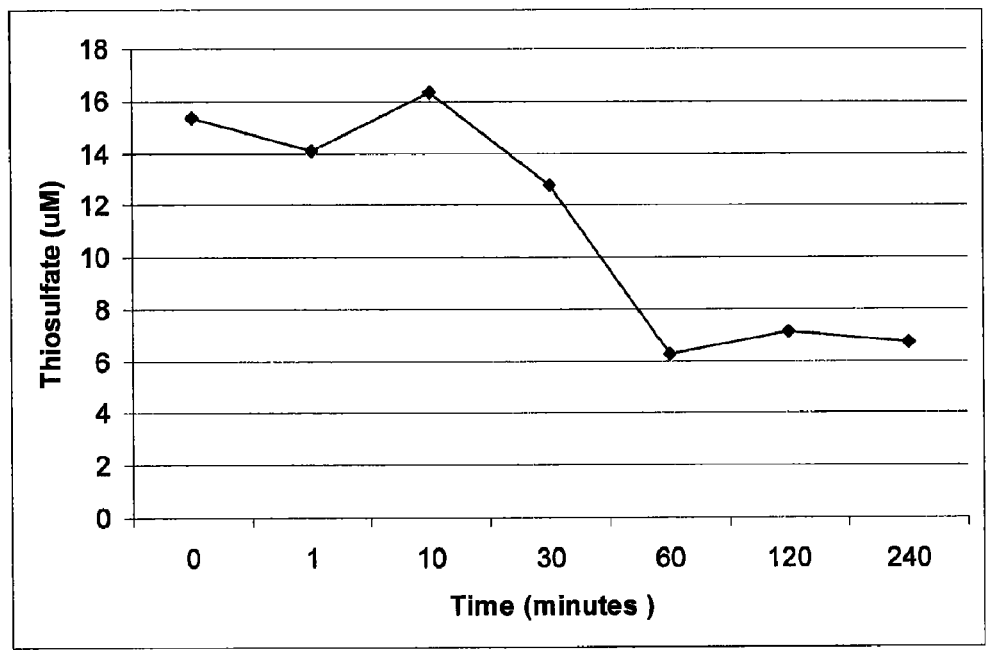
FIG. 8A is a graph showing blood thiosulfate levels measured in a rat over a 240 minute period following a bolus injection of Liquid Pharmaceutical Composition IV (1 mg/kg). In this study, blood was drawn from the carotid artery and samples derivatized with PFBBr and analyzed by GC-MS.
Figure 8B:
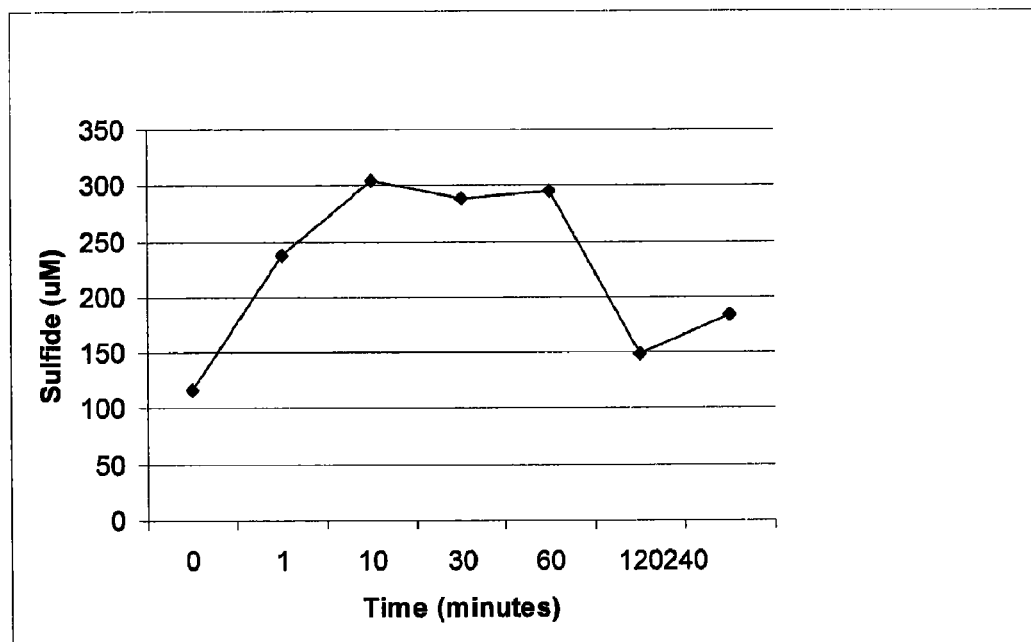
FIG. 8B is a graph showing blood sulfide levels measured in a rat over a 240 minute period following a bolus injection of Liquid Pharmaceutical Composition IV (1 mg/kg). In this study, blood was drawn from the carotid artery and samples deriviatized with PFBBr and analyzed by GC-MS.

These results show that using the method of PFB-Br derivatization, sulfide and thiosulfate can be simultaneously detected in blood from a rat injected i.v. with a bolus dose of Liquid Pharmaceutical Composition IV (FIGS. 8A and 8B). Sulfide levels were recovered from blood for the 240 minute study period with a Cmax at 10 minutes (FIG. 8B).

EXAMPLE 7

Liquid Pharmaceutical Compositions Enhance Survival Under Hypoxic Conditions

Treatment with gaseous $H_2S$ has been shown to enhance an animal's ability to survive under hypoxic conditions. However, under certain circumstances, such as when an immediately life-threatening injury has occurred at a remote location, it would be highly advantageous to be able to treat a patient with a liquid pharmaceutical chalcogenide composition. Liquid sulfide compositions were prepared as described in Example I and tested their ability to enhance an animal's ability to survive in a hypoxic environment.

In one set of experiments, three different liquid pharmaceutical compositions were tested in male C57BL/6 jugular vein catheterized (JVC) mice, 5-6 weeks old (Taconic), by infusing the animals with the liquid sulfide liquid pharmaceutical compositions using 1 mL or 5 mL Luer-Lok syringes (Becton Dickison). An IPTT-300 transponder from Bio Medic Data Systems (BMDS) was used to monitor body temperature. The transponder was injected subcutaneous (S.C.) into the back of the animals at least 24 hours prior to the experiment. A DAS-6008 data acquisition module from BMDS recorded body temperature of the mouse via the transponder, and data was input into a computer spreadsheet and plotted against time.

Each mouse was dosed with liquid pharmaceutical compositions through the in-dwelling catheter using an infusion pump (Harvard Apparatus). The mouse was infused until the temperature chip implanted in the skin registered a body temperature of 33° C. If the mouse showed signs of distress before the temperature dropped to 33° C., then the infusion was stopped for 10 minutes and restarted at a rate lower than the previous rate. Once the animal's temperature dropped to 33° C. or below, the infusion was stopped and the mouse was transferred into a hypoxic atmosphere (4.0% $O_2$).

In a first experiment, a mouse (ID: MJVC07) was infused with a liquid $Na_2S$ solution, pH 7.75 (Liquid Pharmaceutical Composition I). In this example, Liquid Pharmaceutical Composition I was prepared by diluting a saturated stock of $Na_2S$ in deionized, deoxygenated $H_2O$ to a concentration of 43 mM, and deoxygenating the solution by dissolving with 100% $N_2$, while stirring for 30 minutes in a 3-necked flask with ground glass fittings to allow pH monitoring and gas addition with minimal air contact. The pH of the solution was adjusted to 7.75 using 220 mM HCl while dissolving with $N_2$ and stirring. The final solution (Liquid Pharmaceutical Composition I) was dispensed under argon into amber vials using minimal headspace and sealed with caps using Teflon/silicon liners or septa. The saturated stock of $Na_2S$ used to prepare Liquid Pharmaceutical Composition I was itself prepared by dissolving approximately 1.0 g washed $Na_2S$ crystals per milliliter deionized, deoxygenated $H_2O$, and this stock was stored tightly capped, protected from light.

Figure 9:
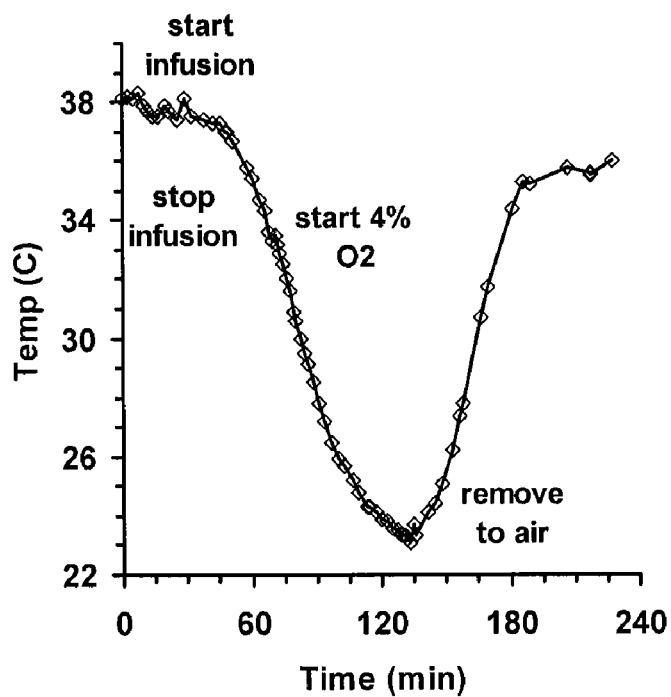
FIG. 9 is a graph showing the core body temperature over time of a mouse (MJVC07) infused with $Na_2S$ (Liquid Pharmaceutical Composition I) and exposed to hypoxic conditions (4% $O_2$). The times at which the infusion was started and stopped and the times at which exposure to hypoxic conditions was started and stopped are indicated.
Figure 10:
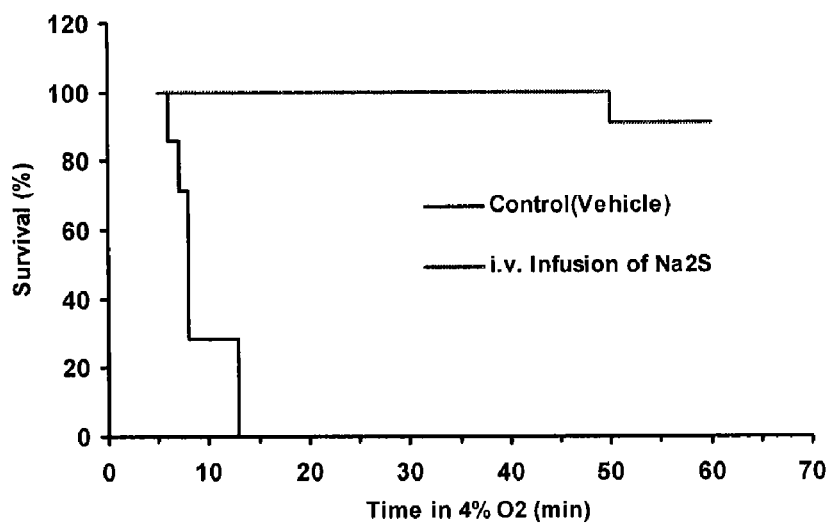
FIG. 10 is a Kaplan Meier graph comparing the survival rate measured over time of C57BL/6 mice exposed to hypoxia (4% $O_2$) that were either infused with vehicle or treated with infused $Na_2S$ (Liquid Pharmaceutical Composition I).

The mouse was infused with an effective dose of 0.8 mM/kg $H_2S$ of Liquid Pharmaceutical Composition I over a period of 60 minutes at an infusion rate of 6.4 µL/min until the temperature chip implanted in the skin registered a body temperature of 33° C., (FIG. 9). The infusion was then stopped, and the animal was placed into a hypoxic atmosphere (4.0% $O_2$) within one minute. At the end of one hour, the mouse was removed from the hypoxic chamber and placed in a cage and monitored. The mouse exhibited no signs of distress post-treatment. In contrast, a mouse treated with control vehicle died (FIG. 10).

In a second experiment, a mouse (ID: MCAT08) was infused with $Na_2S$, pH 8.2 (Liquid Pharmaceutical Composition II). Liquid Pharmaceutical Composition II was prepared by diluting a saturated stock of $Na_2S$ in deionized, deoxygenated $H_2O$ to a concentration of 41 mM, and deoxygenating the solution by dissolving with 100% $N_2$ while stirring for 30 minutes in a 3-necked flask with ground fittings. NaCl was added to adjust the final osmolarity of the solution to 300 mOsmol/L. The pH was adjusted by dissolving with a 50/50 mixture of $N_2$ and $CO_2$. The final solution (Liquid Pharmaceutical Composition II) was dispensed with minimal exposure to air into amber vials or bottles using minimal headspace and sealed with caps using Teflon/silicon liners or septa.

The mouse was infused over a period of 62 minutes at an initial infusion rate of 8 µL/min. After 30 minutes infusion, the infusion was decreased to 4 µL/min due to observed signs of distress. After 12 minutes infusion at 4 µL/min, the infusion rate was increased to 6 µL/min until the body temperature dropped to 33° C. The infusion was stopped, and the animal was placed into a hypoxic atmosphere (4.0% $O_2$) within 5 minutes. The mouse survived in the hypoxic atmosphere for 60 minutes.

In a third experiment, a mouse (ID: MJVC03) was infused with a $Na_2S$ (buffered with $H_2S$ and Nitrogen), Liquid Pharmaceutical Composition III, pH 8.35. In this example, Liquid Pharmaceutical Composition III was prepared by diluting a saturated stock of $Na_2S$ to 65 mM and deoxygenating the diluted solution by dissolving with 100% $N_2$ while stirring 30 minutes in a 3-necked flask with ground glass fittings, and pH adjusting the solution by dissolving with a 50/50 mixture of $N_2$ and $H_2S$. The final solution (Liquid Pharmaceutical Composition III) was dispensed with minimal exposure to air into amber vials or bottles using minimal headspace and sealed with caps using Teflon/silicon liners or septa.

The mouse was infused with $Na_2S$ (buffered with $H_2S$ and Nitrogen), Liquid Pharmaceutical Composition III, over a period of 60 minutes at an infusion rate of 4.3 µL/min. When the body temperature dropped to 33° C., the infusion was stopped, and the animal was placed into a hypoxic atmosphere (4.0% $O_2$) within 1 minute. The mouse survived 53 minutes at 4.0% hypoxia.

In contrast to the results obtained when the mice were treated with liquid $H_2S$, control (naïve) male C57BL/6 mice (average weight 22 grams) infused with vehicle (10 µL/min) survived on average for only 7 minutes in 4.0% $O_2$, with an average temperature drop of only 0.06±0.38° C.

In another experiment, the protective effect of a liquid pharmaceutical composition (50 mM $H_2S$) (Liquid Pharmaceutical Composition IV), pH 7.9, was tested in a cannulated male Sprague Dawley rat (RJVC40) (310 grams, Taconic) that was naïve to any experimental compounds. The animal was surgically implanted with an in-dwelling vascular catheter and was examined for signs of stress and disease prior to any procedure. The animal was weighed prior to procedures and weights were noted on the cage card. An IPTT-300 transponder from Bio Medic Data Systems (BMDS) was used to monitor body temperature. The transponder was injected subcutaneous (S.C.) into the back of the animal at least 24 hours prior to the experiment. A DAS-6008 data acquisition module from BMDS recorded body temperature of the rat via the transponder, and data was input into a computer spreadsheet and plotted against time.

The rat was infused through the in-dwelling catheter with 50 mM $H_2S$ (Liquid Pharmaceutical Composition IV), pH 7.9, over a period of 283 minutes using an infusion pump (Harvard Apparatus) while being monitored for signs of distress and decrease in body temperature as measured by an IPTT-300 transponder implanted subcutaneously. The starting infusion rate was 6.5 µL/min, which was increased by 6.5 µL/min every 15 minutes until the temperature chip implanted in the skin registered a body temperature of 33° C. The infusion was stopped for 10 minutes when the animal showed signs of distress and was restarted at a rate 13.0 µL/min lower than the previous rate. When the body temperature dropped to 33° C., the infusion was stopped, and the animal was placed into a hypoxic atmosphere (3.5% $O_2$) within 8 minutes. The animal survived for 32 minutes. Measured body temperature dropped 2.5° C. in the hypoxic chamber.

A control group of four (naïve) male SD rats (average weight 342 grams; Harlan) survived an average of 15±4 minutes in 3.5% $O_2$, with an average body temperature drop of 1.6±0.2° C.

These experiments establish that liquid pharmaceutical compositions of hydrogen sulfide have a protective effect on animals, which enhances their ability to survive under hypoxic conditions. This result further establishes that the administration of liquid pharmaceutical compositions of $H_2S$ are beneficial to patients suffering from or at risk of suffering from hypoxic or ischemic conditions, e.g., induced by injury or disease, and provides a means of protecting and preserving biological material from hypoxic or ischemic injury.

EXAMPLE 8

Liquid Pharmaceutical Composition of Sulfide Provides Cytoprotective Benefit from Hepatic Injury in the Murine Hepatic Ischemia-Reperfusion Injury Model The ability of a liquid pharmaceutical composition of sulfide to provide cytoprotective benefit in a model of hepatic ischemia-reperfusion (I/R) injury was tested in mice. In this study, it is demonstrated that intraperitoneal bolus administration of Liquid Pharmaceutical Composition IV (sulfide, 95 mM, pH 7.92) post-hepatic ischemia and immediately prior to a five hour reperfusion period decreased liver transaminases aspartate aminotransferase (AST) and alanine aminotransferase (ALT) measured in serum and improved histopathology scores. In contrast, treatment with vehicle did not provide any protective benefits in the hepatic I/R injury.

The mice used in these studies were C57-BL6/J mice, 8-10 weeks, (Jackson Laboratory, Bar Harbor, Me.). Food and water were provided ad libitum. Test animals were allowed to acclimate in a temperature and humidity controlled environment prior to the commencement of experimental procedures.

Mice were anesthetized with ketamine and xylazine and maintained with warming during surgical procedures to induce hepatic ischemia-reperfusion (I/R) injury. Specifically, a midline incision was performed to expose the liver and heparin was injected to prevent blood clotting. Both hepatic artery and portal vein were clamped with microaneurysm clamps to render the left lateral and median lobes of the ischemic liver. Ischemia proceeded for 45 minutes, with the liver maintained in the peritoneal cavity in its original location and kept moist with gauze soaked with 0.9% normal saline. Control mice received sham surgeries, although hepatic blood flow was not reduced with a microaneurysm clamp. At the end of 45 minutes, microaneurysm clamps were removed. Serum liver transaminase levels (AST or ALT) were tested after five hours hepatic reperfusion using spectrophotometry and commercially available reagents (Sigma-Aldrich).

Murine hepatic ischemia-reperfusion injury test animals were randomized to four groups. Group 1: vehicle treated; Group 2: treatment 0.3 mg/kg liquid pharmaceutical composition IV; Group 3: treatment 1.0 mg/kg liquid pharmaceutical composition IV and Group 4: treatment 3.0 mg/kg liquid pharmaceutical composition IV. As shown in FIG. 11, AST levels achieved statistically significant reduction at the highest tested concentration (3.0 mg/kg). ALT levels were reduced in the three treatment groups (0.3 mg/kg, 1.0 mg/kg, and 3.0 mg/kg), compared to vehicle.

EXAMPLE 9

Liquid Pharmaceutical Composition of Sulfide Provides Cardioprotective Benefit in the Murine Myocardial Ischemia Reperfusion Model The ability of a liquid pharmaceutical composition of sulfide to provide cardioprotective benefits in a myocardial ischemia-reperfusion (I/R) injury model was tested in mice. In this study, it is shown that bolus administration of Liquid Pharmaceutical Composition IV (95 mM, pH 7.65) into the left ventricular cavity post-ischemia and five minutes prior to a 24 hour reperfusion period reduced myocardial ischemia and reduced myocardial infarct size as a percentage of risk area. In a related study, administration of a pre-conditioning bolus dose of Liquid Pharmaceutical Composition IV 24 hours prior to initiation of the study significantly reduced myocardial infarct size (as a percentage of risk area) (myocardial infarction) (FIG. 16). In contrast, treatment with vehicle did not provide any protective benefits in the myocardial I/R injury.

The mice used in these studies were C57-BL6/J mice, 8-10 weeks, (Jackson Laboratory, Bar Harbor, Me.). Food and water were provided ad libitum. Test animals were allowed to acclimate in a temperature and humidity controlled environment prior to the commencement of experimental procedures.

Mice were anesthetized with ketamine and pentobarbital sodium and maintained with warming during surgical procedures to induce myocardial ischemia-reperfusion (I/R) injury. Mice were placed on a surgical board ventral side, orally intubated and connected to a Model 683 rodent ventilator (Tidal volume: 2.2 mLs, respiratory rate: 122 breaths per minute with 100% oxygen supplementation via the ventilator side port.) (Harvard Apparatus). The chest was opened and the proximal left main coronary artery was exposed and ligated. Myocardial and coronary artery occlusion was maintained for 30 minutes, followed by removal of the suture and reperfusion for 24 hours.

After 24 hours of reperfusion, post-ischemia, mice were anesthetized, intubated, and connected to a rodent ventilator. Evans blue dye was injected into a catheter threaded in the common carotid artery. A median sternotomy was performed and the left main coronary artery was re-ligated in the same location as previously. The separation of the ischemic zone from nonischemic zone was visualized with Evans Blue dye, the heart was rapidly excised and serially sectioned along the short axis in five 1-mm sections that were incubated in 1.0% 2,3,5-triphenyltetrazolium chloride (Sigma-Aldrich) for five minutes at 37° C. to separate of the viable and nonviable myocardium within the risk zone. Each of the five myocardial slices (1-mm) were weighed, areas of infarction, area at risk (AAR), and non-ischemic left ventricle were assessed with computer-assisted planimetry by an observer blinded to sample identity. All of the procedures for the left ventricular area at risk (AAR) and infarct size determination (see: Jones, S. P. et al. Am. J. Physiol. Heart Circ. Physiol. (2004)). 286: H276-H282).

Data were analyzed by 2-way ANOVA with post-hoc Bonferroni analysis using StatView software version 5.0 (SAS Institute). Data are reported as mean±SEM. p values less than 0.05 were considered significant.

Murine myocardial ischemia reperfusion model test groups of 10-13 animals were randomized to four treatment groups. Group 1: vehicle treated; Group 2: treatment with 50 µg/kg Liquid Pharmaceutical Composition IV; Group 3: treatment with 100 µg/kg Liquid Pharmaceutical Composition IV; and Group 4: treatment with 500 µg/kg Liquid Pharmaceutical Composition IV. In this study, bolus administration of Liquid Pharmaceutical Composition IV (97 mM, pH 7.65) into the left ventricular cavity of 30 minutes ischemia and five minutes prior to a 24 hour reperfusion period reduced myocardial infarct size as a percentage of risk area in treatment groups administered doses of 50 µg/kg and 100 µg/kg (FIG. 12). Four animals survived treatment at the highest tested concentration (500 µg/kg). Vehicle did not provide any protective benefits in the myocardial I/R injury.

In a second experiment, animals were pre-treated (preconditioning dose) with a bolus dose of liquid pharmaceutical composition IV, 24 hours prior to surgery and ischemia. Pretreatment with Liquid Pharmaceutical Composition provided protection against myocardial necrosis (100 µg/kg) as measured by a significant reduction in infarct size (FIG. 16).

EXAMPLE 10

Method and Use of Liquid Pharmaceutical Composition IV to Induce Mild Hypothermia in a Large Mammal It has been previously demonstrated that Liquid Pharmaceutical Compositions I, II, III, and IV suppressed core body temperature in a rodent (Example 7). Induction of mild hypothermia has been used in cardiac arrest, as a neuroprotectant from global ischemia in patients during cardiac surgery and to diminish reperfusion injury (see: Nolan et al., Circulation. (2003), 108:118-1210). In this study, the hypothesis that Liquid Pharmaceutical Composition IV reduces body temperature in a large animal in a model of mild hypothermia was confirmed. Liquid pharmaceutical composition IV was administered to two cohorts of female pigs over 60 minutes and the rate of change of body temperature over time was measured.

Female pigs (20-25 kgs) were housed with appropriate care as described in the Guide for the Care and Use of Laboratory Animals. Environmental controls were set to maintain a temperature of 61 to 81° F. and a relative humidity of 30 to 70%. A 12-hour light/dark cycle was employed and the room underwent a minimum of ten fresh air changes/hour.

Animals were anesthetized with a combination of ketamine (20 mg/kg) and xylazine (2.0 mg/kg) administered intramuscularly (IM). Each animal was then immediately intubated and maintained under anesthesia with inhalant isoflurane (0.5-2.5%). Inhalant anesthetic was delivered through either a volume-regulated respirator or re-breathing apparatus. An intravenous catheter was placed in jugular vein for administration of lactated Ringer's solution (10 ml/kg/hr) and any necessary emergency drugs (drug, dose, route, and site of administration were documented in the surgical file). Isoflurane concentration, oxygen rate, $SaO_2$%, pulse rate, respiration rate, and capillary refill time were recorded manually every 15 minutes. Blood pressure and EKG were monitored throughout the study. Core Body Temperature was monitored by use of an esophageal temperature probe that was inserted into the esophagus of the animal to acquire core body temperature.

Two cohorts of 5-6 animals were anesthetized as described. EKG, arterial blood pressure and core (abdomen) temperature were measured. Animals were maintained under anesthesia for a thirty minute baseline period. Following the 30 minute baseline period, test pigs were infused (2.5 mg/kg/hr) for 60 minutes with Ringer's solution and through a separate intravenous line, vehicle or Ringer's solution and through a separate intravenous line, Liquid Pharmaceutical Composition IV. Animals were observed during the 60 minute infusion period. Core temperature was measured at one second intervals. At the end of 60 minutes, animals were observed for thirty minutes prior to recovery from anesthesia.

Core temperatures were recorded from a temperature probe positioned in the abdomen, immediately below the liver. Data were acquired directly to computer using PowerLab data acquisition instrumentation and software. Data points recorded during the 1-hour infusion of ice cold Ringer's lactate was exported to GraphPad Prism software for regression analysis.

Group means were computed for total temperature change and speed of change (regression line slope) and were compared by Student's T-test.

These experiments establish that in pigs (20-25 kgs), Liquid Pharmaceutical Composition IV enhances the degree of hypothermia induced by a hypothermia-inducing treatment. Administration of Liquid Pharmaceutical Composition IV produced a statistically significant change in core body temperature when compared to vehicle (FIGS. 13A and 13B). The data demonstrate that Liquid Pharmaceutical Composition IV is effective in inducing hypothermia in a large animal.

EXAMPLE 11

Liquid Pharmaceutical Composition IV Reduces Regional Ischemia in a Myocardial Infarction Model in the Pig The ability of a liquid pharmaceutical composition of sulfide to provide cardioprotective benefits in a myocardial ischemia-reperfusion (I/R) injury model was tested in pigs. In this study, it is shown that bolus administration followed by 60 minutes infusion of Liquid Pharmaceutical Composition IV (100 mM, pH 7.80, 292 mOsm) into the left ventricular cavity post-ischemia (beginning five minutes prior to a 120 minute reperfusion period) reduced myocardial ischemia and reduced myocardial infarct size as a percentage of risk area. In contrast, treatment with vehicle did not provide any protective benefits in the myocardial I/R injury model.

Animals were housed individually. Food and water were provided ad libitum. All experiments conformed to the U.S. National Institutes of Health guidelines regulating the care and use of laboratory animals.

Pigs of either sex (35 to 45 kg) were sedated with ketamine hydrochloride (20 mg/kg), intramuscularly, and anesthetized with sodium pentobarbital (25 mg/kg), intravenously. General anesthesia comprised of isoflurane was maintained throughout the experiment. Ventilation (oxygen, 40%; tidal volume, 1000 mL; ventilation rate, 12 breaths/min; positive end-expiratory pressure, 3 cm $H_2O$; inspiratory to expiratory time ratio, 1/2) was provided via endotracheal intubation using a volume-cycled ventilator. The right femoral vein was cannulated for intravenous access and IV injection and the right common or superficial femoral artery was cannulated for arterial blood sampling and intra-arterial blood pressure monitoring. Heparin sodium and 1% lidocaine were administered before thoracotomy. Heparin was administered every 30 minutes to the end of the experiment. The pericardial sac was exposed through a median sternotomy and was opened to form a pericardial cradle. A catheter-tipped manometer was introduced through the apex into the left ventricle (LV) to record LV pressure. A vessel loop was threaded around the distal third of the left anterior descending coronary artery or its large diagonal branch after appropriate vessel exposure. The coronary artery was occluded by tightening the vessel loop, which was then secured by clamping with a mosquito clamp. Myocardial ischemia was confirmed visually by regional cyanosis of the myocardial surface.

Pigs were randomly divided into groups and subjected to 45 minutes regional ischemia (occlusion) followed by 120 min reperfusion. Arterial pressures (systolic pressure, diastolic pressure, mean blood pressure), heart rate, percent segmental shortening (LV dP/dt) and myocardial tissue flow were continuously acquired throughout the experiment (PONE-MAH digital data acquisition system, Gould, Valley View, Ohio), with an Acquire Plus processor board, and left ventricular pressure analysis software, and a Gould ECG/Biotach. Liquid Pharmaceutical Composition IV or vehicle were administered beginning 5 minutes prior to the start of removal of the coronary artery clamp (bolus (100 mcg/kg) and 1 mg/kg/h infusion) with the infusion continuing for 60 minutes during the reperfusion period.

Regional myocardial function was assessed by sonomicrometry (Sonometrics Corp., London, ON, Canada) using ultrasonic probes (2.0 mm) implanted in the subendocardial layer approximately 10 mm apart within the ischemic area, with two pairs placed parallel to the minor axis of the heart and secured to the epicardium with polypropylene stitches (Ethicon, Inc., Somerville, N.J.). The probes were left in place until the end of the experiment. Digital data was inspected for correct identification of end-diastolic and end-systolic points using post-processing software (SonoView, Sonometrics Corp., London, ON, Canada). Measurements were made over at least three cardiac cycles in normal sinus rhythm and then averaged. The ventilator was stopped during data acquisition to eliminate the effects of respiration. End-diastolic segment length (EDL) was measured at the onset of positive LV dP/dt, and the end-systolic segment length (ESL) at peak negative dP/dt. Regional contractility was assessed by segment shortening (SS). Wall motion abnormalities were assessed as systolic bulging (SB) defined as the bulging of the myocardium after the end of diastole. Postsystolic shortening (PSS) is the shortening after the end of systolic ejection. Time course changes in % SS were calculated from the mean±SEM of 4-5 unique horizontal and/or longitudinal distances and expressed as a percent of baseline to minimize variability among individual animals. Time course changes in SS were expressed as a percentage of equilibrium values to minimize variability among individual animals.

Blood gases and hematocrit were monitored every 10-15 min using a Corning 238 pH/blood gas analyzer and a Corning 270 CO-oximeter. Blood gases and acid-base parameters were maintained at $PO_2$>100 mmHg; pH—7.3±0.3; and temperature –37° C.

Ischemic area at risk was delineated by monastryl blue pigment injection into the aorta after ligation of the involved artery following the end of the experiment. Infarct size was determined by triphenyl tetrazolium chloride staining (Sigma Chemical Co.), and was expressed as a percentage of area at risk. The area at risk and the area of infarct zone were measured by computerized planimetry (Scion Image, Scion Corp., Frederick, Md.).

Myocardial tissue samples (approximately 0.5 g) from the area at risk (ischemic zone) and non-ischemic area of left ventricle (control zone) consisted of epicardial, myocardial and endocardial tissue that were removed at the end of each experiment and divided into two samples. Ischemic and non ischemic zone samples were confirmed by monastryl blue pigment injection. The samples were snap frozen or embedded as required.

Blood samples were collected and centrifuged and/or stored on ice. Statistical analysis was performed using SAS (SAS Institute, Inc., Cary, N.C.). The mean±SEM is shown for all variables. Statistical significance was determined by repeated measures analysis of variance (ANOVA) with the group as a "between subjects" factor and time as a "within subjects" factor. Post-hoc comparisons between groups for both the average effect and at individual time points were made with the use of a Bonferroni correction to adjust for the multiplicity of tests. Statistical differences between groups in infarct size were evaluated by ANOVA. Linear regression analysis was performed to determine the relation between segment shortening, infarct size and regional ischemic time in each group. Differences in regression lines between groups were compared using the general linear model. The general linear model was also used to test for significant non-linear (e.g. quadratic) effects. Statistical significance was claimed at $p < 0.05$.

In this study, bolus administration of Liquid Pharmaceutical Composition IV followed by 60 minute infusion into the left ventricular cavity 45 minutes ischemia and five minutes prior to a 120 minute reperfusion period reduced myocardial infarct size as a percentage of risk area (FIG. 14). Vehicle did not provide any protective benefits in the myocardial I/R injury.

EXAMPLE 12

Liquid Pharmaceutical Composition IV Preserves Cardiac Function Following Cardiopulmonary Bypass in Dogs To date, the major part of routine cardiac surgery is performed using extracorporal circulation with cardioplegic arrest. Even if cardiac dysfunction is not clinically evident, a reduction of myocardial contractility may occur as described in a human study using pressure-volume relationships. In addition, coronary endothelial and peripheral vascular dysfunction may further complicate the postoperative course. Extracorporal circulation is also known to induce a systemic inflammatory reaction with free radical release leading to secondary organ injury.

There is emerging evidence that hydrogen sulfide can exert cardioprotective effects in cultured myocytes, in perfused hearts and in rodent models of myocardial infarction (see, e.g., Pan, T. T. et al., J. Mol. Cell. Cardiol. 40:119-30 (2006); Bian, J. S. et al., J. Pharmacol. Exp. Ther. 316:670-8 (2006); Johansen, D. et al., Basic Res. Cardiol. 101:53-60 (2006); and Zhu, Y. Z. et al., J. Appl. Physiol. 102:261-8 (2007)). Mechanisms of sulfide protection include conservation of cellular energetics, down-regulation of inflammatory pathways, cytoprotection due to antioxidant effects. In the present study, the potential cardioprotective effect of a liquid pharmaceutical composition of $H_2S$ was tested in a dog model of cardiopulmonary bypass, to determine whether the compound affects cardiovascular function in a clinically relevant model of bypass surgery. In addition, the effect of hydrogen sulfide on vascular function and myocardial energetic status was determined.

The ability of a liquid pharmaceutical composition of sulfide to provide cardioprotective benefits during cardiopulmonary bypass was tested in two cohorts of dogs using an established model of cardiac arrest (ischemia; Szabo, G. et al., Eur. J. Cardiothorac. Surg. 25:825-32 (2004)). In this study, each animal underwent 90 minutes of cardiopulmonary bypass (CBP) (30 minutes CBP followed by 60 minutes of cardiac arrest) and 60 minutes reperfusion by restoration of arterial flow. Infusion of Liquid Pharmaceutical Composition IV during cardiac arrest and reperfusion preserved cardiac function as measured by preload recruitable stroke work (PRSW). In contrast, treatment with vehicle did not provide any cardioprotective benefits in the cardiac arrest (ischemia) model.

Dogs were randomized to two groups and received humane care in compliance with the guidelines of the National Society for Medical Research and National Institutes of Health. Dogs were premedicated with propionylpromazine, anesthetized with pentobarbital, maintained with pancuronium bromide and endotracheally intubated. Ventilation comprised a mixture of room air and $O_2$ at a frequency of 12-15/min and tidal volume starting at 15 ml/kg per minute. Arterial partial carbon dioxide pressure levels were maintained between 35-40 mmHg. The femoral artery and vein were cannulated to record aortic pressure (AoP) and to take blood samples for biochemical analysis. Basic intravenous volume substitution was carried out with Ringer's solution (1 ml/min/kg). According to the values of potassium, bicarbonate and base excess, substitution included administration of potassium chloride and sodium bicarbonate (8.4%). Neither catecholamines nor other hormonal or pressor substances were administered.

Test articles comprising either Liquid Pharmaceutical Composition IV (100 mM, pH 7.71, 292 mOsm) or vehicle were infused during the 60 minute cardiac arrest and 60 minute reperfusion period (1 mg/kg/h infusion).

The great vessels were dissected following left anterolateral thoracotomy. The left subclavian artery was cannulated for arterial perfusion and heparin administered to maintain anti-coagulation. A venous cannula was placed in the right atrium. The extracorporeal circuit (bypass) consisted of a heat exchanger, a venous reservoir, a roller pump and a membrane oxygenator primed with Ringer's lactate solution with heparin and sodium bicarbonate. After initiation of cardiopulmonary bypass (CPB), the animal body temperature was cooled to 28° C. The aorta was cross-clamped and the heart was arrested with 25 ml/kg HTK solution (in mmol: 15 NaCl, 9 KCl, 4 $MgCl_2$ $6H_2O$, 18 histidine hydrochloride monohydrate, 180 histidine, 2 tryptophan, 30 mannitol, 0.015 $CaCl_2$, 1 potassium-hydrogen-2-oxopentandioat, $H_2O$).

During cardiac arrest/perfusion, the pump flow was adjusted to maintain perfusion pressure above 35-40 mmHg. Re-warming was initiated at 40 minutes post-clamping and after 60 minutes of cardiac arrest, the aorta was de-clamped and the heart was re-perfused with blood in the bypass circuit. If necessary, ventricular fibrillation was counteracted with DC cardioversion of 40 J.

Following the study, ventilation was restarted with 100% oxygen. All animals were weaned from CPB without inotropic support 20 minutes after the release of the aortic cross clamp. Functional measurements were performed and recorded before CBP and after 60 minutes of reperfusion. In addition, myocardial probes were collected for high energy phosphate analysis at the end of experiments.

Left end right ventricular systolic (LVESP) and diastolic pressures (LVEDP) and volumes were measured by combined pressure-conductance catheters via the pulmonary artery, respectively. Stroke volume (SV) was calculated. Parallel conductance was estimated by rapid injection of one ml of hypertonic saline into the pulmonary artery or superior vena cava. Vena cava occlusions were performed to obtain a series of pressure-volume loops. The slope and intercept of the left and right ventricular end-systolic pressure-volume relationships and preload recruitable stroke work (PRSW) was calculated as load-independent indices of myocardial contractility.

Coronary blood flow was measured on the left anterior descendent artery with a perivascular ultrasonic flow probe. Coronary endothelium-dependent vasodilatation was assessed after intracoronary administration of a single bolus of acetylcholine (ACH, $10^{-7}$ M) and endothelium-independent vasodilatation after sodium-nitroprusside (SNP, $10^{-4}$ M). The vasoresponse was expressed as percent change of baseline coronary vascular resistance.

Cardiac contractile function was measured by pressure-volume loop analysis following reperfusion. Infusion with either vehicle or Liquid Pharmaceutical Composition IV was initiated 30 minutes after CBP and continued until the end of the experiments (2 hours infusion in total, at a dose of 1 mg/kg/hour, i.v.). All animals were subjected to 60 minutes of cardiac arrest (ischemia) and a total cardiopulmonary bypass time of 90 minutes. Preload recruitable stroke work (PRSW) declined in the group treated with vehicle in response to ischemia. Infusion of Liquid Pharmaceutical Composition IV during cardiac arrest and reperfusion was cardioprotective as measured by the change preload recruitable stroke work (PRSW) compared to baseline (FIG. 15).

Adenosine triphosphate (ATP), adenosine diphosphate (ADP) and adenosine monophosphate (AMP) contents were assessed with standard photometry using an enzyme-kinetic assay. In addition endothelium-dependent and -independent relaxation was investigated in isolated coronary rings. After the end of the in vivo experiments the hearts were excised and the coronary arteries were isolated and placed in cold (+4° C.) Krebs-Henseleit solution (118 mM NaCl, 4.7 mM KCl, 1.2 mM $KH_2PO_4$, 1.2 mM $MgSO_4$, 1.77 mM $CaCl_2$, 25 mM $NaHCO_3$, 11.4 mM glucose; pH=7.4). The coronary arteries were prepared and cleaned from periadventitial fat and surrounding connective tissue and cut transversely into 4-mm width rings using an operation microscope. Isolated aortic rings were mounted on stainless steel hooks in individual organ baths (Radnoti Glass Technology, Monrovia, Calif., USA), containing 25 ml of Krebs-Henseleit solution at 37° C. and aerated with 95% $O_2$ and 5% $CO_2$. Special attention was paid during the preparation to avoid damaging the endothelium. Isometric contractions were recorded using isometric force transducers (Radnoti Glass Technology, Monrovia, Calif., USA), digitized, stored and displayed with the IOX Software System (EMKA Technologies, Paris, France). The rings were placed under a resting tension of 2 g and equilibrated for 60 minutes. U46619 ($5\times10^{-7}$ M) was used to precontract the rings until a stable plateau was reached, and relaxation responses were examined by adding cumulative concentrations of endothelium-dependent dilator acetylcholine (ACh, $10^{-9}$-$10^{-4}$ M) and endothelium-independent dilator sodium nitroprusside (SNP, $10^{-10}$-$10^{-5}$ M). Relaxation is expressed as percent of contraction induced by U46619.

Heart rate (HR), MAP, CO and CBF are shown in Table 2. Baseline heart rate was somewhat higher in the treatment groups; otherwise, no differences could be documented. MAP showed a decreasing tendency in all three groups after CPB, which was significant in both treatment groups (p<0.05). CO showed no major differences between the groups and over the time. CBF was comparable in all three groups at baseline. It decreased significantly in the control group after CPB while it remained unchanged in both treatment groups. Hemodynamic variables did not differ between the groups and over the time.

Baseline values related to left ventricular function did not differ between the groups. After CPB, both left ventricular dP/dt and PRSW decreased significantly in the control group, which was partly reversed by $H_2S$ (FIGS. 15 and 17).

Before CPB, no differences have been observed in endothelial function in vivo. After CPB the response to acetylcholine was significantly reduced in the control group, which was partly abolished by $H_2S$ (FIG. 19.). The response to SNP did not differ between the groups and over the time.

The endothelium-dependent vasorelaxation of the precontracted coronary arterial rings to acetylcholine (ACh) was significantly impaired in comparison to control rings (animals without CPB, historic control) and was completely prevented in the $H_2S$ treated group (FIG. 19). Endothelium dependent vasorelaxation after SNP did not differ between the groups.

Myocardial ATP measurements taken at the end of the experiments were significantly increased in the presence of hydrogen sulfide as compared to control vehicle. However, ADP and AMP levels remained comparable (Table 3).

These data demonstrate that treatment with liquid formulations of $H_2S$ improves postischemic myocardial and endothelial function after cardioplegic arrest in the setting of cardiopulmonary bypass in a large animal model. These beneficial effects may be due to $H_2S$'s antioxidant, anti-inflammatory, hemodynamic and cytoprotective effects, or a combination thereof.

EXAMPLE 13

Hydrogen Sulfide Reduces DNA Damage from Aortic-Occlusion-Induced Ischemia-Reperfusion Injury The effect on metabolic response and the cytoprotective effect of infusing the $H_2S$-donor NaHS was examined in a clinically relevant porcine model of thoracic aortic occlusion-induced ischemia/reperfusion (I/R) injury. The ability of sulfide to influence the noradrenaline responsiveness during reperfusion after aortic occlusion was also determined.

After random assignment to either NaHS (n=8; 0.2 mg/kg followed by 2 mg/kg×h started 2 hours before aortic occlusion and continued until 8 h of reperfusion) or vehicle (n=8), anesthetized, ventilated and instrumented pigs underwent 30 minutes of aortic occlusion using inflatable balloons placed immediately downstream the A. subclavia and upstream the aortic bifurcation. During aortic occlusion, mean arterial pressure (MAP) was maintained between 80-120% of the pre-occlusion levels using i.v. esmolol, nitroglycerine and ATP. During the early reperfusion period continuous i.v. noradrenaline was titrated to maintain MAP>80% of the baseline level.

As described in further detail below, sulfide reduced heart rate and cardiac output without affecting stroke volume, markedly decreased the time and dose of noradrenaline required to maintain hemodynamic targets, and caused a drop in core temperature concomitant with lower $O_2$ uptake and $CO_2$ production. While arterial $PCO_2$ and acid-base status were comparable, arterial $PO_2$ was lower in the sulfide-group at the end of the experiment. Sulfide attenuated the reperfusion-related hyperlactatemia, while glycemia was higher at the end of the experiment. The parameters of inflammation and oxidative stress did not differ.

Experimental Procedures

The experiments were performed in adherence to National Institute of Health Guidelines on the Use of Laboratory Animals. The experimental protocol had been approved by the University Animal Care Committee and the Federal Authorities for animal research. Sixteen domestic pigs of either sex with a median (range) body weight of 44 (42-54) kg were used. Sodium sulfide ($Na_2S$) for parenteral injection was produced by Ikaria Inc. (Seattle, Wash.) using $H_2S$ gas (Matheson, Newark, Calif.) as the starting material, which was bubbled through an aqueous solution of NaOH and NaCl, and formulated to pH neutrality and iso-osmolarity. The solution was then filtered and vialed under inert gas atmosphere.

After induction of anaesthesia with i.v. propofol (3-5 mg·kg–1) and ketamine (1-2 mg·kg–1) and endotracheal intubation, anesthesia was maintained with continuous i.v. propofol (6-8 mg·kg–1·h–1) and remifentanil (15-20 µg·kg–1·h–1). Pigs were mechanically ventilated ($FiO_2$ 0.35, tidal volume 8 mL·kg–1, PEEP 10 $cmH_2O$, respiratory rate adjusted to maintain arterial $PCO_2$ 35±4 mmHg) using ventilator settings that were kept constant throughout the experiment. Via surgical cut downs, catheters were placed in the carotid artery and the jugular vein. Femoral cut downs allowed introducing catheter sheaths into the left and the right femoral artery for placement of inflatable balloon catheters. Adapting a technique published previously (Kick J., et al., *Intensive Care Med* 33:694-702, 2007; and Annecke T., et al., *Br J Anaesth* 98:581-590, 2007), one catheter was placed directly above the aortic bifurcation, the other one directly downstream of the Arteria subclavia sinistra, the correct position of which was manually controlled via a left sided thoracotomy. Room temperature was kept at 24-26° C., and all animals were continuously heated using a mattress set to 39° C. in order to avoid any effects of profound hypothermia per se.

The following parameters were recorded continuously: heart rate; arterial and central venous pressure; cardiac output (pulse contour analysis [29]) and global end-diastolic volume (transpulmonary thermodilution), a well-established surrogate of cardiac preload (PiCCO®, Pulsion Medical Instruments); body temperature; $O_2$ uptake and $CO_2$ production (indirect calorimetry; Deltatrac II Metabolic Monitor®, GE Datex Ohmeda). Intermittent arterial blood samples were analyzed for blood gases, acid-base status, hemoglobin content and $O_2$ saturation, 8-isoprostane (8-epiprostaglandin $F_2$, a marker of lipid peroxidation), plasma TNF-α and nitrate plus nitrite (a surrogate of nitric oxide production [33]) concentrations. The latter were normalized for protein content to correct for dilution effects of fluid administration. Oxidative DNA damage in whole blood cells were quantified with the alkaline version of the comet assay that allows detecting DNA strand breaks.

After baseline measurements, animals randomly received either sulfide (initial bolus 0.2 mg·kg$^{-1}$ followed by continuous i.v. 2 mg·kg$^{-1}$·h$^{-1}$ until the end of the experiment; n=8: seven males, one female) or its vehicle saline (n=8: six males, two females). After another data set at two hours of infusion, the aorta was occluded for 30 minutes by inflating the two intra-aortic balloons. This duration of aortic occlusion was chosen because in previous experiments, it had resulted in only little organ injury but marked hypotension and, consequently, the need for catecholamine support during the early reperfusion period. Thus, it allowed investigating the hemodynamic and metabolic effects as well as the noradrenaline responsiveness of sulfide in the absence of a major I/R-induced inflammatory response. To ensure constant fluid administration, animals received 10 mL·kg$^{-1}$·h$^{-1}$ of Ringer's solution throughout the whole experiment. In order to optimize preload 1000 mL of hydroxyethyl starch were infused during aortic occlusion. Continuous i.v. nitroglycerine (1.7 mg mg·min$^{-1}$), esmolol (16.5 mg·min$^{-1}$) and adenosine-5'-triphosphate (ATP, 2-10 mg·min$^{-1}$) was infused during aortic occlusion and adjusted to maintain mean arterial pressure at 80-120% of the baseline value. During the early reperfusion period continuous i.v. noradrenaline was titrated to keep mean arterial pressure $\geq$80% of the value prior to aortic occlusion. Additional data was collected at one, two, four and eight hours of reperfusion. Thereafter, the animals were sacrificed under deep anaesthesia with i.v. Na-pentobarbitone and KCl. DNA damage in whole blood samples was evaluated with single cell gel electrophoresis (alkaline comet assay).

Results

All data were presented as median (range). After exclusion of normal distribution using the Kolmogorov-Smirnov test, data within groups were analysed with a Friedman repeated measures ANOVA on ranks and a subsequent post hoc multiple comparison procedure (Dunn's method). Differences between treatment groups within one measurement point were analysed with the Mann-Whitney rank sum test for unpaired samples.

Sulfide caused a parallel fall in both heart rate and cardiac output (FIG. 20), and, thus, also attenuated the noradrenaline-related rise in cardiac output during early reperfusion (FIG. 21). Despite the markedly reduced time and dose of noradrenaline required to maintain target blood pressure (FIG. 21), stroke volume did not significantly differ over time and was even higher during early reperfusion in the sulfide-treated animals, albeit this difference did not reach statisticial significance (p=0.09 and p=0.07 vs. controls at one and two hours of reperfusion, respectively) (FIG. 20). Albeit the external heating was identical in all animals, core temperature dropped in both groups (FIG. 22). This effect became more pronounced, however, in the sulfide-animals until the end of the experiment and was associated with lower $O_2$ uptake and $CO_2$ production during the last six hours of reperfusion (FIG. 22). While arterial $PCO_2$ and acid-base status were comparable, arterial $PO_2$ was significantly lower in the sulfide-group at the end of the experiment (Table 5). Sulfide also attenuated the hyperlactatemia during early reperfusion, while glycemia was higher in this group at the end of the experiment (FIG. 23). None of the parameters of inflammation, oxidative stress and genotoxicity showed any intergroup difference (Table 5).

Treatment with sulfide blunted I/R-induced DNA damage. The DNA damage data obtained from an initial study are shown in Table 4 as the median (range), wherein group differences were tested with a Friedman ANOVA on ranks, and intergroup differences were tested with an unpaired rank sum test (tail moment in the comet assay, # p<0.05 vs. before infusion, §p<0.05 vs. vehicle). Additional DNA damage data is provided in Table 5.

Discussion

The present study characterized the hemodynamic and metabolic effects of infusing sulfide during short-term porcine I/R induced by aortic occlusion. Parenteral administration of sulfide—as opposed to inhaled $H_2S$ gas—has a number of practical advantages (ease of administration, no need for inhalation delivery systems, no risk of exposure to experimental personnel, no issues related to the characteristic odor of $H_2S$ gas), as well as avoids the undesired side effects of inhaled $H_2S$ which can be apparent even for low inspiratory gaseous concentrations. The key findings were that i) sulfide markedly reduced the catecholamine requirements needed to achieve the hemodynamic targets during early reperfusion, ii) sulfide induced a pronounced drop in core temperature concomitant with reduced $O_2$ uptake and $CO_2$ production, which, however, iii) did not coincide with any alteration of the parameters measured of inflammation, oxidative stress and genotoxicity.

While both mean arterial and central venous pressure were comparable in the two groups, the sulfide infusion was associated with a significantly lower cardiac output. In other words, systemic vascular resistance was markedly increased in this group, suggesting that the reduced noradrenaline requirements during the early reperfusion period were due to an improved vasoconstrictor response to the noradrenaline infusion. This finding is of particular interest since $H_2S$ was reported to be an endogenous vasodilator (Fiorucci S., et al., *Gastroenterology* 131:250-271, 2006; and Bhatia M., *IUBMB Life* 57:603-606, 2005), and intravenous $H_2S$ caused hypotension in various rodent models in vivo (Geng B. et al., *Biochem Biophys Res Comm* 31:362-368, 2004; and Zhao W. et al., *EMBO J.* 20:6008-6016, 2001). It should be noted, however, that in the present experiments arterial, $PO_2$ was always >100 mmHg during early reperfusion. In fact, at a 200 μM $O_2$ concentration in vitro, i.e. a $PO_2$ of approximately 150 mmHg, $H_2S$ exerted vasoconstrictor rather than vasodilator properties (which were present, however, at 40 μM $O_2$ concentrations, i.e. a $PO_2$ of approximately 30 mmHg), which was referred to the formation of a vasoactive oxidation product rather than $H_2S$ per se.

In these experiments, the significantly lower cardiac output was solely caused by a fall in heart rate, which is consistent with a previous report in spontaneously breathing mice, demonstrating that inhaling gaseous $H_2S$ allowed maintaining blood pressure and stroke volume whereas heart rate and cardiac output were reduced in parallel. It is noteworthy in this context that the markedly lower noradrenaline requirement and the shorter noradrenaline infusion time are also indicative of improved heart function; while the parameters of cardiac preload were similar in the two groups, stroke volume was even higher in the sulfide-treated animals at one and two hours of reperfusion, albeit this difference did not reach statistical significance. In all sulfide-treated animals, the noradrenaline was infused for less than one hour, i.e. in contrast to the control animals, this stroke volume was achieved without any inotropic support at those time points. These findings agree with a recent report in dogs that improved biventricular function, coronary blood flow and myocardial energy charge after cardiopulmonary bypass (Szabó C., et al., *Crit. Care* 11 suppl 2:S1, 2007). Hence, these data demonstrate that sulfide may also effectively improve heart function after visceral organ ischemia/reperfusion-injury, thereby mimicking the beneficial effects of sevoflurane inhalation in this model (Annecke T. et al., *Br J Anaesth* 98:581-590, 2007).

The sulfide-induced fall in heart rate and cardiac output was concomitant with a marked reduction in $O_2$ uptake, $CO_2$ production and core temperature, albeit the fluid and drug infusion rates were strictly identical during these last six hours of reperfusion. Thus, these experiment in large animals were consistent with data reported by Blackstone et al that inhaled $H_2S$ caused a "suspended animation"-like metabolic status in mice (Blackstone E., et al., *Science* 308:518, 2005; and Blackstone E., and Roth M. B., *Shock* 27:370-372, 2007). This reasoning is underscored by the higher glycemia at the end of the experiment as well as the less pronounced hyperlactatemia during the early reperfusion period. The latter is of particular importance, since the fall in $O_2$ uptake induced by inhaling low-dose gaseous $H_2S$ during exercise was associated with significantly higher blood lactate concentrations, indicating a shift to anaerobic glycolysis resulting from the inhibition of mitochondrial respiration. By contrast, in the present experiments, sulfide decreased the rate of metabolic expenditure and, thus, reduced both the need for anaerobic ATP generation during the ischemia period as well as the glucose turnover rate at the end of the experiment. Inhibition of cytochrome oxidase may assume importance in this context. The lower blood lactate levels agree with a putative role of $H_2S$-induced activation of mitochondrial $K_{ATP}$-channels: we previously showed in endotoxic swine that the $K_{ATP}$-channel blocker HMR1402 caused marked lactic acidosis, most likely resulting from inhibition of mitochondrial $K_{ATP}$-channels (Asfar P., et al., *Intensive Care Med* 30:957-964, 2004). It is most unlikely, however, that the lower noradrenaline infusion rate contributed to this observation, since $O_2$ uptake, $CO_2$ production and core temperature did not significantly differ between the two experimental groups until at least two hours of reperfusion, hence, when noradrenaline had been withdrawn in all animals irrespective of the group assignment.

It is well-established that gaseous $H_2S$ is a pulmonary irritant, even at low inspiratory concentrations. Therefore, in these experiments, we used the i.v. $H_2S$ donor $Na_2S$, Nevertheless, at the end of the experiment, arterial $PO_2$ was significantly lower in these animals, suggesting that some pulmonary toxicity was present. In fact, the last but one experimental animal presented with marked hypoxemia, and diffuse pulmonary hemorrhage was found at the post mortem inspection.

In conclusion, these studies demonstrate that intravenous sulfide allowed reducing energy expenditure in an anesthetised large animal model, and improved the noradrenaline responsiveness during reperfusion after aortic occlusion. The data establish that treatment with liquid sulfide formulations prevents ischemic injury of the heart, and further suggest that it may also protect other organs after ischemia/reperfusion injury. The beneficial effects may be due to a combination of the metabolic modulatory and cytoprotective effects of this compound.

TABLE 1

| Species | Disease Model | Drug | Vendor | Vehicle | Dose | Route of Admin. | Regimen | Benefit |
|---|---|---|---|---|---|---|---|---|
| male nh primates | erectile dysfunction | sodium hydrosulfide (NaHS) | Sigma | Saline | 0.25, 0.5, 1, 2, 5, 10, 20, 80 umol/kg | Intracaver. | before experiment | Increase intracavernous pressure |
| rat | Cerebral Ischemia | sodium hydrosulfide (NaHS) | Sigma | Water | 0.18 mmol/kg. | IP | 24 hours after MCAO | the infarct volume was increased to 150% of control-measure of response |
| rats | Irritable bowel syndrome, inflamation and pain | ATB-429 (mesalamine metab.) | Antibe | d-water | 25, 50, or 100 mg/kg | IP | 10 minutes post IBS model | Pain killing and some anti-inflammatory effects of a sulfide |
| rats | Gastric injury caused by NSAIDS | sodium hydrosulfide (NaHS) | Sigma | Water | 25, 50, 100, or 150 mol/kg | IP | treatment immediately prior | reduces injury produced by NSAID and ASA |
| rats | myocardial ischemia-reperfusion injury | NaHS•xH$_2$O (2 8-32% H$_2$O) | Fisher | Water | 0.1M, 1 um, 10 um NaHS | perfusion | 10 min prior to LCA occlusion | NAHS, limited infarct size in a well-characterised rat heart model of ischemia reperfusion |
| rats | reduce vascular calcification | NaHS | | | 2.8 or 14 uM/day | | daily | reduces vascular calcification induced by vitamin D3 plus nicotine |
| rats | myocardial ishemia-reperfusion injury | sodium hydrosulfide (NaHS) | Sigma | Saline | 3 mg/kg | IP | 15 min before LAD | cardioprotective opens KATP channels |

TABLE 1-continued

| Species | Disease Model | Drug | Vendor | Vehicle | Dose | Route of Admin. | Regimen | Benefit |
|---|---|---|---|---|---|---|---|---|
| rats | reduce neutrophil adhesion, leukocyte-mediated inflam. | NaHS and Na2S | Sigma | 1% carboxy-methyl-cellu. | 1-100 uMol/kg | IP | 30 min prior to cargeenan injection | inhibits inflammation |
| rats | liver cirrhosis | NaHS (1 mmol/L) | Sigma | saline | 56 umol/kg | IP | daily dose for five days | vasorelaxation in a model of liver cirrhosis |
| mouse | inflammation | NaHS | Sigma | saline | 1, 5 and 10 mg/kg | IP | 1-6 hours before study | Increases substance P levels - provides GPCR target for treatment |
| rats | cardio-protectant | NaHS | Sigma | saline | 2.8 umol/kg | IV | time zero | decrease central venous pressure in cardiovascular injection |
| rats | septic shock | Na2S and HCL | endog-enous | not applicable | not applicable | endogenous | measured following model | measured H2S in septic shock |

TABLE 2

|  | Before CBP control | H2S | After CPB control | H2S |
|---|---|---|---|---|
| HR (min$^{-1}$) | 114 ± 8 | 135 ± 7 | 130 ± 4 | 139 ± 8 |
| MAP (mmHg) | 104 ± 10 | 91 ± 9 | 86 ± 4 | 75 ± 16 |
| CO (l/min) | 3.22 ± 0.29 | 2.82 ± 0.27 | 2.73 ± 0.34 | 3.02 ± 0.21 |
| CBF (ml/min) | 40 ± 5 | 46 ± 5 | 24 ± 3# | 58 ± 17* |
| LVEDP [mmHg] | 10 ± 2 | 11 ± 1 | 11 ± 1 | 13 ± 2 |
| LVESP [mmHg] | 104 ± 9 | 113 ± 19 | 87 ± 3# | 95 ± 11 |

TABLE 3

|  | control | H$_2$S |
|---|---|---|
| ATP (μmol/g drw) | 9.1 ± 1.2 | 15.8 ± 0.9* |
| ADP (μmol/g drw) | 5.8 ± 0.4 | 5.4 ± 0.3 |
| AMP (μmol/g drw) | 1.4 ± 0.3 | 1.3 ± 0.2 |

TABLE 4

|  |  | Before infusion | Before clamping | 1 h after clamping | 2 h after clamping | 4 h after clamping | 8 h after clamping |
|---|---|---|---|---|---|---|---|
| Tail moment | Vehicle | 0.15 (0.09-0.20) | 0.125 (0.11-0.19) | 0.17 # (0.14-0.25) | 0.23 # (0.14-0.38) | 0.15 (0.08-0.24) | 0.13 (0.09-0.21) |
|  | NaHS | 0.125 (0.08-0.25) | 0.11 (0.08-0.13) | 0.12 § (0.04-0.24) | 0.12 § (0.09-0.32) | 0.14 (0.12-0.24) | 0.14 (0.11-0.18) |

TABLE 5

Hemodynamic, gas exchange, and acid-base and metabolic parameters

|  |  | Before aortic occlusion | | After aortic occlusion | | | |
|---|---|---|---|---|---|---|---|
|  |  | Before drug infusion | After 2 h drug infusion | 1 h | 2 h | 4 h | 8 h |
| MAP, mmHg | Control | 94 (85-111) | 97 (89-108) | 93 (82-99) | 95 (89-105) | 90 (84-96) | 89 (83-105) |
|  | Sulfide | 97 (92-103) | 99 (90-100) | 95 (86-97) | 92 (89-96) | 91 (86-103) | 94 (78-96) |
| Central venous pressure, (mmHg) | Control | 11 (8-14) | 10 (8-15) | 12 (6-13) | 12 (10-14) | 12 (11-15) | 12 (10-14) |
|  | Sulfide | 10 (8-14) | 10 (8-11) | 11 (9-13) | 10 (8-12) | 10 (9-13) | 12 (9-14) |
| Global end-diastolic Volume, mL | Control | 733 (650-1,073) | 645 (573-1,186) | 715 (653-1,304) | 690 (631-1,111) | 660 (604-1,256) | 692 (642-1,173) |
|  | Sulfide | 743 (568-791) | 731 (640-991) | 870 (760-1,007)* | 786 (653-947) | 747 (558-915) | 691 (503-1,089) |
| Pao$_2$, mmHg | Control | 152 (145-156) | 154 (150-159) | 127 (119-135)* | 128 (116-131)* | 132 (121-145)* | 144 (135-150)* |
|  | Sulfide | 150 (148-158) | 154 (152-158) | 114 (109-126)* | 134 (124-139)* | 140 (125-143)* | 92 (66-107)*† |

TABLE 5-continued

Hemodynamic, gas exchange, and acid-base and metabolic parameters

| | | Before aortic occlusion | | After aortic occlusion | | | |
|---|---|---|---|---|---|---|---|
| | | Before drug infusion | After 2 h drug infusion | 1 h | 2 h | 4 h | 8 h |
| $Paco_2$, mmHg | Control | 34 (31-38) | 34 (33-38) | 48 (39-52)* | 46 (39-51)* | 44 (37-48)* | 40 (38-40)* |
| | Sulfide | 37 (34-37) | 36 (35-38) | 44 (41-46)* | 40 (39-42)* | 37 (36-40) | 40 (37-45)* |
| Arterial pH | Control | 7.58 (7.56-7.62) | 7.55 (7.53-7.59) | 7.38 (7.30-7.44)* | 7.39 (7.29-7.51)* | 7.48 (7.41-7.53)* | 7.51 (7.48-7.53)* |
| | Sulfide | 7.58 (7.56-7.6) | 7.55 (7.53-7.57) | 7.42 (7.40-7.43)* | 7.48 (7.47-7.5)* | 7.51 (7.5-7.55)* | 7.49 (7.44-7.55)* |
| Arterial base excess, $mmol \cdot L^{-1}$ | Control | 11.4 (9.6-12.9) | 10.0 (8.5-11.2) | 0.6 (−0.4-4.5)* | 2.7 (−0.8-8.6)* | 8.3 (5.8-9.2)* | 8.1 (6.7-9.7)* |
| | Sulfide | 12.7 (10.1-13.1) | 10.4 (7.9-11.2) | 3.3 (2.5-5.2)* | 6.2 (5.3-7.7)* | 7.1 (6.4-9.6)* | 7.5 (6.0-9.4)* |
| DNA strand breaks, tail moment | Control | 0.14 (0.12-0.17) | 0.13 (0.12-0.18) | 0.16 (0.15-0.22) | 0.18 (0.14-0.27) | 0.14 (0.09-0.19) | 0.13 (0.12-0.18) |
| | Sulfide | 0.15 (0.09-0.13) | 0.12 (0.09-0.13) | 0.13 (0.11-0.17) | 0.15 (0.10-0.18) | 0.15 (0.13-0.19) | 0.14 (0.13-0.16) |
| TNF-α, $ng \cdot g_{protein}^{-1}$ | Control | 2.1 (1.4-2.4) | 2.0 (1.5-2.7) | ND | 2.8 (2.1-3.4) | 3.1 (2.4-3.4) | 3.6 (3.4-4.0)* |
| | Sulfide | 1.6 (1.5-1.8) | 1.8 (1.7-1.9)* | ND | 2.4 (2.2-2.8)* | 2.6 (2.4-2.9)* | 3.1 (2.5-3.9)* |
| Nitrate + nitrite, $\mu mol \cdot g_{protein}^{-1}$ | Control | 0.91 (0.37-1.48) | 0.82 (0.33-1.33) | ND | 0.94 (0.43-1.62) | 0.74 (0.52-1.57) | 0.79 (0.45-1.45) |
| | Sulfide | 1.05 (0.36-2.01) | 0.83 (0.4-1.99) | ND | 0.99 (0.23-2.37) | 0.75 (0.33-2.32) | 0.78 (0.10-1.76) |
| 8-Isoprostane, $ng \cdot g_{protein}^{-1}$ | Control | 1.1 (0.9-1.3) | 1.3 (1.2-1.3)* | ND | 1.6 (1.1-2.0)* | 1.4 (1.2-1.6)* | 1.7 (1.4-2.2)* |
| | Sulfide | 1.3 (1.1-1.4) | 1.3 (1.1-1.4) | ND | 1.5 (1.3-1.7) | 1.5 (1.4-1.7)* | 1.5 (1.4-2.0)* |

All data are median (range), n = 8 in each group.
*P < 0.05 vs. before drug infusion,
†P < 0.05 control vs. sulfide.
ND—not determined.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating disease, injury or a disorder in a biological material comprising contacting the biological material with an effective amount of a sterile, stable aqueous pharmaceutical composition comprising:
a solution of deoxygenated water and sodium sulfide;
wherein the sodium sulfide produces Na2S, H2S and HS—;
wherein the concentration of H2S is in the range of 1.0 mg/mL to 15.0 mg/mL;
wherein the solution is adjusted to a pH in the range of 7.5 to 8.5 by adding HCl to the solution;
wherein the solution has an osmolarity in the range of 250-330 mOsmol/L;
wherein the solution further comprises sulfide oxidation products selected from the group consisting of polysulfide, sulfite, sulfate and thiosulfate;
wherein the oxidation products comprise sulfate in the range of 0%-1.0%, sulfite in the range of 0%-1.0%, polysulfide in the range of 0%-1% or thiosulfate in the range of 0%-1.0%;
and wherein the solution is isotonic or near isotonic; and
wherein the disease, injury or disorder can be treated with liquid or gaseous chalcogenide compositions; is a surgery; is risk for reperfusion injury; is an ischemic or hypoxic condition arising from stroke, cardiac arrest, myocardial infarction, or coronary artery bypass graft (CABG) surgery; is hemorrhagic shock, or; is hepatic injury.

2. The method of claim 1, wherein the biological material is contacted with the composition before or after the injury or before or after onset or progression of the disease.

3. The method of claim 1, wherein said contacting is conducted intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, intraocularly, subcutaneously, subconjunctivally, intravesicularly, mucosally, intrapericardially, intraumbilically, orally, locally, by injection, by infusion, by continuous infusion, by absorption, by adsorption, by immersion, by localized perfusion, via a catheter, or via a lavage.

4. The method of claim 1, wherein the biological material is an organ donor and the organ donor is contacted with the composition prior to removal of donor organs for transport and transplantation into a recipient in need of an organ transplant.

5. The method of claim 1, wherein said contacting is parenteral administration.

* * * * *

UNITED STATES PATENT AND TRADEMARK OFFICE
CERTIFICATE OF CORRECTION

| | | |
|---|---|---|
| PATENT NO. | : 8,226,986 B2 | Page 1 of 1 |
| APPLICATION NO. | : 13/049220 | |
| DATED | : July 24, 2012 | |
| INVENTOR(S) | : Kevin J. Tomaselli et al. | |

It is certified that error appears in the above-identified patent and that said Letters Patent is hereby corrected as shown below:

Column 49
Claim 1, line 6, "Na2S, H2S" should read -- $Na_2S$, $H_2S$ --

Claim 1, line 8, "H2S" should read -- $H_2S$ --

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,226,986 B2
APPLICATION NO. : 13/049220
DATED : July 24, 2012
INVENTOR(S) : Kevin J. Tomaselli et al.

Page 1 of 1

It is certified that error appears in the above-identified patent and that said Letters Patent is hereby corrected as shown below:

Column 49, line 49 (Claim 1, line 6) "Na2S, H2S" should read -- $Na_2S$, $H_2S$ --

Column 49, line 51 (Claim 1, line 8) "H2S" should read -- $H_2S$ --

This certificate supersedes the Certificate of Correction issued March 12, 2013.

Signed and Sealed this
Ninth Day of April, 2013

Teresa Stanek Rea
*Acting Director of the United States Patent and Trademark Office*